US007968092B2

(12) United States Patent
Throsby et al.

(10) Patent No.: US 7,968,092 B2
(45) Date of Patent: Jun. 28, 2011

(54) HUMAN BINDING MOLECULE AGAINST CD1A

(75) Inventors: Mark Throsby, Utrecht (NL); Marja van Meijer, Amsterdam (NL); Wilfred T. V. Germeraad, Gronsveld (NL); Robert J. Arceci, Baltimore, MD (US); Ada M. Kruisbeek, Amsterdam (NL)

(73) Assignees: Crucell Holland B.V., Leiden (NL); The Johns Hopkins University, Baltimore, MD (US)

( * ) Notice: Subject to any disclaimer, the term of this patent is extended or adjusted under 35 U.S.C. 154(b) by 1053 days.

(21) Appl. No.: 11/387,997

(22) Filed: Mar. 23, 2006

(65) Prior Publication Data

US 2006/0257397 A1 Nov. 16, 2006

Related U.S. Application Data

(63) Continuation-in-part of application No. PCT/EP2004/053639, filed on Dec. 21, 2004.

(30) Foreign Application Priority Data

Dec. 23, 2003 (WO) .................. PCT/EP03/51096
Sep. 9, 2004 (WO) ................. PCT/EP2004/052110

(51) Int. Cl.
*C07K 16/00* (2006.01)
*A61K 39/00* (2006.01)
*A61K 39/395* (2006.01)
*C12P 21/00* (2006.01)

(52) U.S. Cl. ............. 424/142.1; 424/143.1; 530/388.15; 530/388.22

(58) Field of Classification Search ........................ None
See application file for complete search history.

(56) References Cited

U.S. PATENT DOCUMENTS

2001/0051156 A1 12/2001 Zeng et al.
2003/0211553 A1 11/2003 Logtenberg et al.

FOREIGN PATENT DOCUMENTS

WO WO 01/82960 A1 11/2001
WO WO 02/06347 A1 1/2002
WO WO 2005/063819 7/2005

OTHER PUBLICATIONS

De Pascalis et al (J. Immunol. 2002, 169: 3076-3084).*
Casset et al (2003, BBRC 307: 198-205).*
Bechan et al (Blood Nov. 2005, 106: 4815).*
Rudikoff et al, PNAS USA 1982, 79: 1979-1983.*
Panka et al, PNAS USA 85: 3080-3084 1988.*
Amit et al, Science, 233, 747-753, 1986.*
Evolutionary Concepts in Genetics and Genomics. 2003, worldwideweb at.ncbi.nlm.nih.gov/bookshelf/br.fcgi?book=sef&part=A22.*

PCT International Search Report, PCT/EP2004/053639, dated Aug. 30, 2005.
Amiot et al., "HLA class I molecules are associated with CD1 a heavy chains on normal human thymus cells," Proc. Natl. Acad. Sci., Jun. 1988, pp. 4451-4545, vol. 85.
Vaughan et al., "Human antibodies by design," Nature Biotechnology, Jun. 1998, pp. 535-539, vol. 16.
Dezutter-Dambuyant et al., DMC1 : A Monoclonal Antibody Produced from Histiocytosis X Cells Which Reacts with the Native CD1a Molecule of Human Epidermal Langerhans Cells, Hybridoma, 1989, vol. 8, No. 2, Mary Ann Liebert, Inc., Publishers.
Moulon et al., A Potential Role for CD1 a Molecules on Human Epidermal Langerhans Cells in Allogeneic T-Cell Activation, The Journal of Investigative Dermatology, Sep. 1991, pp. 524-28, vol. 97 No. 3, The Society for Investigative Dermatology, Inc.
Murray et al., Diagnostic and Therapeutic Evaluation of an Anti-Langerhans Cell Histiocytosis Monoclonal Antibody (Na1/34) in a New Xenograft Model, The Journal of Investigative Dermatology, Jan. 2000, pp. 127-134, vol. 114, No. 1, The Society for Investigative Dermatology, Inc.
Amiot M., Bernard A., Raynal B., Knapp W., Deschildre C. and Boumsell L. (1986), J. Immunol. 136:1752-1757.
Boel E., Verlaan S., Poppelier M.J, Westerdaal N.A., Van Strijp J.A. and Logtenberg T. (2000), J. Immunol. Methods 239:153-166.
Burton D.R. and Barbas C. E. (1994) Adv. Immonol 57:191-280.
De Kruif J., Terstappen L., Boel E. and Logtenberg T. (1995). Proc. Natl. Acad. Sci. USA 92:3938-3942.
De Kruif J., Boel E. and Logtenberg T. (1995). J. Mol. Biol. 248:97-105.
Fidler I.I. Gerstern D.M. and Budmen M. B. (1976), Cancer Research 36:3610-3165.
Furue M., Nindl M., Kawabe K., Nakamura K., Ishibashi Y. and Sagawa K. (1992), J. Am. Acad. Dermatol. 27:419-426.
Ghetie M.A., Bright H. and Vitetta E.S. (2001), Blood 97:1392-1398.
Huls G., Heijnen I.J., Cuomo E., van der Linden J., Boel E., van de Winkel J. and Logtenberg T. (1999), Cancer Res. 59:5778-5784.
Jonuleit H., Kühn U., Müller G., Steinbrink K., Paragnik L., Schmitt E., Knop J., Enk A.H. (1997), Eur. J. Immunology 27:3135-3142.
Kelly K.M., Beverly P.C., Chu A.C., Davenport V., Gordon I., Smith M. and Pritchard J. (1994), J. Pediatr. 125:717-722.
Merle-Beral H., Boumsell L. Michel A. and Dehre P. (1989) Br. J. Haematol 72:209-212.
Salomone M.C. Roisman E.R. Santiago J., Satz M. L. and Fainboim L. (1990) Dis. Markers 8:265-274.
Salomone M.C. Roisman E.R. Santiago J., Satz M. L. and Fainboim L. (1990) Dis. Markers 8:275-281.
Teunissen M.B. (1992) Histochem. J. 24:697-716.
Van Kroonenburgh M.J. and Pauwels E.K. (1988) Nucl. Med Commun. 9:919-910.
U.S. Appl. No. 11/990,974, Feb. 21, 2008, Method for Preparing Immunoglobulin Libraries, Throsby et al.
U.S. Appl. No. 12/227,029, Nov. 5, 2008, Human Binding Molecules Having Killing Activity Against *Staphylococci* and uses Thereof, Throsby et al.

(Continued)

*Primary Examiner* — Gerald Ewoldt
*Assistant Examiner* — Marianne Dibrino
(74) *Attorney, Agent, or Firm* — TraskBritt, P.C.

(57) ABSTRACT

The present invention provides human binding molecules that specifically bind to CD1a, nucleic acid molecules encoding the human binding molecules, compositions comprising the human binding molecules and methods of identifying or producing the human binding molecules. The human binding molecules can be used in the diagnosis, prevention and treatment of neoplastic disorders and diseases.

5 Claims, 17 Drawing Sheets

OTHER PUBLICATIONS

U.S. Appl. No. 12/227,116, Nov. 7, 2008, Human Binding Molecules Having Killing Activity Against *Enterococci* and Uses Thereof, Throsby et al.

U.S. Appl. No. 12/310,812, Mar. 6, 2009, Human Binding Molecules Capble of Neutralizing Influenza Virus H5N1 and Uses Thereof, Van den Brink et al.

U.S. Appl. No. 61/215,890, May 11, 2009, Human Binding Molecules Capable of Neutralizing Influenza virus H3N2 and Uses Therof, Throsby et al.

O'Brien et al., Humanization of Monoclonal Antibodies by CDR Grafting, Methods in Molecular Biology, pp. 81-100, Sep. 16, 2002, vol. 207, Chapter 5, Totowa, NJ, USA.

* cited by examiner

CD1a Positive B16 Melanoma Cells Bound to C2113 Mab

4°C                           37°C

CD1a Positive B16 Melanoma Cells Bound to NA1/34 Mab

4°C                           37°C

HUMAN BINDING MOLECULE AGAINST CD1A

CROSS-REFERENCE TO RELATED APPLICATIONS

This application is a continuation-in-part of PCT International Patent Application No. PCT/EP2004/053639, filed on Dec. 21, 2004, designating the United States of America, and published in English, as PCT International Publication No. WO 2005/063819 A2 on Jul. 14, 2005, which claims the benefit under 35 U.S.C. §119 of International Patent Application PCT/EP03151096, filed Dec. 23, 2003, and International Patent Application PCT/EP2004/052110, filed Sep. 9, 2004, the contents of the entirety of each of which is incorporated by this reference.

STATEMENT ACCORDING TO 37 C.F.R. §1.52(e)(5)-SEQUENCE LISTING SUBMITTED ON COMPACT DISC

Pursuant to 37 C.F.R. §1.52(e)(1)(iii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "2578-7736 Seq List.txt" which is 155 KB and created on Mar 23, 2006.

BACKGROUND OF THE INVENTION

Field of the Invention: The invention relates to the identification of human binding molecules capable of specifically binding to CD1a, to immunoconjugates comprising these binding molecules and to methods of obtaining the binding molecules. The invention further encompasses the use of the human binding molecules in medicine, in particular for the diagnosis, prevention and/or treatment of neoplastic diseases and Langerhans Cell Histiocytosis.

CD1 molecules are a family of molecules that are expressed on the surfaces of dendritic cells, monocytes, and some thymocytes. CD1 molecules are similar to MHC Class I molecules in that they are involved in antigen presentation. Five CD1 genes have thus far been identified in humans: CD1a, CD1b, CD1c, CD1d and CD1e. Four of these five CD1 gene products have been defined serologically. They are referred to as CD1a, CD1b, CD1c and CD1d and are distinguished by unique heavy chains with approximate molecular weights of 49 kDa, 45 kDa, 43 kDa and 48 kDa, respectively.

The fact that CD1a molecules are expressed by acute and chronic leukemic cells of the pre-B, B, T and non-lymphoid lineages renders CD1a in principle a target to detect or attack these disorders (Salarnone et al. (1990a), Salamone (1990b), Merle-Beral et al. (1989)).

Furthermore, CD1a molecules are present on Langerhans cells (which are the major dendritic antigen-presenting cells in the skin) (Teunissen (1992)). This renders CD1a in principle a target to detect or treat Langerhans Cell Histiocytosis (LCH), a clonal proliferative neoplasm with variable clinical manifestations, ranging from solitary, self-limiting lesions to multisystem disease that can be life threatening.

Binding molecules that specifically bind to CD1a might be very useful in diagnosis and treatment of the above-mentioned disorders. Several murine monoclonal antibodies directed against CD1a are known in the art (Kelly (1994), Amiot et al. (1986), Furue et al. (1992)). However, murine antibodies, in naked or immunoconjugated format, are limited for their use in vivo due to problems associated with administration of murine antibodies to humans, such as short serum half life, an inability to trigger certain human effector functions and elicitation of an unwanted dramatic immune response against the murine antibody in a human (the "human antimouse antibody" (HAMA) reaction) (Van Kroonenburgh and Pauwels (1988)).

In general, attempts to overcome the problems associated with use of fully murine antibodies in humans, have involved genetically engineering the antibodies to be more "human-like." A first stage in the humanization process was preparing chimeric antibodies, i.e., antibodies in which the variable regions of the antibody chains are murine-derived and the constant regions of the antibody chains are human-derived. Subsequently, domains between the variable domains that specify the antigen binding were replaced by their human counterparts leading to so-called humanized antibodies. A disadvantage of these chimeric and humanized antibodies is that they still retain some murine sequences and therefore still elicit an unwanted immune reaction, especially when administered for prolonged periods.

In view of their benefit in therapy there is still a need for human binding molecules against CD1a.

The present invention provides human binding molecules against CD1a that can be used in medicine, in particular for diagnosis, prevention and/or treatment of CD1a-associated disorders.

BRIEF DESCRIPTION OF THE SEVERAL VIEWS OF THE DRAWINGS

FIG. 5.

FIG. 6.

DETAILED DESCRIPTION OF THE INVENTION

Figure 1:
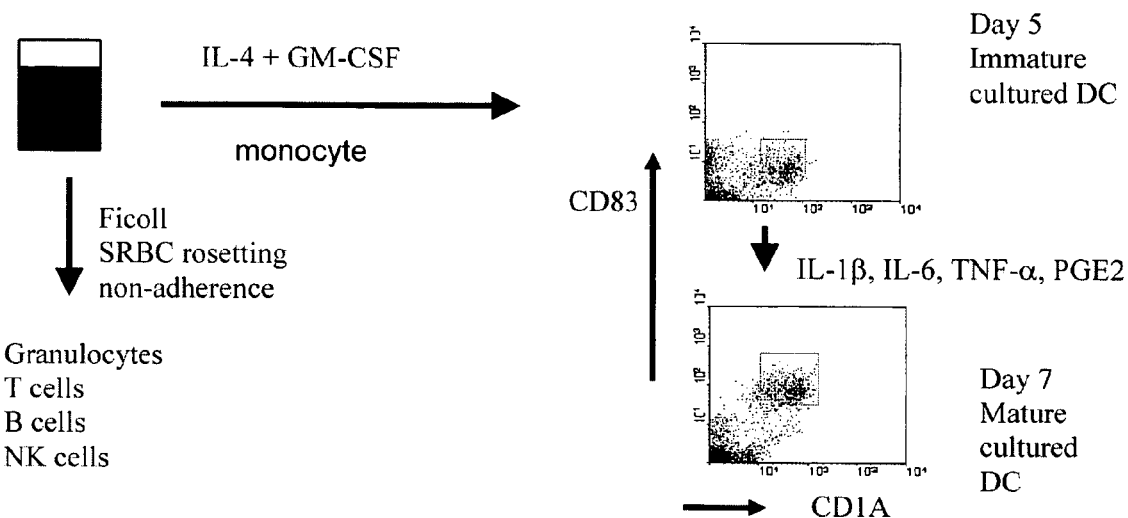
FIG. 1. Isolation of monocytes and differentiation of monocytes to immature dendritic cells (DCs) by IL-4 and GM-CSF and to mature DCs by an additional cocktail containing IL-1β, IL-6, TNF-α, PGE2. Indicated in the FACS pictures are a mixture of PBLs, used as subtractor cells during phage selection, and cultured DCs (boxed), wherein the amount of PBLs is about ten times the amount of DCs.

Hereinbelow follow the definitions of the terms as used in the invention.

DEFINITIONS

Acute myeloid leukemia: As used herein, the term "acute myeloid leukemia" is characterized by an uncontrolled proliferation of progenitor cells of myeloid origin including, but not limited to, myeloid progenitor cells, myelomonocytic progenitor cells, immature megakaryoblasts. Subtypes of acute myeloid leukemia (AML) include according to the FAB classification FAB-M0, FAB-M1, FAB-M2, FAB-M3, FAB-M4, FAB-M5, FAB-M6 and FAB-M7.

Amino acid sequence: The term "amino acid sequence," as used herein, refers to naturally occurring or synthetic molecules and to a peptide, oligopeptide, polypeptide or protein sequence.

Apoptosis: As used herein, the term "apoptosis" refers to any cell death, orderly or controlled that results from the complex cascade of cellular events that occur at specific stages of cellular differentiation and in response to specific stimuli. Apoptosis is characterized and/or accompanied by one or more characteristic cell changes, including, but not limited to, condensation of cytoplasm, loss of plasma membrane microvilli, segmentation of the nucleus, degradation of chromosomal DNA or loss of mitochondrial function. Apoptosis can be determined and measured, for instance, by cell viability assays, FACS analysis or DNA electrophoresis, all of which are known in the art.

Binding molecule: As used herein, the term "binding molecule" refers to an intact immunoglobulin including monoclonal antibodies, such as chimeric, humanized or human monoclonal antibodies, or to an antigen-binding and/or variable domain comprising fragment of an immunoglobulin that competes with the intact immunoglobulin for specific binding to the binding partner of the immunoglobulin, e.g., CD1a. Regardless of structure, the antigen-binding fragment binds with the same antigen that is recognized by the intact immunoglobulin. The term "binding molecule," as used herein includes immunoglobulins from classes and subclasses of intact antibodies. These include IgA, IgD, IgE, IgG, and IgM, and several of these may be further divided into subclasses (isotypes), e.g., IgA1, IgA2, IgG1, IgG2, IgG3 and IgG4 as well as antigen-binding fragments thereof.

Antigen-binding fragments include, inter alia, Fab, F(ab'), F(ab')$_2$, Fv, dAb, Fd, complementarity determining region (CDR) fragments, single-chain antibodies (scFv), bivalent single-chain antibodies, diabodies, triabodies, tetrabodies, (poly)peptides that contain at least a fragment of an immunoglobulin that is sufficient to confer specific antigen binding to the (poly)peptide, etc. The above fragments may be produced synthetically or by enzymatic or chemical cleavage of intact immunoglobulins or they may be genetically engineered by recombinant DNA techniques. The methods of production are well known in the art and are described, for example, in *Antibodies: A Laboratory Manual*, edited by E. Harlow and D. Lane (1988), Cold Spring Harbor Laboratory, Cold Spring Harbor, N.Y., which is incorporated herein by reference. A binding molecule or antigen-binding fragment thereof may have one or more binding sites. If there is more than one binding site, the binding sites may be identical to one another or they may be different.

The binding molecule can be a naked or unconjugated binding molecule. A naked or unconjugated binding molecule is intended to refer to a binding molecule that is not conjugated, operatively linked or otherwise physically or functionally associated with an effector moiety or tag, such as inter alia a toxic substance, a radioactive substance, a liposome, an enzyme. It will be understood that naked or unconjugated binding molecules do not exclude binding molecules that have been stabilized, multimerized, humanized or in any other way manipulated, other than by the attachment of an effector moiety or tag. Accordingly, all post-translationally modified naked and unconjugated binding molecules are included herewith, including where the modifications are made in the natural binding molecule-producing cell environment, by a recombinant binding molecule-producing cell, and are introduced by the hand of man after initial binding molecule preparation. Of course, the term naked or unconjugated binding molecule includes binding molecules having the ability to form functional associations with effector cells and/or molecules after administration to the body, as some such interactions are necessary in order to exert a biological effect.

Biological sample: As used herein, the term "biological sample" encompasses a variety of sample types, including blood and other liquid samples of biological origin, solid tissue samples such as a biopsy specimen or tissue cultures, or cells derived therefrom and the progeny thereof. The term also includes samples that have been manipulated in any way after their procurement, such as by treatment with reagents, solubilization, or enrichment for certain components, such as proteins or polynucleotides. The term encompasses various kinds of clinical samples obtained from any species, and also includes cells in culture, cell supernatants and cell lysates.

Chronic myeloid leukemia: The term "chronic myeloid leukemia," as used herein, is characterized by an uncontrolled proliferation of myelopoietic cells in the bone marrow and extramedullary sites in which the malignant myeloblast is able to differentiate and give rise to myelocytes, metamyelocytes, band cells and granulocytes.

Complementary determining regions (CDR): The term "complementary determining regions," as used herein, means sequences within the variable regions of binding molecules, such as immunoglobulins, that generate the antigen binding site which is complementary in shape and charge distribution to the epitope recognized on the antigen. The CDR regions can be specific for linear epitopes, discontinuous epitopes, or conformational epitopes of proteins or protein fragments, either as present on the protein in its native conformation or, in some cases, as present on the proteins as denatured, e.g., by solubilization in SDS. Epitopes may also consist of post translational modifications of proteins.

Deletion: The term "deletion," as used herein, denotes a change in either amino acid or nucleotide sequence in which one or more amino acid or nucleotide residues, respectively, are absent as compared to the parent, often the naturally occurring, molecule.

Expression-regulating nucleic acid sequence: The term "expression-regulating nucleic acid sequence," as used herein, refers to polynucleotide sequences necessary for and/or affecting the expression of an operably linked coding sequence in a particular host organism. When two nucleic acid sequences are operably linked, they usually will be in the same orientation and also in the same reading frame. They usually will be essentially contiguous, although this may not be required. The expression-regulating nucleic acid sequences, such as inter alia appropriate transcription initiation, termination, promoter, enhancer sequences; repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion, can be any nucleic acid sequence showing activity in the host organism of choice and can be derived from genes encoding proteins, which are either homologous or heterologous to the host organism.

Functional variant: The term "functional variant," as used herein, refers to a binding molecule that comprises a nucleotide and/or amino acid sequence that is altered by one or more nucleotides and/or amino acids compared to the nucleotide and/or amino acid sequences of the parent binding molecule and that is still capable of competing for binding to the binding partner, e.g., CD1a, with the parent binding molecule. In other words, the modifications in the amino acid and/or nucleotide sequence of the parent binding molecule do not significantly affect or alter the binding characteristics of the binding molecule encoded by the nucleotide sequence or containing the amino acid sequence, i.e., the binding molecule is still able to recognize and bind its target. The functional variant may have conservative sequence modifications including nucleotide and amino acid substitutions, additions and deletions. These modifications can be introduced by standard techniques known in the art, such as site-directed mutagenesis and random PCR-mediated mutagenesis.

Conservative amino acid substitutions include, for instance, the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Furthermore, a variant may have non-conservative amino acid substitutions, e.g., replacement of an amino acid with an amino acid residue having different structural or chemical properties. Similar minor variations may also include amino acid deletions or insertions, or both. Guidance in determining which amino acid residues may be substituted, inserted, or deleted without abolishing immunological activity may be found using computer programs well known in the art.

A mutation in a nucleotide sequence can be a single alteration made at a locus (a point mutation), such as transition or transversion mutations, or alternatively, multiple nucleotides may be inserted, deleted or changed at a single locus. In addition, one or more alterations may be made at any number of loci within a nucleotide sequence. The mutations may be performed by any suitable method known in the art.

Host: The term "host," as used herein, is intended to refer to an organism or a cell into which a vector such as a cloning vector or an expression vector has been introduced. The organism or cell can be prokaryotic or eukaryotic. It should be understood that this term is intended to refer not only to the particular subject organism or cell, but to the progeny of such an organism or cell as well. Because certain modifications may occur in succeeding generations due to either mutation or environmental influences, such progeny may not, in fact, be identical to the parent organism or cell, but are still included within the scope of the term "host" as used herein.

Human: The term "human," when applied to binding molecules as defined herein, refers to molecules that are either directly derived from a human or based upon a human sequence. When a binding molecule is derived from or based on a human sequence and subsequently modified, it is still to be considered human as used throughout the specification. In other words, the term "human," when applied to binding molecules is intended to include binding molecules having variable and constant regions derived from human germline immunoglobulin sequences based on variable or constant regions either or not occurring in a human or human lymphocyte or in modified form. Thus, the human binding molecules may include amino acid residues not encoded by human germline immunoglobulin sequences, comprise substitutions and/or deletions (e.g., mutations introduced by, for instance, random or site-specific mutagenesis in vitro or by somatic mutation in vivo).

"Based on," as used herein, also refers to the situation that a nucleic acid sequence may be exactly copied from a template, or with minor mutations, such as by error-prone PCR methods, or synthetically made matching the template exactly or with minor modifications. Semi-synthetic molecules based on human sequences are also considered to be human as used herein.

Immunoliposome: The term "immunoliposome" refers to a liposome bearing a binding molecule, as defined herein, that acts as a targeting moiety enabling the liposome to specifically bind to the binding partner of the binding molecule. The binding partner may be present in solution or may be bound to the surface of a cell.

Insertion: The term "insertion," also known as the term "addition," denotes a change in an amino acid or nucleotide sequence resulting in the addition of one or more amino acid or nucleotide residues, respectively, as compared to the parent, often the naturally occurring, molecule.

Internalizing binding molecule: The term "internalizing binding molecule," as used herein, means a binding molecule as defined herein that is capable of being internalized within the target cells to which it binds. In other words, the binding molecule is taken up, i.e., transported from the outside (cell surface) of a target cell to the inside, e.g., into the endosomal compartment or other compartment or into the cytoplasm of the cell, by the target cells upon binding to the binding partner of the binding molecule.

Isolated: The term "isolated," when applied to binding molecules as defined herein, refers to binding molecules that are substantially free of other proteins or polypeptides, particularly free of other binding molecules having different antigenic specificities, and are also substantially free of other cellular material and/or chemicals. For example, when the binding molecules are recombinantly produced, they are preferably substantially free of culture medium, and when the binding molecules are produced by chemical synthesis, they are preferably substantially free of chemical precursors or other chemicals, i.e., they are separated from chemical precursors or other chemicals which are involved in the synthesis of the protein. The term "isolated" when applied to nucleic acid molecules encoding binding molecules as defined herein, is intended to refer to nucleic acid molecules in which the nucleotide sequences encoding the binding molecules are free of other nucleotide sequences, particularly nucleotide sequences encoding binding molecules that bind binding partners other than CD1a. Furthermore, the term "isolated" refers to nucleic acid molecules that are substantially separated from other cellular components that naturally accompany the native nucleic acid molecule in its natural host, e.g., ribosomes, polymerases, or genomic sequences with which it is naturally associated. Moreover, "isolated" nucleic acid molecules, such as cDNA molecules, can be substantially free of other cellular material, or culture medium when produced by recombinant techniques, or substantially free of chemical precursors or other chemicals when chemically synthesized.

Langerhans Cell Histiocytosis (LCH): The term "Langerhans Cell Histiocytosis (LCH)" refers to a disorder which is characterized by localized or generalized proliferation of dendritic-like cells, resembling Langerhans cells. These cells have their origin in the bone marrow and are normally mainly present in the skin. In LCH these cells proliferate and may or may not affect many other organs like among others bone, liver, lungs and brain. LCH is the most frequent among the histiocytic disorders. The disease occurs in persons of all ages, but the peak incidence is in children between zero and four years. Clinical symptoms vary widely from limited skin rash or single bone lesions, which may heal spontaneously, to extensive visceral organ involvement and dysfunction, eventually leading to patient death.

Liposome: The term "liposome," as used herein, refers to a small vesicle bounded by a layer composed of various types of lipids, preferably amphipathic lipids, phospholipids and/or surfactants and made artificially from these molecules by techniques known in the art such as sonication or removal of detergent from phospholipid-detergent complexes. The layer typically is a bilayer formed by molecules that comprise a hydrophobic portion and a hydrophilic portion, wherein hydrophobic portions associate in an aqueous medium to form an internal part of the layer, whereas hydrophilic portions remain in contact with the medium. The layer surrounds and encloses an interior, which may contain, wholly or partially, an aqueous phase, a solid, a gel, a gas phase, or a non-aqueous fluid. Liposomes are useful for delivery of one or more molecules such as nucleic acid molecules, binding molecules, proteins, toxic substances and other material or compounds into cells such as animal cells by liposome fusion with the plasma membrane, a process also called lipofection. The molecules may be contained within the interior of the liposome, in the lipid layer, or attached to the outer surface of the lipid layer.

Monoclonal antibody: The term "monoclonal antibody," as used herein, refers to a monoclonal antibody displaying a single binding specificity and affinity for a particular epitope. Accordingly, the term "human monoclonal antibody" refers to an antibody displaying a single binding specificity which have variable and constant regions derived from human germline immunoglobulin sequences or derived from completely synthetic or semi-synthetic sequences.

Myelodysplastic syndrome: The term "myelodysplastic syndrome," as used herein, encompasses a heterogeneous group of closely related clonal hematopoietic disorders that originate in an early blood-forming cell in the marrow. All disorders are characterized by a cellular marrow with impaired morphology and maturation (dysmyelopoiesis) and peripheral blood cytopenias, resulting from ineffective blood cell production. In other words, the maturing blood cells often die in the marrow before they reach full maturity and enter the blood, accounting for the low blood cell concentrations. In patients suffering from myelodysplastic syndrome there may also be an accumulation of very immature marrow cells, called leukemic blast cells.

Naturally occurring: The term "naturally occurring," as used herein, as applied to an object refers to the fact that an object can be found in nature. For example, a polypeptide or polynucleotide sequence that is present in an organism that can be isolated from a source in nature and which has not been modified by man in the laboratory is naturally occurring.

Neoplastic cells: The term "neoplastic cells," as used herein, refers to cells that result from undesired autonomous new growth which has no apparent physiological function. A neoplastic cell further includes transformed cells and cancer cells including blood cancers (benign and malignant).

Nucleic acid molecule: The term "nucleic acid molecule," as used in the present invention, refers to a polymeric form of nucleotides and includes both sense and antisense strands of RNA, cDNA, genomic DNA, and synthetic forms and mixed polymers of the above. A nucleotide refers to a ribonucleotide, deoxynucleotide or a modified form of either type of nucleotide. The term also includes single- and double-stranded forms of DNA. In addition, a polynucleotide may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hair-pinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for antisense therapy, hybridization probes and PCR primers.

Operably linked: The term "operably linked" refers to two or more nucleic acid sequence elements that are physically linked and are in a functional relationship with each other. For instance, a promoter is operably linked to a coding sequence if the promoter is able to initiate or regulate the transcription or expression of a coding sequence, in which case the coding sequence should be understood as being "under the control of" the promoter. Generally, when two nucleic acid sequences are operably linked, they will be in the same orientation and usually also in the same reading frame. They usually will be essentially contiguous, although this may not be required.

Pharmaceutically acceptable excipient: By "pharmaceutically acceptable excipient" is meant any inert substance that is combined with an active molecule such as a drug, agent, or binding molecule for preparing an agreeable or convenient dosage form. The "pharmaceutically acceptable excipient" is an excipient that is non-toxic to recipients at the dosages and concentrations employed and is compatible with other ingredients of the formulation comprising the drug, agent, or binding molecule.

Specifically Binding: The term "specifically binding," as used herein, in reference to the interaction of a binding molecule, e.g., an antibody, and its binding partner, e.g., an antigen, means that the interaction is dependent upon the presence of a particular structure, e.g., an antigenic determinant or epitope, on the binding partner. In other words, the antibody preferentially binds or recognizes the binding partner even when the binding partner is present in a mixture of other molecules. The binding may be mediated by covalent or non-covalent interactions or a combination of both.

Substitutions: A "substitution," as used herein, denotes the replacement of one or more amino acids or nucleotides by different amino acids or nucleotides, respectively.

Therapeutically effective amount: The term "therapeutically effective amount" refers to an amount of the binding molecule as defined herein that is effective for preventing and/or treating a disorder or disease wherein CD1a molecules play a role or are associated with, or ameliorating a condition associated with the disease or disorder.

Treatment: The term "treatment" refers to therapeutic treatment as well as prophylactic or preventative measures. Those in need of treatment include those already with the disease or disorder wherein CD1a molecules play a role or are associated with as well as those in which the disease or disorder is to be prevented.

Vector: The term "vector" denotes a nucleic acid molecule into which a second nucleic acid molecule can be inserted for introduction into a host where it will be replicated, and in some cases expressed. In other words, a vector is capable of carrying a second nucleic acid molecule to which it has been linked. Cloning as well as expression vectors are contemplated by the term "vector," as used herein. Vectors include, but are not limited to, plasmids, cosmids, bacterial artificial chromosomes (BAC) and yeast artificial chromosomes (YAC) and vectors derived from bacteriophages or plant or animal (including human) viruses. Vectors comprise an origin of replication recognized by the proposed host and in case of expression vectors, promoter and other regulatory regions recognized by the host. A vector containing a second nucleic acid molecule may be introduced into a cell by transformation, transfection, or by making use of viral entry mechanisms. Certain vectors are capable of autonomous replication in a host into which they are introduced (e.g., bacterial vectors having a bacterial origin of replication). Other vectors can be integrated into the genome of a host upon introduction into the host, and thereby are replicated along with the host genome.

SUMMARY OF THE INVENTION

In the present invention, several human binding molecules capable of binding to a human CD1a have been identified and obtained by using phage display technology. Furthermore, methods of producing these human binding molecules and the use of the human binding molecules in diagnosis, prevention and treatment of inter alia neoplastic disorders and diseases have been described.

DETAILED DESCRIPTION OF THE INVENTION

The present invention encompasses human binding molecules capable of specifically binding to human CD1a. The binding molecules are also capable of binding, particularly specifically binding, to a fragment of human CD1a, the fragment at least comprising the antigenic determinant of CD1a that is recognized by the human binding molecules of the invention. CD1a is a member of the nonclassical major histocompatibility complex family of proteins that play a critical role in the presentation of glycolipid, lipid, lipopeptide and some glycoprotein antigens to NK and T lymphocytes. CD1a is expressed on subsets of lymphomas, while normally it is only expressed on Langerhans cells and cortical thymocytes, both of which can be replenished from CD1a-negative precursor cells, making this antigen a potentially useful diagnostic and therapeutic target. Human binding molecules capable of specifically binding naturally occurring truncated or secreted forms, naturally occurring variant forms (e.g., alternatively spliced forms) and naturally occurring allelic variants of CD1a are also a part of the present invention. Binding molecules of the invention may also be capable of specifically binding to non-naturally occurring variants or analogues of CD1a as long as the modifications do not abolish the binding of the binding molecules to the CD1a molecules.

The human binding molecules according to the invention, can be intact immunoglobulin molecules such as polyclonal or monoclonal antibodies, or the binding molecules can be antigen-binding fragments including, but not limited to, Fab, F(ab'), F(ab')$_2$, Fv, dAb, Fd, complementarity determining region (CDR) fragments, single-chain antibodies (scFv), bivalent single-chain antibodies, diabodies, triabodies, tetrabodies, and (poly)peptides that contain at least a fragment of an immunoglobulin that is sufficient to confer specific antigen binding to the (poly)peptides. The human binding molecules of the invention can be used in non-isolated or isolated form. Furthermore, the human binding molecules of the invention can be used alone or in a mixture comprising at least one human binding molecule (or variant or fragment thereof). In other words, the human binding molecules can be used in combination, e.g., as a pharmaceutical composition comprising two or more human binding molecules or fragments thereof. For example, human binding molecules having different, but complementary activities can be combined in a single therapy to achieve a desired therapeutic or diagnostic effect, but alternatively, human binding molecules having identical activities can also be combined in a single therapy to achieve a desired therapeutic or diagnostic effect. The mixture may further comprise at least one other therapeutic agent. Typically, human binding molecules according to the invention, can bind to their binding partners, i.e., human CD1a, with an affinity constant ($K_d$-value) that is lower than $0.2 \times 10^{-4}$ M, $1.0 \times 10^{-5}$ M, $1.0 \times 10^{-6}$ M, $1.0 \times 10^{-7}$ M, preferably lower than $1.0 \times 10^{-8}$ M, more preferably lower than $1.0 \times 10^{-9}$ M, more preferably lower than $1.0 \times 10^{-10}$ M, even more preferably lower than $1.0 \times 10^{-11}$ M, and, in particular, lower than $1.0 \times 10^{-12}$ M. The affinity constants can vary for antibody isotypes. For example, affinity binding for an IgM isotype refers to a binding affinity of at least about $1.0 \times 10^{-7}$ M. Affinity constants can, for instance, be measured using surface plasmon resonance, i.e., an optical phenomenon that allows for the analysis of real-time biospecific interactions by detection of alterations in protein concentrations within a biosensor matrix, for example, using the BIAcore system (Pharmacia Biosensor AB, Uppsala, Sweden).

The human binding molecules according to the invention, may bind to human CD1a in soluble form or may bind to human CD1a bound or attached to a carrier or substrate, e.g., microtiter plates, membranes and beads, etc. Carriers or substrates may be made of glass, plastic (e.g., polystyrene), polysaccharides, nylon, nitrocellulose, or Teflon, etc. The surface of such supports may be solid or porous and of any convenient shape. Furthermore, the human binding molecules may bind to the human CD1a in purified or non-purified form. Preferably, the human binding molecules are capable of specifically binding to human CD1a molecules associated with cells, such as a human CD1a-positive cells or portions or parts of these cells comprising human CD1a or a fragment thereof.

In an embodiment of the invention, the human binding molecules of the invention which stay bound to the surface upon binding to human CD1a present on the surface of target cells may be used in the format of naked binding molecules to support possible effector functions of antibody-dependent cellular cytotoxicity (ADCC) and complement-dependent cytotoxicity (CDC).

ADCC refers to a cell-mediated reaction in which non-specific cytotoxic cells that express Fc receptors (FcRs) (e.g., Natural Killer (NK) cells, neutrophils, and macrophages) recognize the so-called Fc portion of binding molecules while the latter bind to a target cell and subsequently cause lysis of the target cell. CDC refers to the ability of a molecule to lyse a target in the presence of complement. The complement activation pathway is initiated by the binding of the first component of the complement system (Clq) to a binding molecule complexed with a cognate antigen. To distinguish cell death induced by antibody-dependent cell-mediated/cellular cytotoxicity (ADCC) or complement-dependent cytotoxicity (CDC), cell death may be determined in vitro in the absence of complement and immune effector cells. The assay for cell death may, for instance, be performed using heat inactivated serum (i.e., in the absence of complement) and in the absence of immune effector cells. To determine whether the binding molecule is able to induce cell death, loss of membrane integrity as evaluated by uptake of propidium iodide (PI), trypan blue or 7AAD can be assessed relative to untreated cells.

Naked antibodies according to the invention, may also induce apoptosis of target cells in another way than by means of ADCC or CDC. Target cells include, but are not limited to, CD1a-positive cells such as neoplastic cells. Methods of measuring apoptosis are known to a skilled artisan and include, but are not limited to, FACS analysis using Annexin V staining, DNA electrophoresis, uptake of propidium iodide (PI), trypan blue or 7AAD. In case the antibody is capable of inducing apoptosis or cell death in the absence of effector cells and/or in the absence of complement, the antibody is said to have intrinsic cytotoxicity or apoptotic activity.

Naked binding molecules according to the invention, may also be used to inhibit or block the binding of another molecule, such as a ligand, normally binding to CD1a. This way the human binding molecules could interfere with one or more possible downstream processes that are triggered/activated by the binding/interaction of the molecule to CD1a.

Alternatively, upon binding to CD1a molecules present on the surface of target cells, the human binding molecules as defined herein may internalize. Internalization of binding molecules can be assayed by known techniques that include, but are not limited to, specifically tracing internalized binding molecules capable of binding CD1a molecules. The binding molecules may be labeled with a fluorochrome and internalization may be measured by means of flow cytometry or confocal scanning laser microscopy.

In case the human binding molecules as defined in the present invention are slowly internalizing and, before internalization, stay bound to the surface of target cells for a prolonged period of time, they may be useful, similarly as binding molecules that do not internalize at all, in therapies which make use of ADCC, CDC, apoptosis or antibody-directed enzyme-prodrug therapy (ADEPT). ADCC, CDC and apoptosis are discussed above, while ADEPT is discussed below.

In a preferred embodiment, the human binding molecules according to the invention, comprises at least a CDR3 region, preferably HCDR3 region, comprising the amino acid sequence selected from the group consisting of SEQ ID NO:1, SEQ ID NO:2, SEQ ID NO:3, SEQ ID NO:4, SEQ ID NO:5, and SEQ ID NO:6. In a preferred embodiment, the human binding molecules according to the invention, comprises at least a CDR3 region, preferably HCDR3 region, comprising the amino acid sequence selected from the group consisting of SEQ ID NO:1 and SEQ ID NO:6. The further CDR regions of the human binding molecules comprising the HCDR3 region comprising the amino acid sequence selected from the group consisting of SEQ ID NO:1 and SEQ ID NO:6 are shown in Table 3.

In yet another embodiment, the human binding molecules according to the invention, comprise a variable heavy chain comprising the amino acid sequence selected from the group consisting of SEQ ID NO:8, SEQ ID NO:10, SEQ ID NO:12, SEQ ID NO:14, SEQ ID NO:16 and SEQ ID NO:18. Preferably, the group consists of SEQ ID NO:8 and SEQ ID NO:18.

In a further embodiment, the human binding molecules according to the invention, comprise a variable heavy chain comprising the amino acid sequence shown in SEQ ID NO:8 and a variable light chain comprising the amino acid sequence of SEQ ID NO:20, a variable heavy chain comprising the amino acid sequence shown in SEQ ID NO:10 and a variable light chain comprising the amino acid sequence of SEQ ID NO:20, a variable heavy chain comprising the amino acid sequence shown in SEQ ID NO:12 and a variable light chain comprising the amino acid sequence of SEQ ID NO:22, a variable heavy chain comprising the amino acid sequence shown in SEQ ID NO:14 and a variable light chain comprising the amino acid sequence of SEQ ID NO:20, a variable heavy chain comprising the amino acid sequence shown in SEQ ID NO:16 and a variable light chain comprising the amino acid sequence of SEQ ID NO:20, a variable heavy chain comprising the amino acid sequence shown in SEQ ID NO:18 and a variable light chain comprising the amino acid sequence of SEQ ID NO:20. Plasmids comprising DNA encoding the heavy chain or light chain of human IgG1 antibodies directed against human CD1a, the antibodies being called 02-113, 02-114, 02-115, 02-116, 02-117 and 02-118, have been deposited. The plasmids comprising DNA encoding the anti-CD1a human IgG1 heavy chains were called pgG102-113C03, pgG102-114C03, pgG102-115C03, pgG102-116C03, pgG102-117C03 and pgG102-118C03 and were deposited at the European Collection of Cell Cultures (ECACC), CAMR, Salisbury, Wiltshire SP4 OJG, Great Britain on 28 Oct. 2003, under accession numbers 03102801, 03102802, 03102803, 03102804, 03102805 and 03102806, respectively. The plasmid comprising DNA encoding the light chain of the anti-CD1a human IgGIs called 02-113, 02-114, 02-116, 02-117 and 02-118 was called pSyn-C05-VkI and was deposited at the European Collection of Cell Cultures (ECACC), CAMR, Salisbury, Wiltshire SP4 OJG, Great Britain on 28 Oct. 2003, under accession number 03102807. The plasmid comprising DNA encoding the light chain of the anti-CD1a human IgG1s called 02-115 was called pSyn-C04-V13 and was deposited at the European Collection of Cell Cultures (ECACC), CAMR, Salisbury, Wiltshire SP4 OJG, Great Britain on 28 Oct. 2003, under accession number 03102808.

Another aspect of the invention includes functional variants of binding molecules or fragments thereof as defined herein. Molecules are considered to be functional variants of a binding molecule according to the invention, if the variants are capable of competing for specifically binding to human CD1a, preferably competing for the same binding site on the human CD1a, with the parental binding molecules. In other words, when the functional variants are still capable of binding to human CD1a or a portion thereof. Preferably, functional variants of a binding molecule according to the invention, also have cytotoxic activity against a CD1a-expressing cells such as ADCC activity, CDC-activity and/or intrinsic cytotoxicity/apoptotic activity. The activity may be lower or equal to the activity of the parental binding molecule, but preferably the activity of the functional variant is higher than the activity of the parental binding molecule. Functional variants include, but are not limited to, derivatives that are substantially similar in primary structural sequence, but which contain e.g., in vitro or in vivo modifications, chemical and/or biochemical, that are not found in the parental binding molecule. Such modifications include inter alia acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI-anchor formation, hydroxylation, iodination, methylation, myristoylation, oxidation, pegylation, proteolytic processing, phosphorylation, prenylation, racemization, selenoylation, sulfation, transfer-RNA-mediated addition of amino acids to proteins such as arginylation, ubiquitination, and the like.

Alternatively, functional variants can be binding molecules as defined in the present invention comprising an amino acid sequence containing substitutions, insertions, deletions or combinations thereof of one or more amino acids compared to the amino acid sequences of the parental binding molecules. Furthermore, functional variants can comprise truncations of the amino acid sequence at either or both the amino or carboxy termini. Functional variants according to the invention, may have the same or different, either higher or lower, binding affinities compared to the parental binding molecule but are still capable of binding to human CD1a molecules present on, e.g., a cell. For instance, functional variants according to the invention, may have increased or decreased binding affinities for human CD1a compared to the parental binding molecules. Preferably, the amino acid sequences of the variable regions, including, but not limited to, framework regions, hypervariable regions, in particular the CDR3 regions, are modified. Generally, the light chain and the heavy chain variable regions comprise three hypervariable regions, comprising three CDRs, and more conserved regions, the so-called framework regions (FRs). The hypervariable regions comprise amino acid residues from CDRs and amino acid residues from hypervariable loops. Functional variants intended to fall within the scope of the present invention have at least about 50% to about 99%, preferably at least about 60% to about 99%, more preferably at least about 70% to about 99%, even more preferably at least about 80% to about 99%, most preferably at least about 90% to about 99%, in particular at least about 95% to about 99%, and in particular at least about 97% to about 99% amino acid sequence homology with the parental binding molecules as defined herein. Computer algorithms such as inter alia Gap or Bestfit known to a person skilled in the art can be used to optimally align amino acid sequences to be compared and to define similar or identical amino acid residues.

Functional variants can be obtained by altering the parental binding molecules or parts thereof by general molecular biology methods known in the art including, but not limited to, error-prone PCR, oligonucleotide-directed mutagenesis and site-directed mutagenesis.

In yet a further aspect, the invention includes immunoconjugates, i.e., molecules comprising at least one human binding molecule as defined herein and further comprising at least one tag, such as a therapeutic moiety that inhibits or prevents the function of cells and/or causes destruction of cells. Also contemplated in the present invention are mixtures of immunoconjugates according to the invention, or mixtures of at least one immunoconjugates according to the invention, and another molecule, such as a therapeutic agent or another binding molecule or immunoconjugate. In a further embodiment, the immunoconjugates of the invention may comprise more than one tag. These tags can be the same or distinct from each other and can be joined/conjugated non-covalently to the binding molecules. The tags can also be joined/conjugated directly to the binding molecules through covalent bonding, including, but not limited to, disulfide bonding, hydrogen bonding, electrostatic bonding, recombinant fusion and conformational bonding. Alternatively, the tags can be joined/conjugated to the binding molecules by means of one or more linking compounds. Techniques for conjugating tags to binding molecules are well known, see, e.g., Arnon et al., "Monoclonal Antibodies for Immunotargeting of Drugs in Cancer Therapy," p. 243-256 in *Monoclonal Antibodies and Cancer*

*Therapy* (1985), edited by Reisfeld et al., A. R. Liss, Inc.; Hellstrom et al., "Antibodies for Drug Delivery," p. 623-653 in *Controlled Drug Delivery, 2nd edition* (1987), edited by Robinson et al., Marcel Dekker, Inc.; Thorpe, "Antibody Carriers of Cytotoxic Agents," p. 475-506 *In Cancer Therapy: A Review, in Monoclonal Antibodies* 84: *Biological and Clinical Applications* (1985), edited by Pinchera et al.; "Analysis, Results, and Future Prospective of the Therapeutic Use of Radiolabeled Antibody in Cancer Therapy," p. 303-316 in *Monoclonal Antibodies for Cancer Detection and Therapy* (1985), edited by Baldwin et al., Academic Press.

Tags according to the invention include, but are not limited to, toxic substances, radioactive substances, liposomes, enzymes, polynucleotide sequences, plasmids, proteins, peptides or combinations thereof. Toxic substances include, but are not limited to, cytotoxic agents, such as small molecule toxins or chemotherapeutic agents, or enzymatically active toxins of bacterial, fungal, plant or animal origin, or fragments thereof. Examples of cytotoxic agents include, but are not limited to, alkylating agents such as thiotepa and cyclophosphamide; alkyl sulfonate such as busulfan, improsulfan and piposulfan; aziridines such as benzodopa, carboquone, meturedopa, and uredopa; ethylenimines and methylamelamines such as altretamine, triethylenemelamine, trietylenephosphoramide, triethylenethiophosphoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembiehin, phenesterine, prednimustine, trofosfamide, uracil mustard; nitrosoureas such as carmustine, chlorozotocin, fotemustine, lomustine, nimustine, ranimustine; antibiotics such as aclacinomysins, actinomycin, authramycin, azaserine, bleomycin, cactinomycin, calicheamicin, carabicin, carminomycin, carzinophilin, chromoinycins, dactinomycin, daunorubicin, detorubicin, 6-diazo-5-oxo-L-norleucine, doxorubicin, epirubicin, esorubicin, idarubicin, marcellomycin, mitomycin, mycophenolic acid, nogalamycin, olivomycin, peplomycin, potfiromycin, puromycin, quelamycin, rodorubicin, streptonigrin, streptozocin, tubercidin, ubenimex, zinostatin, zorubicin; macrolide antibiotics such as geldanamicin and maytansin, anti-metabolites such as methotrexate and 5-fluorouracil; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; platinum analogs such as cisplatin and carboplatin; triazenes; epipodophyllotoxins; platinum coordination complexes; maytansinoids; and taxoids, such as paclitaxel and doxetaxel. Pharmaceutically acceptable salts, acids or derivatives of any of the above are also included in the present invention. In general, suitable chemotherapeutic agents are described in *Remington's Pharmaceutical Sciences, 18th edition* (1990), edited by A. R. Gennaro, Mack Publishing Co., Philadelphia and in *Goodman and Gilman's The Pharmacological Basis of Therapeutics, 7th edition* (1985), edited by A. G. Gilman, L. S. Goodman, T. W. Rall and F. Murad, MacMillan Publishing Co., New York. Suitable chemotherapeutic agents that are still in the experimental phase are known to those of skill in the art and might also be used as toxic substances in the present invention.

Examples of enzymatically active toxins of bacterial, fungal, plant or animal origin include, but are not limited to, ricin A chain, modeccin A chain, abrin A chain, *Pseudomonas* exotoxin and endotoxin A chain, shiga toxin A, anthrax toxin lethal factor, diphteria A chain, non-binding active fragments of diphtheria toxin, staphylococcal enterotoxin A, the human ribonuclease angiogenin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, tricothecenes, saporin, alpha-sarcin, and fragments or derivatives thereof.

Fusion proteins comprising enzymatically active toxins and binding molecules of the immunoconjugate of the invention can be produced by methods known in the art such as, e.g., recombinantly by constructing nucleic acid molecules comprising nucleotide sequences encoding the human binding molecules in frame with nucleotide sequences encoding the enzymatically active toxin and then expressing the nucleic acid molecules. Alternatively, fusion proteins can be produced chemically by conjugating, directly or indirectly via, for instance, a linker, binding molecules as defined herein to enzymatically active toxins.

Immunoconjugates comprising enzymes may be useful in antibody-directed enzyme-prodrug therapy (ADEPT). In this technique enzymes are conjugated to binding molecules. This conjugation converts the enzymes into inactive prodrugs. The binding molecule-enzyme conjugates are then administered and bind to the binding partner of the binding molecule. After clearance of the conjugates from the circulation, prodrugs are administered, which are converted into active drugs by the enzyme of the conjugates. Passive uptake of the active drugs into the target cells will then occur.

Also contemplated within the present invention are binding molecules of the immunoconjugate of the invention that are labeled with radionuclides. Suitable radionuclides include, but are not limited to, radionuclides that emit alpha radiation such as inter alia $^{212}$bismuth, $^{213}$bismuth and $^{211}$astatine; radionuclides that emit beta radiation such as inter alia $^{131}$iodine, $^{90}$yttrium, $^{186}$rhodium and $^{188}$rhodium; and radionuclides that emit gamma radiation such as inter alia $^{131}$iodine, $^{186}$rhodium and $^{188}$rhodium. Suitable radionuclides further include, but are not limited to, Auger-electron-emitting radionuclides such as inter alia $^{123}$iodine, $^{124}$iodine, $^{125}$iodine, $^{129}$iodine, $^{131}$iodine, $^{111}$indium, $^{77}$bromine, and other radiolabeled halogens. The skilled man will appreciate that other suitable radionuclides can also be identified as suitable in the present invention. The choice of radionuclide will be dependent on many factors such as, e.g., the type of disease to be treated, the stage of the disease to be treated, the patient to be treated and the like. Binding molecules can be attached to radionuclides directly or indirectly via a chelating agent by methods well known in the art.

In another embodiment, the binding molecules of the immunoconjugate of the invention can be conjugated to liposomes to produce so-called immunoliposomes. A liposome may be conjugated to one or more binding molecules, the binding molecules being either the same or different. A variety of methods are available for preparing liposomes. These methods are well known in the art and include, but are not limited to, sonication, extrusion, high pressure/homogenization, microfluidization, detergent dialysis, calcium-induced fusion of small liposome vesicles, and ether-infusion methods. The liposomes may be multilamellar vesicles, but preferably the liposomes are unilamellar vesicles such as small unilamellar (200-500 Å) or large unilamellar vesicles (500-5000 Å). After preparation, the liposomes that have not been sized during formation may be sized by methods known in the art to achieve a desired size range and relatively narrow distribution of liposome sizes. The methods of loading drugs into liposomes are well known to those of skill in the art. The most common methods include the encapsulation technique and the transmembrane potential loading method. In the encapsulation technique, the drugs and liposome components are dissolved in an organic solvent or mixture of solvents in which all species are miscible, and then concentrated to a dry film. A buffer is then added to the dried film and liposomes are formed having the drugs incorporated into the vesicle walls. This method has been described in detail in U.S. Pat. Nos. 4,885,172, 5,059,421, and 5,171,578, the contents of which are incorporated herein by reference. The transmembrane potential loading method has been described in detail in U.S. Pat. Nos. 4,885,172, 5,059,421, 5,171,578, 5,316,771 and 5,380,531, the contents of which are also incorporated herein by reference. As will be understood, the loading techniques are not limited to these two general loading techniques.

The drugs that can be loaded into liposomes include, but are not limited to, the toxic substances mentioned above. Liposomes having loaded different drugs and different liposomes, each liposome having loaded one kind of drug, may be alternative embodiments of liposomes that can be used and these embodiments are therefore also contemplated in the present invention. Human binding molecules of the invention may be attached at the surface of the liposomes or to the terminus of polymers such as polyethylene glycol that are grafted at the surface of the liposomes using conventional chemical-coupling techniques. An advantage of immunoliposomes is the ability to deliver several tens of thousands of drug molecules with a few tens of binding molecules per liposome resulting in high drug to binding molecule ratios. Following binding of the immunoliposomes to the target cells the drug can either, in case of binding molecules that are slowly internalized or not internalized at all, be gradually released from the immunoliposomes and taken up by the cells as a free drug using standard uptake mechanisms or, in case of binding molecules that are rapidly internalized, the immunoliposomes themselves are taken up by the target cells by receptor-mediated endocytosis and the drugs are gradually released within the cells.

In yet another embodiment, the human binding molecules of the invention may be linked to water-soluble, biodegradable polymers, such as, for instance, polymers of hydroxypropylmethacrylamine (HPMA). The polymers have toxic substances linked on separate sites of the polymers with the use of appropriate degradable spacers to allow for release of the toxic substances. The above-described polymers are also called immunopolymers.

In another aspect, the human binding molecules of the invention may be conjugated/attached to one or more antigens. Preferably, these antigens are antigens which are recognized by the immune system of a subject to which the binding molecule-antigen conjugate is administered. The antigens may be identical but may also be different. Conjugation methods for attaching the antigens and binding molecules are well known in the art and include, but are not limited to, the use of cross-linking agents. The human binding molecules will bind to the cells comprising human CD1a and the antigens attached to the binding molecules will initiate a powerful T-cell attack on the conjugate which will eventually lead to the destruction of the cell.

Alternatively, the human binding molecules as described in the present invention can be conjugated to tags and be used for detection and/or analytical and/or diagnostic purposes. The tags used to label the binding molecules for those purposes depend on the specific detection/analysis/diagnosis techniques and/or methods used such as inter alia immunohistochemical staining of tissue samples, flow cytometric detection, scanning laser cytometric detection, fluorescent immunoassays, enzyme-linked immunosorbent assays (ELISAs), radio-immunoassays (RIAs), bioassays (e.g., growth inhibition assays), Western blotting applications, etc. For immunohistochemical staining of tissue samples preferred labels are enzymes that catalyze production and local deposition of a detectable product. Enzymes typically conjugated to binding molecules to permit their immunohistochemical visualization are well known and include, but are not limited to, alkaline phosphatase, P-galactosidase, glucose oxidase, horseradish peroxidase, and urease. Typical substrates for production and deposition of visually detectable products include, but are not limited to, o-nitrophenyl-beta-D-galactopyranoside (ONPG), o-phenylenediamine dihydrochloride (OPD), p-nitrophenyl phosphate (PNPP), p-nitrophenyl-beta-D-galactopryanoside (PNPG), 3', 3'diaminobenzidine (DAB), 3-amino-9-ethylcarbazole (AEC), 4-chloro-1-naphthol (CN), 5-bromo-4-chloro-3-indolyl-phosphate (BCIP), ABTS, BluoGal, iodonitrotetrazolium (INT), nitroblue tetrazolium chloride (NBT), phenazine methosulfate (PMS), phenolphthalein monophosphate (PMP), tetramethyl benzidine (TMB), tetranitroblue tetrazolium (TNBT), X-Gal, X-Gluc, and X-glucoside. Other substrates that can be used to produce products for local deposition are luminescent substrates. For example, in the presence of hydrogen peroxide, horseradish peroxidaze can catalyze the oxidation of cyclic diacylhydrazides such as luminol. Next to that, binding molecules of the immunoconjugate of the invention can also be labeled using colloidal gold or they can be labeled with radioisotopes, such as $^{33}$P, $^{32}$P, $^{35}$S, $^{3}$H, and $^{125}$I. When the binding molecules of the present invention are used for flow cytometric detections, scanning laser cytometric detections, or fluorescent immunoassays, they can usefully be labeled with fluorophores. A wide variety of fluorophores useful for fluorescently labeling the binding molecules of the present invention include, but are not limited to, Alexa Fluor and Alexa Fluor&commat dyes, BODIPY dyes, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Cy2, Cy3, Cy3.5, Cy5, Cy5.5, Cy7, fluorescein isothiocyanate (FITC), allophycocyanin (APC), R-phycoerythrin (PE), peridinin chlorophyll protein (PerCP), Texas Red, fluorescence resonance energy tandem fluorophores such as PerCP-Cy5.5, PE-Cy5, PE-Cy5.5, PE-Cy7, PE-Texas Red, and APC-Cy7. When the binding molecules of the present invention are used for secondary detection using labeled avidin, streptavidin, captavidin or neutravidin, the binding molecules may be labeled with biotin.

Next to that, the human binding molecules of the invention may be conjugated to photoactive agents or dyes such as fluorescent and other chromogens or dyes to use the so obtained immunoconjugates in photoradiation, phototherapy, or photodynamic therapy. The photoactive agents or dyes include, but are not limited to, photofrin. RTM, synthetic diporphyrins and dichlorins, phthalocyanines with or without metal substituents, chloroaluminum phthalocyanine with or without varying substituents, 0-substituted tetraphenyl porphyrins, 3,1-meso tetrakis (o-propionamido phenyl)porphyrin, verdins, purpurins, tin and zinc derivatives of octaethylpurpurin, etiopurpurin, hydroporphyrins, bacteriochlorins of the tetra(hydroxyphenyl) porphyrin series, chlorins, chlorin $e_6$, mono-1-aspartyl derivative of chlorine $e_6$, di-1-aspartyl derivative of chlorin $e_6$, tin(IV) chlorin $e_6$, meta-tetrahydroxyphenylchlor- in, benzoporphyrin derivatives, benzoporphyrin monoacid derivatives, tetracyanoethylene adducts of benzoporphyrin, dimethyl acetylenedicarboxylate adducts of benzoporphyrin, Diels-Adler adducts, monoacid ring "a" derivative of benzoporphyrin, sulfonated aluminum PC, sulfonated AlPc, disulfonated, tetrasulfonated derivative, sulfonated aluminum naphthalocyanines, naphthalocyanines with or without metal substituents and with or without varying substituents, anthracenediones, anthrapyrazoles, aminoanthraquinone, phenoxazine dyes, phenothiazine derivatives, chalcogenapyrylium dyes, cationic selena and tellurapyrylium derivatives, ring-substituted cationic PC, pheophorbide derivative, naturally occurring porphyrins, hematoporphyrin, ALA-induced protoporphyrin IX, endogenous metabolic precursors, 5-aminolevulinic acid benzonaphthoporphyrazines, cationic imminium salts, tetracyclines, lutetium texaphyrin, tin-etio-purpurin, porphycenes, benzophenothiazinium and combinations thereof.

When the immunoconjugates of the invention are used for in vivo diagnostic use, the human binding molecules can also be made detectable by conjugation to e.g., magnetic resonance imaging (MRI) contrast agents, such as gadolinium diethylenetriaminepentaacetic acid, to ultrasound contrast agents or to X-ray contrast agents, or by radio-isotopic labeling.

Furthermore, the human binding molecules or immunoconjugates of the invention can also be attached to solid supports, which are particularly useful for immunoassays or purification of the binding partner. Such solid supports might be porous or nonporous, planar or non-planar and include, but are not limited to, glass, cellulose, polyacrylamide, nylon, polystyrene, polyvinyl chloride or polypropylene supports. The binding molecules can also, for example, usefully be conjugated to filtration media, such as NHS-activated Sepharose or CNBr-activated Sepharose for purposes of immunoaffinity chromatography. They can also usefully be attached to paramagnetic microspheres, typically by biotin-streptavidin interaction. The microspheres can be used for isolation of cells that express or display human CD1a or fragments thereof. As another example, the human binding molecules of the present invention can usefully be attached to the surface of a microtiter plate for ELISA.

Another aspect of the present invention concerns nucleic acid molecules as defined herein encoding human binding molecules of the present invention. In yet another aspect, the invention provides nucleic acid molecules encoding at least the human binding molecules specifically binding to human CD1a. In a preferred embodiment, the nucleic acid molecules are isolated or purified.

The skilled man will appreciate that functional variants of these nucleic acid molecules are also intended to be a part of the present invention. Functional variants are nucleic acid sequences that can be directly translated, using the standard genetic code, to provide an amino acid sequence identical to that translated from the parent nucleic acid molecules. Preferably, the nucleic acid molecules encode human binding molecules containing a CDR3 region, preferably a heavy chain CDR3 region, comprising the amino acid sequence selected from the group consisting of SEQ ID NO:1, SEQ ID NO:2, SEQ ID NO:3, SEQ ID NO:4, SEQ ID NO:5 and SEQ ID NO:6, preferably, the group consists of SEQ ID NO:1 and SEQ ID NO:6. The amino acid sequences of the HCDR1, HCDR2, LCDR1, LCDR2 and LCDR3 regions are shown in Table 3. Nucleic acid molecules encoding human binding molecules containing these CDR regions are also part of the present invention.

Even more preferably, the nucleic acid molecules encode human binding molecules comprising a variable heavy chain comprising the amino acid sequence selected from the group consisting of SEQ ID NO:8, SEQ ID NO:10, SEQ ID NO:12, SEQ ID NO:14, SEQ ID NO:16 and SEQ ID NO:18, preferably, the group consists of SEQ ID NO:8 and SEQ ID NO:18.

In yet another embodiment, the nucleic acid molecules encode binding molecules comprising a variable heavy chain comprising the amino acid sequence of SEQ ID NO:8 and a variable light chain comprising the amino acid sequence of SEQ ID NO:20, or they encode a variable heavy chain comprising the amino acid sequence of SEQ ID NO:10 and a variable light chain comprising the amino acid sequence of SEQ ID NO:20, or they encode a variable heavy chain comprising the amino acid sequence of SEQ ID NO:12 and a variable light chain comprising the amino acid sequence of SEQ ID NO:22, or they encode a variable heavy chain comprising the amino acid sequence of SEQ ID NO:14 and a variable light chain comprising the amino acid sequence of SEQ ID NO:20, or they encode a variable heavy chain comprising the amino acid sequence of SEQ ID NO:16 and a variable light chain comprising the amino acid sequence of SEQ ID NO:20, or they encode a variable heavy chain comprising the amino acid sequence of SEQ ID NO:18 and a variable light chain comprising the amino acid sequence of SEQ ID NO:20.

In a specific embodiment of the invention, the nucleic acid molecules encoding the binding molecules of the invention comprise a nucleotide sequence selected from the group consisting of SEQ ID NO:7, SEQ ID NO:9, SEQ ID NO:11, SEQ ID NO:13, SEQ ID NO:15 and SEQ ID NO:17, preferably, the group consists of SEQ ID NO:7 and SEQ ID NO:17.

In yet another specific embodiment of the present invention, the nucleic acid molecules encoding the binding molecules of the invention comprise the nucleotide sequence of SEQ ID NO:7 and SEQ ID NO:19, the nucleotide sequence of SEQ ID NO:9 and SEQ ID NO:19, the nucleotide sequence of SEQ ID NO:11 and SEQ ID NO:21, the nucleotide sequence of SEQ ID NO:13 and SEQ ID NO:19, the nucleotide sequence of SEQ ID NO:15 and SEQ ID NO:19 or the nucleotide sequence of SEQ ID NO:17 and SEQ ID NO:19.

It is another aspect of the invention to provide vectors, i.e., nucleic acid constructs, comprising one or more nucleic acid molecules according to the present invention. Vectors can be derived from plasmids such as inter alia F, R1, RP1, Col, pBR322, TOL, Ti, etc; cosmids; phages such as lambda, lambdoid, M13, Mu, P1, P22, $Q_\beta$, T-even, T-odd, T2, T4, T7, etc; plant viruses such as inter alia alfalfa mosaic virus, bromovirus, capillovirus, carlavirus, carmovirus, caulivirus, clostervirus, comovirus, cryptovirus, cucumovirus, dianthovirus, fabavirus, fijivirus, furovirus, geminivirus, hordeivirus, ilarvirus, luteovirus, machlovirus, marafivirus, necrovirus, nepovirus, phytorepvirus, plant rhabdovirus, potexvirus, potyvirus, sobemovirus, tenuivirus, tobamovirus, tobravirus, tomato spotted wilt virus, tombusvirus, tymovirus, etc; or animal viruses such as inter alia adenovirus, arenaviridae, baculoviridae, bimaviridae, bunyaviridae, calciviridae, cardioviruses, coronaviridae, corticoviridae, cystoviridae, Epstein-Barr virus, enteroviruses, filoviridae, flaviviridae, Foot-and-Mouth disease virus, hepadnaviridae, hepatitis viruses, herpesviridae, immunodeficiency viruses, influenza virus, inoviridae, iridoviridae, orthomyxoviridae, papovaviruses, paramyxoviridae, parvoviridae, picomaviridae, poliovirus, polydnaviridae, poxviridae, reoviridae, retroviruses, rhabdoviridae, rhinoviruses, Semliki Forest virus, tetraviridae, togaviridae, toroviridae, vaccinia virus, vesicular stomatitis virus, etc. Vectors can be used for cloning and/or for expression of the binding molecules of the invention and might even be used for gene therapy purposes. Vectors comprising one or more nucleic acid molecules according to the invention, operably linked to one or more expression-regulating nucleic acid molecules are also covered by the present invention. The choice of the vector is dependent on the recombinant procedures followed and the host used. Introduction of vectors in host cells can be effected by inter alia calcium phosphate transfection, virus infection, DEAE-dextran-mediated transfection, lipofectamin transfection or electroporation. Vectors may be autonomously replicating or may replicate together with the chromosome into which they have been integrated. Preferably, the vectors contain one or more selection markers. The choice of the markers may depend on the host cells of choice, although this is not critical to the invention as is well known to persons skilled in the art. They include, but are not limited to, kanamycin, neomycin, puromycin, hygromycin, zeocin, thymidine kinase gene from Herpes simplex virus (HSV-TK), dihydrofolate reductase gene from mouse (dhfr). Vectors comprising one or more nucleic acid molecules encoding the binding molecules as described above operably linked to one or more nucleic acid molecules encoding proteins or peptides that can be used to isolate the binding molecules are also covered by the invention. These proteins or peptides include, but are not limited to, glutathione-S-transferase, maltose binding protein, metal-binding polyhistidine, green fluorescent protein, luciferase and beta-galactosidase.

Hosts containing one or more copies of the vectors mentioned above are an additional subject of the present invention. Preferably, the hosts are host cells. Host cells include, but are not limited to, cells of mammalian, plant, insect, fungal or bacterial origin. Bacterial cells include, but are not limited to, cells from Gram-positive bacteria such as several species of the genera *Bacillus, Streptomyces* and *Staphylococcus* or cells of Gram-negative bacteria such as several species of the genera *Escherichia* and *Pseudomonas.* In the group of fungal cells preferably yeast cells are used. Expression in yeast can be achieved by using yeast strains such as inter alia *Pichia pastoris, Saccharomyces cerevisiae* and *Hansenula polymorpha.* Furthermore, insect cells such as cells from Drosophila and Sf9 can be used as host cells. Besides that, the host cells can be plant cells such as inter alia cells from crop plants such as forestry plants, or cells from plants providing food and raw materials such as cereal plants, or medicinal plants, or cells from ornamentals, or cells from flower bulb crops. Transformed (transgenic) plants or plant cells are produced by known methods, for example, Agrobacterium-mediated gene transfer, transformation of leaf discs, protoplast transformation by polyethylene glycol-induced DNA transfer, electroporation, sonication, microinjection or bolistic gene transfer. Additionally, a suitable expression system can be a baculovirus system. Expression systems using mammalian cells such as Chinese Hamster Ovary (CHO) cells, COS cells, BHK cells or Bowes melanoma cells are preferred in the present invention. Mammalian cells provide expressed proteins with posttranslational modifications that are most similar to natural molecules of mammalian origin. Since the present invention deals with molecules that may have to be administered to humans, a completely human expression system would be particularly preferred. Therefore, even more preferably, the host cells are human cells. Examples of human cells are inter alia HeLa, 911, AT1080, A549, 293 and HEK293T cells. Preferred mammalian cells are human embryonal retinoblasts such as 911 cells or the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6™ (PER.C6 is a pending trademark of Crucell Holland B. V.). In preferred embodiments, the human producer cells comprise at least a functional part of a nucleic acid sequence encoding an adenovirus E1 region in expressible format. In even more preferred embodiments, the host cells are derived from a human retina and immortalized with nucleic acids comprising adenoviral E1 sequences, such as the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6™, and derivatives thereof. Production of recombinant proteins in host cells can be performed according to methods well known in the art. The use of the cells marketed under the trademark PER.C6™ as a production platform for proteins of interest has been described in WO 00/63403 the disclosure of which is incorporated herein by reference in its entirety.

In yet another embodiment, human binding molecules of the present invention can also be produced in transgenic, non-human, mammals such as inter alia rabbits, goats or cows, and secreted into, for instance, the milk thereof.

It is another aspect of the invention to provide a method of producing human binding molecules or functional variants thereof according to the present invention. The method comprises the steps of a) culturing a host as described in the present invention under conditions conducive to the expression of the human binding molecules, and optionally, b) recovering the expressed human binding molecules. The expressed human binding molecules can be recovered from the cell free extract, but preferably they are recovered from the culture medium. Methods to recover proteins, such as binding molecules, from cell free extracts or culture medium are well known to the man skilled in the art. Human binding molecules as obtainable by the above-described method are also a part of the present invention.

Alternatively, next to the expression in hosts, such as host cells, the human binding molecules of the invention can be produced synthetically by conventional peptide synthesizers or in cell-free translation systems using RNAs derived from DNA molecules according to the invention. Human binding molecule as obtainable by the above described synthetic production methods or cell-free translation systems are also a part of the present invention.

In yet another alternative embodiment, human binding molecules according to the present invention may be generated by transgenic non-human mammals, such as, for instance, transgenic mice or rabbits, that express human immunoglobulin genes. Preferably, the transgenic non-human mammals have a genome comprising a human heavy chain transgene and a human light chain transgene encoding all or a portion of the human binding molecules as described above. The transgenic non-human mammals can be immunized with a purified or enriched preparation of human CD1a or a fragment thereof and/or cells expressing human CD1a molecules. Protocols for immunizing non-human mammals are well established in the art. See *Using Antibodies: A Laboratory Manual*, edited by E. Harlow, D. Lane (1998), Cold Spring Harbor Laboratory, Cold Spring Harbor, N.Y.; and *Current Protocols in Immunology*, edited by J. E. Coligan, A. M. Kruisbeek, D. H. Margulies, E. M. Shevach, W. Strober (2001), John Wiley & Sons Inc., New York, the disclosures of which are incorporated herein by reference. Immunization protocols often include multiple immunizations, either with or without adjuvants such as Freund's complete adjuvant and Freund's incomplete adjuvant, but may also include naked DNA immunizations. In another embodiment, the human binding molecules are produced by B cells or plasma cells derived from the transgenic animals. In yet another embodiment, the human binding molecules are produced by hybridomas which are prepared by fusion of B cells obtained from the above described transgenic non-human mammals to immortalized cells. B cells, plasma cells and hybridomas as obtainable from the above described transgenic non-human mammals and human binding molecules as obtainable from the above described transgenic non-human mammals, B cells, plasma cells and hybridomas are also a part of the present invention.

In a further aspect, the invention provides a method of identifying human binding molecules according to the invention, or nucleic acid molecules according to the invention, and comprises the steps of a) contacting a phage library of human binding molecules with material comprising human CD1a or a part thereof, b) selecting at least once for a phage binding to the material comprising human CD1a or a part thereof, and c) separating and recovering the phage binding to the material comprising human CD1a or a part thereof. Material comprising human CD1a can be, e.g., cells transfected with human CD1a expression plasmids, isolated human CD1a, the extracellular part of human CD1a, fusion proteins comprising human CD1a or a part thereof, and the like. Phage display methods for identifying and obtaining binding molecules, e.g., antibodies, are by now well-established methods known by the person skilled in the art. They are, e.g., described in U.S. Pat. No. 5,696,108; Burton and Barbas (1994); and de Kruif et al. (1995b). For the construction of phage display libraries, collections of human monoclonal antibody heavy and light chain variable region genes are expressed on the surface of bacteriophage, preferably filamentous bacteriophage, particles in, for example, single chain Fv (scFv) or in Fab format (de Kruif et al., 1995b). Large libraries of antibody fragment-expressing phages typically contain more than $1.0 \times 10^9$ antibody specificities and may be assembled from the immunoglobulin V regions expressed in the B-lymphocytes of immunized- or non-immunized individuals. Alternatively, phage display libraries may be constructed from immunoglobulin variable regions that have been partially assembled in vitro to introduce additional antibody diversity in the library (semi-synthetic libraries). For example, in vitro assembled variable regions contain stretches of synthetically produced, randomized or partially randomized DNA in those regions of the molecules that are important for antibody specificity, e.g., CDR regions. Antigen-specific phage antibodies can be selected from the library by immobilizing target antigens such as human CD1a molecules or fragments thereof on a solid phase and subsequently exposing the target antigens to a phage library to allow binding of phages expressing antibody fragments specific for the solid phase-bound antigen. Non-bound phages are removed by washing and bound phages eluted from the solid phase for infection of *Escherichia coli* (*E. coli*) bacteria and subsequent propagation. Multiple rounds of selection and propagation are usually required to sufficiently enrich for phages binding specifically to the target antigen. Phages may also be selected for binding to complex antigens such as complex mixtures of proteins or whole cells such as cells transfected with human CD1a expression plasmids or cells naturally expressing human CD1a. Selection of antibodies on whole cells has the advantage that target antigens are presented in their native configuration, i.e., unperturbed by possible conformational changes that might have been introduced in the case where an antigen is immobilized to a solid phase. Antigen-specific phage antibodies can be selected from the library by incubating a cell population of interest, expressing known and unknown antigens on their surface, with the phage antibody library to let, for example, the scFv or Fab part of the phage bind to the antigens on the cell surface. After incubation and several washes to remove unbound and loosely attached phages, the cells of interest are stained with specific fluorescent labeled antibodies and separated on a Fluorescent Activated Cell Sorter (FACS). Phages that have bound with their scFv or Fab part to these cells are eluted and used to infect *Escherichia coli* to allow amplification of the new specificity. Generally, one or more selection rounds are required to separate the phages of interest from the large excess of non-binding phages. Monoclonal phage preparations can be analyzed for their specific staining patterns and allowing identification of the antigen being recognized (de Kruif et al., 1995a). The phage display method can be extended and improved by subtracting non-relevant binders during screening by addition of an excess of non-target molecules that are similar, but not identical, to the target, and thereby strongly enhance the chance of finding relevant binding molecules (this process is referred to as the Mabstract® process. Mabstract® is a registered trademark of Crucell Holland B. V., see also U.S. Pat. No. 6,265,150 which is incorporated herein by reference). Alternatively, one or more subtraction steps can be performed before or after screening.

In yet a further aspect, the invention provides a method of obtaining a human binding molecule or a nucleic acid molecule according to the invention, wherein the method comprises the steps of a) performing the above described method of identifying human binding molecules according to the invention, or nucleic acid molecules according to the invention, and b) isolating from the recovered phage the human binding molecule and/or the nucleic acid encoding the human binding molecule. Once a new monoclonal phage antibody has been established or identified with the above mentioned method of identifying human binding molecules or nucleic acid molecules encoding the human binding molecules, the DNA encoding the scFv or Fab can be isolated from the bacteria or phages and combined with standard molecular biological techniques to make constructs encoding bivalent scFvs or complete human immunoglobulins of a desired specificity (e.g., IgG, IgA or IgM). These constructs can be transfected into suitable cell lines and complete human monoclonal antibodies can be produced (Huls et al., 1999; Boel et al., 2000).

In a further aspect, the invention provides compositions comprising at least one human binding molecule, at least one functional variant or fragment thereof, at least one immunoconjugate according to the invention, or a combination thereof. In addition to that, the compositions may comprise inter alia stabilizing molecules, such as albumin or polyethylene glycol, or salts. Preferably, the salts used are salts that retain the desired biological activity of the human binding molecules and do not impart any undesired toxicological effects. Examples of such salts include, but are not limited to, acid addition salts and base addition salts. Acid addition salts include, but are not limited to, those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include, but are not limited to, those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like. If necessary, the binding molecules of the invention may be coated in or on a material to protect them from the action of acids or other natural or non-natural conditions that may inactivate the human binding molecules.

In yet a further aspect, the invention provides compositions comprising at least one nucleic acid molecule as defined in the present invention. The compositions may comprise aqueous solutions such as aqueous solutions containing salts (e.g., NaCl or salts as described above), detergents (e.g., SDS) and/or other suitable components.

Furthermore, the present invention pertains to pharmaceutical compositions comprising at least one human binding molecule according to the invention, at least one functional variant or fragment thereof, at least one immunoconjugate according to the invention, at least one composition according to the invention, or combinations thereof. The pharmaceutical composition of the invention further comprises at least one pharmaceutically acceptable excipient. A pharmaceutical composition according to the invention, can further comprise at least one other therapeutic, prophylactic and/or diagnostic agent.

Typically, pharmaceutical compositions must be sterile and stable under the conditions of manufacture and storage. The human binding molecules, variant or fragments thereof, immunoconjugates, nucleic acid molecules or compositions of the present invention can be in powder form for reconstitution in the appropriate pharmaceutically acceptable excipient before or at the time of delivery. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Alternatively, the human binding molecules, variant or fragments thereof, immunoconjugates, nucleic acid molecules or compositions of the present invention can be in solution and the appropriate pharmaceutically acceptable excipient can be added and/or mixed before or at the time of delivery to provide a unit dosage injectable form. Preferably, the pharmaceutically acceptable excipient used in the present invention is suitable to high drug concentration, can maintain proper fluidity and, if necessary, can delay absorption.

The choice of the optimal route of administration of the pharmaceutical compositions will be influenced by several factors including the physico-chemical properties of the active molecules within the compositions, the urgency of the clinical situation and the relationship of the plasma concentrations of the active molecules to the desired therapeutic effect. For instance, if necessary, the human binding molecules of the invention can be prepared with carriers that will protect them against rapid release, such as a controlled release formulation, including implants, transdermal patches, and microencapsulated delivery systems. Biodegradable, biocompatible polymers can inter alia be used, such as ethylene vinyl acetate, polyanhydrides, polyglycolic acid, collagen, polyorthoesters, and polylactic acid. Furthermore, it may be necessary to coat the human binding molecules with, or co-administer the human binding molecules with, a material or compound that prevents the inactivation of the human binding molecules. For example, the human binding molecules may be administered to a subject in an appropriate carrier, for example, liposomes, or a diluent.

The routes of administration can be divided into two main categories, oral and parenteral administration. These two categories include, but are not limited to, bolus, buccal, epidermal, epidural, inhalation, intra-abdominal, intra-arterial, intra-articular, intrabronchial, intracapsular, intracardiac, intracartilaginous, intracavitary, intracelial, intracelebellar, intracerebronventricular, intracolic, intracervical, intradermal, intragastric, intrahepatic, intramedullary, intramuscular, intramyocardial, intranasal, intra-ocular intra-orbital, intraosteal, intrapelvic, intrapericardiac, intraperitoneal, intraplaque, intrapleural, intraprostatic, intrapulmonary, intrarectal, intrarenal, intraretinal, intraspinal, intrastemal, intrasynovial, intrathecal, intrathoracic, intratumoral, intrauterine, intravenous, intraventricular, intravesical, rectal, spinal, subarachnoid, subcapsular, subcutaneous, subcuticular, sublingual, topical, transdermal, transmucosal, transtracheal, and vaginal administration. The preferred administration route is intravenous.

Oral dosage forms can be formulated inter alia as tablets, troches, lozenges, aqueous or oily suspensions, dispersible powders or granules, emulsions, hard capsules, soft gelatin capsules, syrups or elixirs, pills, dragees, liquids, gels, or slurries. These formulations can contain pharmaceutically excipients including, but not limited to, inert diluents such as calcium carbonate, sodium carbonate, lactose, calcium phosphate or sodium phosphate; granulating and disintegrating agents such as corn starch or alginic acid; binding agents such as starch, gelatin or acacia; lubricating agents such as calcium stearate, glyceryl behenate, hydrogenated vegetable oils, magnesium stearate, mineral oil, polyethylene glycol, sodium stearyl, fumarate, stearic acid, talc, zinc stearate; preservatives such as n-propyl-p-hydroxybenzoate; coloring, flavoring or sweetening agents such as sucrose, saccharine, glycerol, propylene glycol or sorbitol; vegetable oils such as arachis oil, olive oil, sesame oil or coconut oil; mineral oils such as liquid parrafin; wetting agents such as benzalkonium chloride, docusate sodium, lecithin, poloxamer, sodium lauryl sulfate, sorbitan esters; and thickening agents such as agar, alginic acid, beeswax, carboxymethyl cellulose calcium, carageenan, dextrin or gelatin.

The pharmaceutical compositions of the present invention can also be formulated for parenteral administration. Formulations for parenteral administration can be inter alia in the form of aqueous or non-aqueous isotonic sterile non-toxic injection or infusion solutions or suspensions. Preferred parenteral administration routes include intravenous, intraperitoneal, epidural, intramuscular and intratumoral injection or infusion. The solutions or suspensions may comprise agents that are non-toxic to recipients at the dosages and concentrations employed such as 1,3-butanediol, Ringer's solution, Hank's solution, isotonic sodium chloride solution, oils such as synthetic mono- or diglycerides or fatty acids such as oleic acid, local anesthetic agents, preservatives, buffers, viscosity or solubility increasing agents, water-soluble antioxidants such as ascorbic acid, cysteine hydrochloride, sodium bisulfate, sodium metabisulfite, sodium sulfite and the like, oil-soluble antioxidants such as ascorbyl palmitate, butylated hydroxyanisole (BHA), butylated hydroxytoluene (BHT), lecithin, propyl gallate, alpha-tocopherol, and the like, and metal chelating agents, such as citric acid, ethylenediamine tetraacetic acid (EDTA), sorbitol, tartaric acid, phosphoric acid, and the like.

The human binding molecules according to the invention, the variants or fragments thereof, the immunoconjugates according to the invention, the nucleic acid molecules according to the invention, the compositions according to the invention, or the pharmaceutical compositions according to the invention, can be used as medicaments. They can inter alia be used in the diagnosis, prevention, treatment, or combination thereof, of a neoplastic disorder or disease. Preferably, the neoplastic disorder or disease is selected from the group consisting of acute myeloid leukemia (AML), chronic myeloid leukemia (CML), chronic myelogenous leukemia in blast crisis (CML-BC), chronic myelomonocytic leukemia, acute promyelocytic leukemia, myelodysplastic syndrome, juvenile myelomonocytic leukemia, acute lymphoblastic leukemia (ALL), acute non-lymphocytic leukemia (ANLL), T-cell acute lymphoblastic leukemia (T-ALL), large granular lymphocytic leukemia (LGLL), B-cell chronic lymphocytic leukemia (B-CLL) and Langerhans cell histiocytosis. The human binding molecules of the invention are suitable for treatment of yet untreated patients suffering from any of the above disorders and diseases, patients who have been or are treated and are in remission or are not in remission, and patients with a recurrent/refractory diseases or disorders. Other potential applications wherein the above-mentioned molecules and compositions could be used can be envisaged. First, they could be used to selectively regulate dendritic cell-mediated immune responses. In this regard, the identification of a critical role for Langerhans cells in sustaining survival and proliferation of cutaneous T cell lymphoma represents an intriguing model in which to test such molecules and compositions. Another potentially important application of the molecules and compositions would be in the abrogation of Graft-vs-Host Disease (GVHD), as it has been shown that depletion of Langerhans cells in a host significantly reduces or eliminates GVHD in murine models. This approach may also be applicable in patients receiving allogeneic hematopoetic stem cell transplants. Lastly, the use of antigen delivery to Langerhans cells by the molecules and compositions has immense potential for augmenting vaccine efficacy, including cancer vaccines.

The above-mentioned molecules or compositions may be employed in conjunction with other molecules useful in diagnosis, prevention and/or treatment. They can be used in vitro, ex vivo or in vivo. The molecules are typically formulated in the compositions and pharmaceutical compositions of the invention in a therapeutically or diagnostically effective amount. Dosage regimens can be adjusted to provide the optimum desired response (e.g., a therapeutic response). For example, a single bolus may be administered, several divided doses may be administered over time or the dose may be proportionally reduced or increased as indicated by the exigencies of the therapeutic situation. The molecules and compositions according to the present invention are preferably sterile. Methods to render these molecules and compositions sterile are well known in the art. The other molecules useful in diagnosis, prevention and/or treatment can be administered in a similar dosage regimen as proposed for the human binding molecules of the invention. If the other molecules are administered separately, they may be administered to a subject with a neoplastic disorder or disease prior (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks before) to, concomitantly with, or subsequent (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks after) to the administration of one or more of the human binding molecules or pharmaceutical compositions of the invention. The dosing regimen is usually sorted out during clinical trials in human patients.

Human binding molecules and pharmaceutical compositions comprising the human binding molecules are particularly useful, and often preferred, when to be administered to human beings as in vivo diagnostic or therapeutic agents, since recipient immune response to the administered antibody will often be substantially less than that occasioned by administration of a monoclonal murine, chimeric or humanized binding molecule.

Alternatively, cells that are genetically engineered to express the human binding molecules of the invention are administered to patients in vivo. Such cells may be obtained from an animal or patient or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the nucleic acid molecules of the invention into the cells. Preferably, the human binding molecules are secreted from the cells. The engineered cells which express and preferably secrete the human binding molecules as described herein can be introduced into the patient, for example, systemically, e.g., in the circulation, or intraperitoneally. In other embodiments, the cells can be incorporated into a matrix or can be encapsulated and implanted in the body. In a gene therapy setting the human binding molecules may be administered in the form of a vector capable of infecting cells of the host, coding for a human binding molecule according to the invention.

In another aspect, the invention concerns the use of human binding molecules, fragments or variants thereof, immunoconjugates according to the invention, nucleic acid molecules according to the invention, compositions or pharmaceutical compositions according to the invention, in the preparation of a medicament for the diagnosis, prophylaxis, treatment, or combination thereof, of a neoplastic disorder or disease. The neoplastic disease or disorder is preferably selected from the group described above.

Next to that, kits comprising at least one human binding molecule according to the invention, at least one variant or fragment thereof, at least one immunoconjugate according to the invention, at least one nucleic acid molecule according to the invention, at least one composition according to the invention, at least one pharmaceutical composition according to the invention, at least one vector according to the invention, at least one host according to the invention, or a combination thereof are also a part of the present invention. Optionally, the above-described components of the kits of the invention are packed in suitable containers and labeled for diagnosis, prevention and/or treatment of the indicated conditions. The above-mentioned components may be stored in unit or multi-dose containers, for example, sealed ampules, vials, bottles, syringes, and test tubes, as an aqueous, preferably sterile, solution or as a lyophilized, preferably sterile, formulation for reconstitution. The containers may be formed from a variety of materials such as glass or plastic and may have a sterile access port (for example, the container may be an intravenous solution bag or a vial having a stopper pierceable by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. Associated with the kits can be instructions customarily included in commercial packages of therapeutic, prophylactic and/or diagnostic products, that contain information about, for example, the indications, usage, dosage, manufacture, administration, contraindications and/or warnings concerning the use of such therapeutic, prophylactic and/or diagnostic products.

In a further aspect, the invention provides a method of detecting human CD1a or a variant or part thereof, wherein the method comprises the steps of a) contacting a sample with a diagnostically effective amount of a human binding molecule of the invention or a functional variant or fragment thereof or an immunoconjugate according to the invention, and b) determining whether the human binding molecule or functional variant or fragment thereof or immunoconjugate specifically binds to a compound of the sample. Methods of detection are known in the art and include, but are not limited to, Western Blot, RIA, ELISA, and immunohistochemical methods.

EXAMPLES

Example 1

In vitro Generation of Dendritic Cells

Cultured dendritic cells (DCs) were obtained by the isolation of monocytes from buffycoats, using Ficoll density gradient centrifugation for granulocyte removal, sheep red blood cell-rosetting (SRBC-rosetting) for T-cell removal, and plastic adherence for two hours at 37° C. to remove other cells and obtain monocytes. The obtained monocytes were cultured for five days in the presence of GM-CSF and IL-4 to differentiate them into immature DCs (mainly characterized by a CD1a$^+$/CD83$^-$ phenotype). A further incubation of two days in the presence of a cocktail of GM-CSF, IL-4, PGE2, IL-1β, IL-6 and TNF-α resulted in the development of mature DCs (mainly characterized by a CD1a$^+$/CD83$^+$ phenotype) (Jonuleit et al., 1997) (eee FIG. 1).

Example 2

Selection of Phage Antibodies Carrying Single Chain Fv Fragments on Dendritic Cells by Cell Sorting After five and seven days of culture, about 1.5×10$^7$ immature and mature monocyte-derived DCs, respectively, were obtained from the tissue culture flasks and mixed with 0.5 ml of a semi-synthetic phage scFv antibody display library. This library of human single chain antibody fragments was constructed as described in de Kruif et al. (1995b). In short, the library consisted of a combination of 49 germline VH genes fused with ~10$^8$ synthetic heavy chain CDR3 regions and seven light chains. The CDR3 regions varied in length between six and 15 amino acids. The light chains were encoded by members of the Vκ1 to Vκ4 and Vλ1 to Vλ3 families. The final library comprised about 4×10$^8$ individual clones.

0.5 ml of the above library containing approximately 10$^{13}$ phage particles per ml was blocked at 4° C. for 15 minutes in RPMI-medium containing 20% fetal calf serum and 5 mM EDTA. After that, about 1.5×10$^7$ immature DCs or about 7.3×10$^6$ mature DCs were added to the blocked library in the presence of about 7.5×10$^7$ fresh peripheral blood leucocytes (PBL) acting as subtractor cells in a final volume was 5 ml. This mixture was slowly rotated overnight at 4° C. The next day, the cells were washed twice with 50 ml ice-cold RPMI-medium containing 20% fetal calf serum and 5 mM EDTA and were stained with 100 µl PE-conjugated anti-CD83 antibody (BD PharMingen) and 100 µl FITC-conjugated anti-CD1a antibody (BD PharMingen) to visualize the dendritic cell populations on a flow cytometer. These antibodies did not recognize PBL and therefore a pure population of DC was obtained. After an incubation of one hour on ice, the cells were washed once with 15 ml of the above medium and resuspended in 4 to 6 ml of the medium. Just before sorting, cells were separated with a cell strainer (BD). Cell sorting was performed on a FACStar$^{PLUS}$ fluorescence activated cell sorter with the gates set around the CD83$^-$CD1a$^+$ immature or CD83$^+$CD1a$^+$ mature DCs. For each cell population, 10$^4$ to 10$^5$ cells with phages still attached were sorted.

To elute specifically bound phages, the cells were pelleted for ten minutes at 1200 rpm. Thereafter, they were resuspended in a volume of 100 µl of the obtained supernatant and brought in a 50 ml tube containing 150 µl of 76 mM sodium citrate. After ten minutes at room temperature, the pH was neutralized by adding 200 µl of 1 M Tris-HCl buffer (pH 7.4). Finally, 1 ml of 2TY medium and 1 ml of log phase *Escherichia coli* XL-1 blue were added. Infection was allowed to proceed for 30 minutes at 37° C. Next, the bacteria were centrifuged at 2800 rpm for ten minutes, suspended in 0.5 ml of 2TY, and plated on agar plates containing 25 µg/ml tetracycline, 100 µg/ml ampicillin, and 5% glucose. After overnight culture at 37° C., the plates were scraped and bacteria were frozen in stock vials or used to prepare the next restricted library, using VCSM13 helper phage. After the first round of selection 7.6×10$^4$ and 2.5×10$^4$ colonies were obtained from the selection with mature and immature DCs, respectively.

The selection round described above was repeated two more times, with the proviso that after both the second and the third round bacteria were seeded in the proper dilution allowing isolation of single colonies. The twenty single clones obtained were individually grown and rescued with VCSM13 helper phage to prepare phage antibody solutions. Next, each of the twenty clones obtained was tested for specific binding to the immature and mature DC population (see upper panels of FIG. 2 for binding of the representative single chain phage antibody called SC02-113 to immature and mature DCs).

Example 3

Identification of CD1a as the Antigen Recognized by the Selected scFv Phage Antibodies In total, three selection rounds were performed and after both the second and third round, phage antibodies were tested for specific binding on a variety of cell-types, i.e., cultured DCs, PBLs, tonsil and synovial fluid cell suspensions, several cell lines including K562, U266, IM9, U937, THP, CEM, Fravel, HL60, Raji, RPMI8226, HepgII, HELA, HT29 and Jurkatt, a C1R cell line transfected with the molecule CD1a, and A431 cell lines transfected with the molecules CD80, CD83, and CD86. For staining of cells, 100 µl of the phage antibodies were blocked by adding 50 µl of PBS containing 4% milk powder for 15 minutes at room temperature. Next, 5×10$^5$ cells in 50 µl of PBS containing 1% BSA were added to the blocked phage antibodies and the mixture obtained was incubated on ice for one hour. After that, the obtained mixture was washed three times with 200 µl PBS containing 1% BSA. To detect cell-bound phage antibodies, the cells were incubated with 20 µl of a 1:800 dilution of sheep anti-M13 polyclonal antibody for 20 minutes on ice. Thereafter, the cells were washed with PBS containing 1% BSA and incubated with 20 µl of a 1:700 dilution of PE-conjugated donkey anti-sheep polyclonal antibody for 20 minutes on ice.

To visualize DCs the cells were washed again with PBS containing 1% BSA, stained with 10 µl 1:10 diluted FITC-conjugated anti-CD1a antibody (BD PharMingen) and suspended in 200 µl of PBS containing 1% BSA. Flow cytometric analyses were performed using a FACScan (Becton Dickinson).

Figure 2:
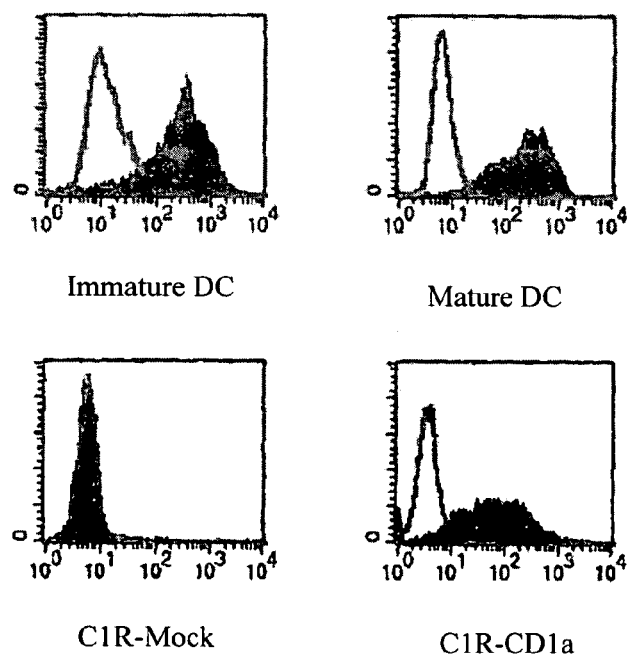
FIG. 2. FACS analysis of the binding of a representative monoclonal phage antibody (called SC02-113) to cultured immature (top, left) and mature (top, right) DCs and a CD1a transfectant in C1R cells (bottom, right), compared with the C1R mock-transfected negative control (bottom, left).

The twenty scFv phage antibodies derived from the selections described above bound exclusively to the cell line transfected with CD1a (see lower right panel of FIG. 2 for binding of the representative scFv phage antibody called SC02-113 to the CD1a-transfected cell line). The C1R cells transfected with vector containing a CD1a insert were clearly positive, whereas the C1R cell line transfected with vector without CD1a insert (mock-transfected) was negative after staining with the phage antibodies (see lower left panel of FIG. 2 for binding of the representative scFv phage antibody called SC02-113 to the mock-transfected cell line). The A431 cell lines transfected with CD80, CD83 and CD86 were negative after staining with the phage antibodies (data not shown).

Example 4

Characterization of the Human CD1a-specific scFvs

From the twenty phage antibody (scFv) clones that bound exclusively to the cell line transfected with human CD1a, plasmid DNA was obtained and nucleotide sequences were determined according to standard techniques. In short, the nucleotide sequence of the VH and VL of all twenty clones was determined using primer M13REV (5'-AACAGCTAT-GACCATG (SEQ ID NO:23)) and fdSeq (5'-GAATTTTCT-GTATGAGG (SEQ ID NO:24)) in a sequence reaction with the Taq sequencing kit with the following cycling protocol (25 cycles): 94° C. for ten seconds (denaturing), 50° C. for five seconds (annealing) and 60° C. for four minutes (extension). Precipitated DNA was dissolved in sample buffer, run and analyzed on an ABIPRISM automated fluorescent sequencer. The obtained nucleotide sequences were compared to the VBASE database which is well known to the average skilled person in the art of antibodies and the gene family of each individual chain was determined. The twenty clones turned out to contain six different scFvs. These were named SC02-113, SC02-114, SC02-115, SC02-116, SC02-117 and SC02-118, respectively (see Table 1). The nucleotide sequences of the scFvs called SC02-113, SC02-114, SC02-115, SC02-116, SC02-117 and SC02-118 are shown in SEQ ID NO:25, SEQ ID NO:27, SEQ ID NO:29, SEQ ID NO:31, SEQ ID NO:33 and SEQ ID NO:35, respectively (see Table 1). The amino acid sequences of the scFvs called SC02-113, SC02-114, SC02-115, SC02-116, SC02-117 and SC02-118 are shown in SEQ ID NO:26, SEQ ID NO:28, SEQ ID NO:30, SEQ ID NO:32, SEQ ID NO:34 and SEQ ID NO:36, respectively (see Table 1). The VH and VL gene identity and heavy chain CDR3 sequences of the human CD1a-specific scFvs are also depicted in Table 1.

Example 5

Construction of Fully Human Immunoglobulin Molecules (Human Monoclonal Anti-CD1a Antibodies) from the Selected Anti-CD1a Single Chain Fvs Heavy and light chain variable regions of the scFvs called SC02-113, SC02-114, SC02-115, SC02-116, SC02-117 and SC02-118 were PCR-amplified using oligonucleotides to append restriction sites and/or sequences for expression in the IgG expression vectors pSyn-C03-HCγ1 (see SEQ ID NO:37) pSyn-C05-Cκ (see SEQ ID NO:38) and pSyn-C04-Cλ (see SEQ ID NO:39). The heavy chain variable regions of the scFvs called SC02-113, SC02-114, SC02-115, SC02-116, SC02-117 and SC02-118 were cloned into the vector pSyn-C03-HCγ1; the shared light chain variable region of the scFvs called SC02-113, SC02-114, SC02-116, SC02-117 and SC02-118 was cloned into the vector pSyn-C05-Cκ; the light chain variable region of the scFv called SC02-115 was cloned into the vector pSyn-C04-Cλ The VL gene shared between scFvs SC02-113, SC02-114, SC02-116, SC02-117 and SC02-118 was first amplified using oligonucleotides 5K-I (SEQ ID NO:40) and sy3K-C (SEQ ID NO:41) (see below) and the PCR products cloned into vector pSyn-C05-Cκ. The VL gene for scFv SC02-115 was first amplified using oligonucleotides sy5L-A (SEQ ID NO:42) and 3L-B (SEQ ID NO:43) (see below) and the PCR product cloned into vector pSyn-C04-Cκ Nucleotide sequences for all constructs were verified according to standard techniques known to the skilled artisan.

VH genes were first amplified using the following oligonucleotide sets: SC02-113, 5H-Fshort (SEQ ID NO:44) and sy3H-A (SEQ ID NO:45); SC02-114, SC02-116 and SC02-117, 5H-B (SEQ ID NO:46) and sy3H-A (SEQ ID NO:45); SC02-118, 5H-B**65 (SEQ ID NO:47) and sy3H-A (SEQ ID NO:45); SC02-115; First 5H-A (SEQ ID NO:48) and 115int68 (SEQ ID NO:49), and then the PCR product obtained was re-amplified with the primers 5H-A (SEQ ID NO:48) and sy3H-A (SEQ ID NO:45). Thereafter, the PCR products were cloned into vector pSyn-C03-HCγ1 and nucleotide sequences were verified according to standard techniques known to the skilled person in the art.

```
                                          (SEQ ID NO: 47)
5H-B**   Acctgtcttgaattctccatggccgaggtgcagctggtgga
65       gtctggggaggcttggtacatcc (SEQ ID NO: 46)
5H-B     Acctgtcttgaattctccatggccgaggtgcagctggtgga
         gtctg (SEQ ID NO: 49)
115int   Caccagggtgccctggcccagtagtcaaagtaactcggca
68       tctgcgaccttgcacagtaatacacgg (SEQ ID NO: 48)
5H-A     Acctgtcttgaattctccatggcccaggtgcagctggtgca
         gtctgg (SEQ ID NO: 44)
5H-F-    Acctgtcttgaattctccatggcccaggtgcagctgcagga
short    gtccggcc (SEQ ID NO: 45)
sy3H-A   Gcccttggtgctagcgctggagacggtcaccagggtgccct
         ggcccc (SEQ ID NO: 40)
5K-I     Acctgtctcgagttttccatggctgacatccagatgaccca
         gtctccatcctcc (SEQ ID NO: 41)
sy3K-C   Gggaccaaggtggagatcaaacggaccgtggccgcccccagc (SEQ ID NO: 42)
sy5L-A   Acctgtctcgagttttccatggcttcctccgagctgaccca
         ggaccctgctg (SEQ ID NO: 43)
3L-B     Ttttccttagcggccgcgactcacctaggacggtcagcttg
         gtc
```

The resulting expression constructs pgG102-113C03, pgG102-114C03, pgG102-115C03, pgG102-116C03, pgG102-117C03 and pgG102-118C03 (the deposits of which having accession numbers 03102801, 03102802, 03102803, 03102804, 03102805 and 03102806) encoding the anti-CD1a human IgG1 heavy chains were transiently expressed in combination with the pSyn-C05-VkI construct (the deposit of which has accession number 03102807), except for construct pgG102-115C03 which was transfected with the pSyn-C04-V13 construct (the deposit of which has accession number 03102808), encoding the light chains in 293T cells and supernatants containing IgG1 antibodies were obtained. The nucleotide sequences of the heavy chains of the antibodies called 02-113, 02-114, 02-115, 02-116, 02-117 and 02-118 (the antibodies are herein also called CR2113, CR2114, CR2115, CR2116, CR2117 and CR2118, respectively) are shown in SEQ ID NOS:50, 52, 54, 56, 58 and 60, respectively. The amino acid sequences of the heavy chains of the antibodies called 02-113, 02-114, 02-115, 02-116, 02-117 and 02-118 (the antibodies are herein also called CR2113, CR2114, CR2115, CR2116, CR2117 and CR2118, respectively) are shown in SEQ ID NOS:51, 53, 55, 57, 59 and 61, respectively.

The nucleotide sequences of the light chain of antibodies 02-113, 02-114, 02-116, 02-117 and 02-118 is shown in SEQ ID NO:62 and of antibody 02-115 in SEQ ID NO:64. The amino acid sequences of the light chain of antibodies 02-113, 02-114, 02-116, 02-117 and 02-118 is shown in SEQ ID NO:63 and of antibody 02-115 in SEQ ID NO:65. Subsequently, the antibodies were purified over protein-A columns and size-exclusion columns using standard purification methods used generally for immunoglobulins (see, for instance, WO 00/63403).

The human anti-CD1a IgG1 antibodies were validated for their ability to bind to CD1a transfected cell lines essentially as described for scFvs (see Example 3). The purified anti-CD1a antibodies were diluted to various concentrations (depicted in the figures) and detected with mouse anti-human $IgG_\kappa$ labeled with FITC or FITC-labeled streptavidin in the case of biotinylated human anti-CD1a antibodies. In addition to the cell lines C1R-CD1a and C1R mock transfected described in Example 3, the cell lines C1R-CD1b, C1R-CD1c, C1R-CD1d and B16-CD1a and B16 mock transfected were tested. Each staining was repeated three times and compared to the negative control irrelevant isotype control antibody called CR2027 using the Kolmogorov-Simov test. To calculate K-S statistics, an overlay of histograms of isotype control antibody and anti-CD1a antibody was made. The log shift between the peaks of the histograms was determined and used to calculate the D-value. The greater the log shift of the anti-CD1a antibody response peak from the isotype control antibody response peak, the larger the D-value.

Figure 3:
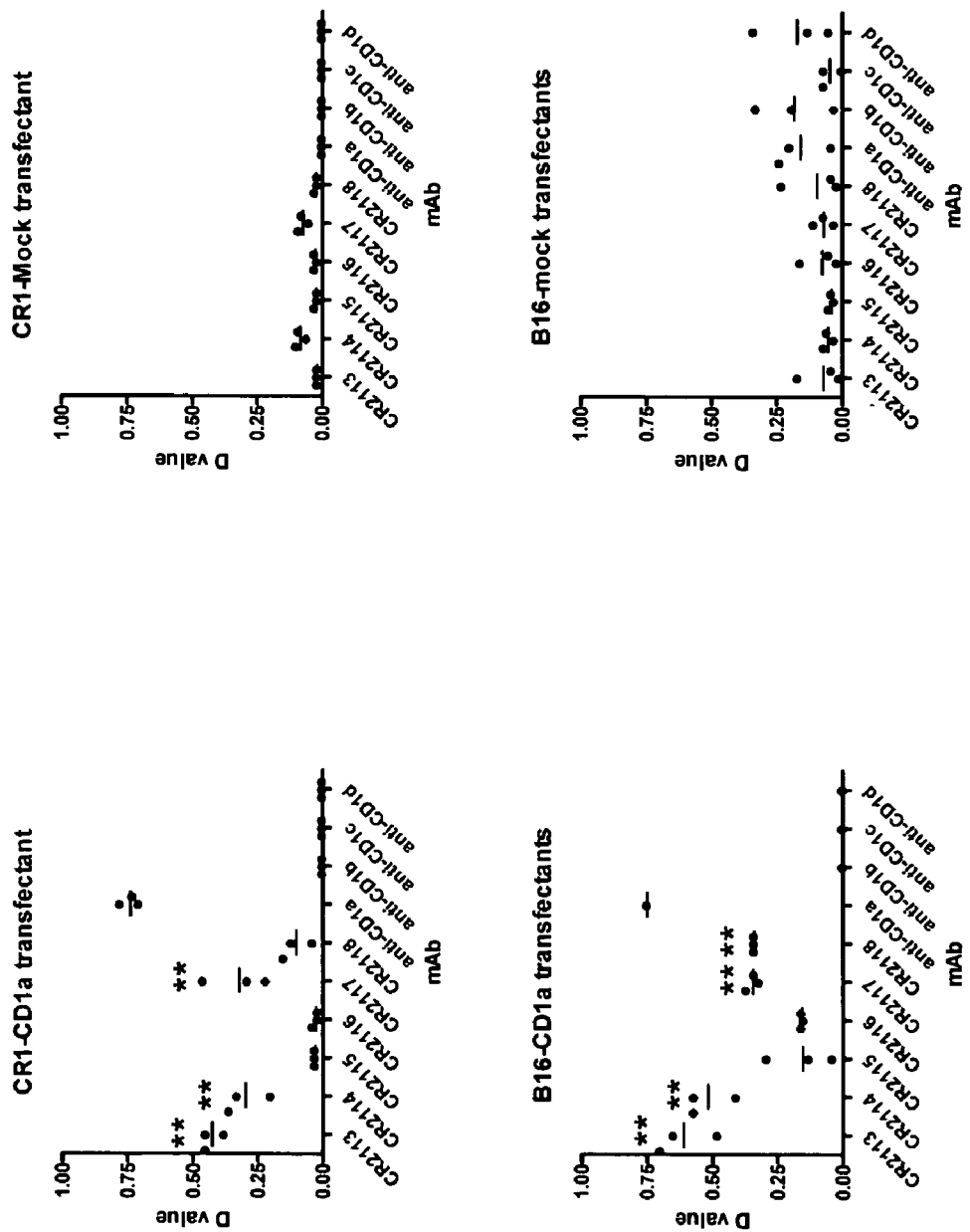
FIG. 3. Binding of the human anti-human CD1a monoclonal antibodies called CR2113, CR2114, CR2115, CR2116, CR2117 and CR2118 and commercially available mouse anti-human CD1a antibodies, mouse anti-human CD1b antibodies, mouse anti-human CD1c antibodies and mouse anti-human CD1d antibodies to CR1-CD1a and B16-CD1a transfectants and CR1 and B16 mock transfectants. Significant binding of human anti-human CD1a monoclonal antibodies to CD1a transfectants compared to mock transfectants is indicated with **. Significance was tested with an unpaired two-tailed t-test (p<0.05).

After conversion to full IgG all six antibodies bound to the B16-CD1a transfectant at a concentration of 10 µg/ml, however only four of the six, i.e., the antibodies called CR2113, CR2114, CR2117, CR2118 bound to the C1R-CD1a transfectant (see FIG. 3, figures on the left side). None of the antibodies bound significantly to the C1R or B16 mock transfected (see FIG. 3, figures on the right side).

Figure 4:
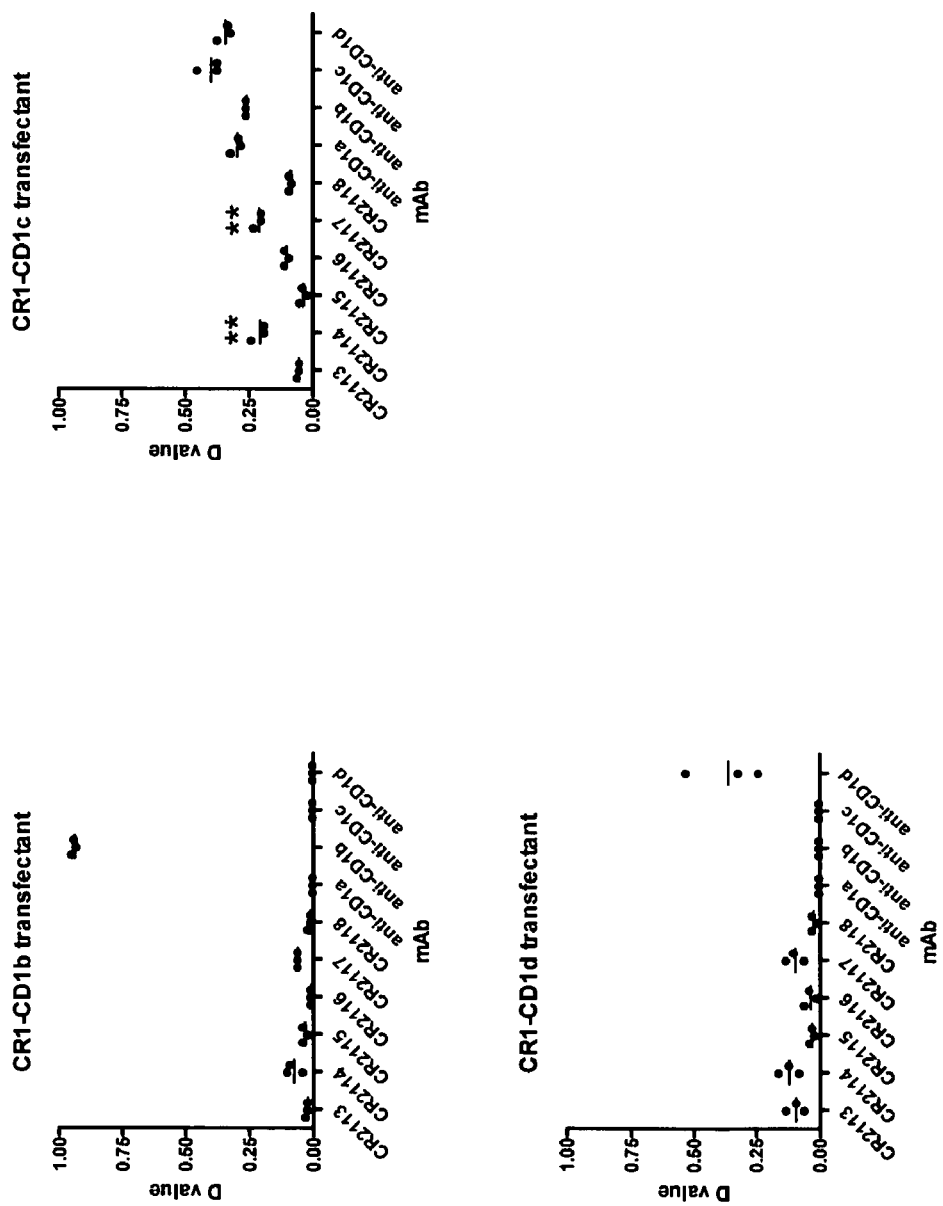
FIG. 4. Binding of the human anti-human CD1a monoclonal antibodies called CR2113, CR2114, CR2115, CR2116, CR2117 and CR2118 and commercially available mouse anti-human CD1a antibodies, mouse anti-human CD1b antibodies, mouse anti-human CD1c antibodies and mouse anti-human CD1d antibodies to CR1-CD1b , CR1-CD1c and CR1-CD1d transfectants. Significant binding of human anti-human CD1a monoclonal antibodies to the CR1-CD1b , CR1-CD1c or CR1-CD1d transfectants compared to CR1 mock transfectants is indicated with **. Significance was tested with an unpaired two-tailed t-test (p<0.05).
Figure 5A:
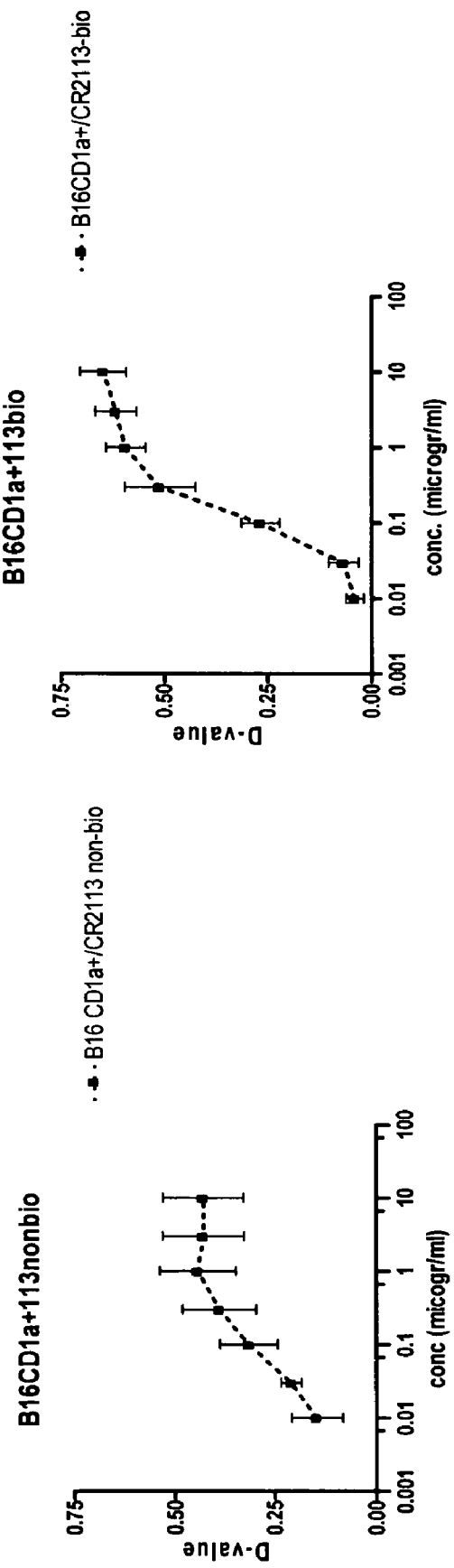
FIGS. 5A-D show binding curves of unlabeled and biotin labeled human anti-human CD1a monoclonal antibodies called CR2113, CR2114, CR2117 and CR2118 on B16-CD1a transfectants.
Figure 5B:
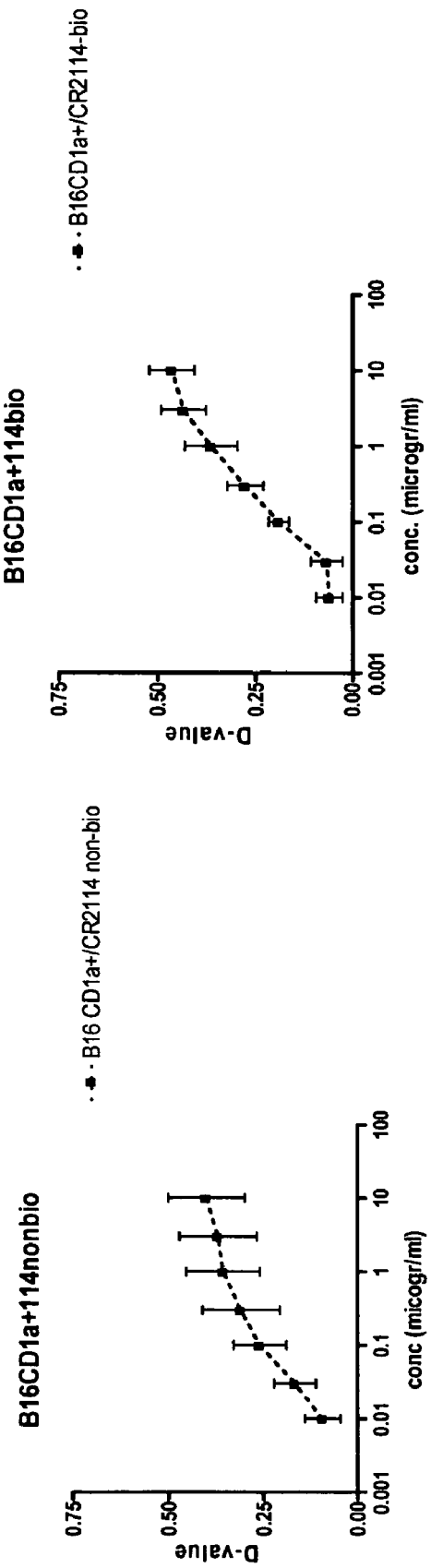
Figure 5C:
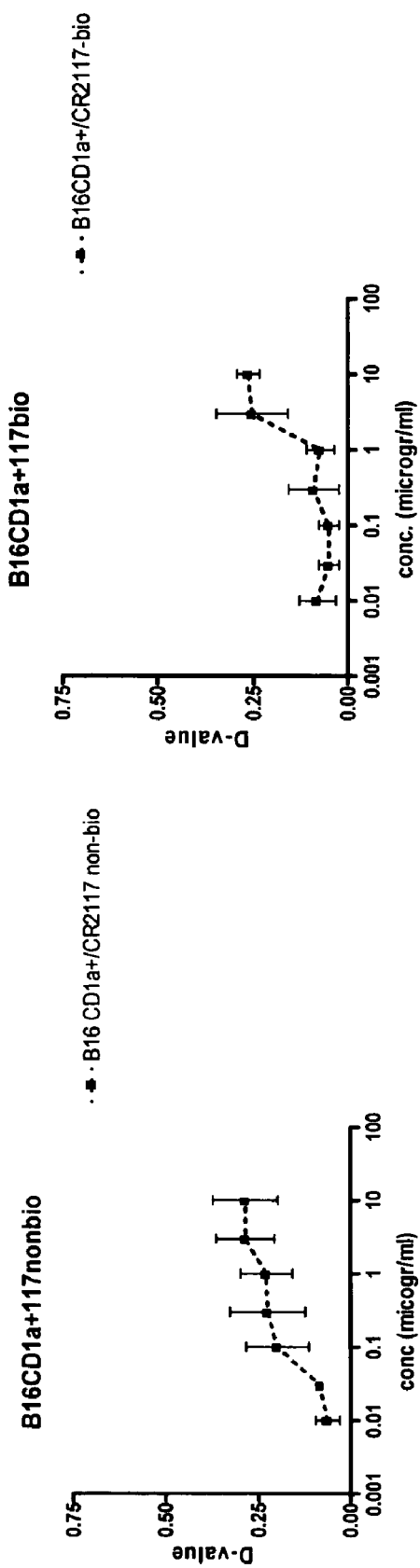
Figure 5D:
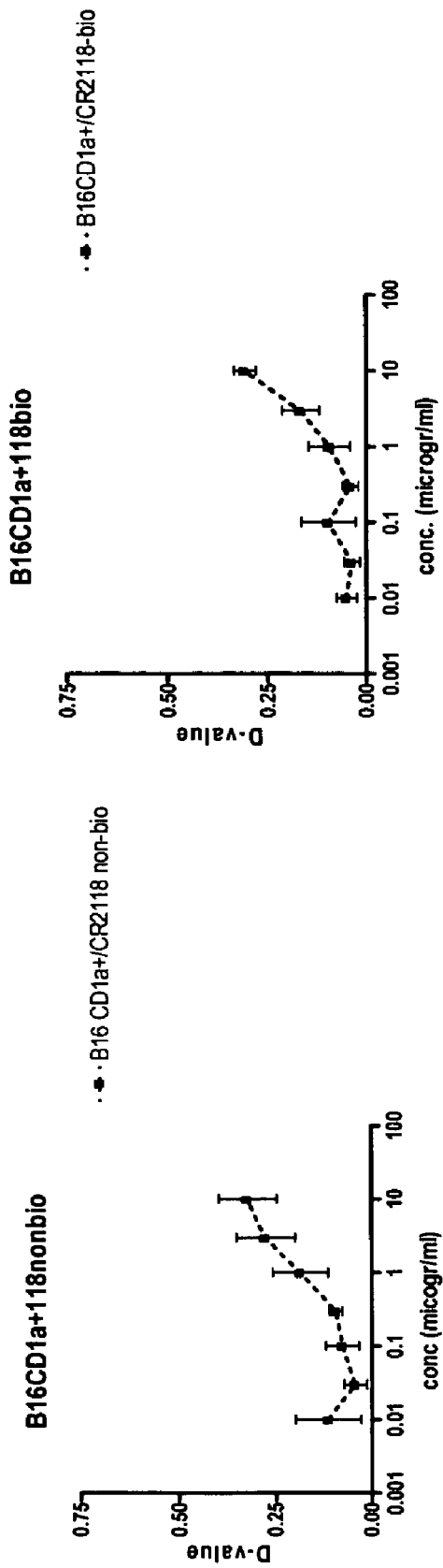

No specific staining of any of the six human anti-CD1a monoclonal antibodies was detected on the C1R-CD1b or C1R-CD1d transfectants (see FIG. 4). Slight, but significant, staining ($p<0.05$) was detected for the two antibodies CR2114 and CR2117 on C1R-CD1c transfectants (see FIG. 4). The results demonstrate the binding specificity of the antibodies for human CD1a, even among the highly conserved human CD1 family of genes. In addition, staining was also carried out on freshly prepared mouse thymocytes, which express murine CD1a and CD1d at low levels. No specific staining for any of the six human anti-CD1a monoclonal antibodies was observed demonstrating species specificity of the antibodies (see Table 2).

Binding curves were generated for the antibodies CR2113, CR2114, CR2117 and CR2118 by measuring binding on B16-CD1a transfected cells with FACS as above using the concentrations of antibody ranging from 0.01 to 10 µg/ml. Both unlabeled and biotinylated antibodies were used and the pattern of staining was indistinguishable between the two forms (see FIGS. 5A-D). CR2113 showed saturation of binding at 1 µg/ml, CR2114 was not saturated at 10 µg/ml and CR2117 and CR2118 stained the transfectant less intensely compared to CR2113 and CR2114.

Competition experiments were performed to determine whether the antibodies recognize different epitopes.

Figure 6A:
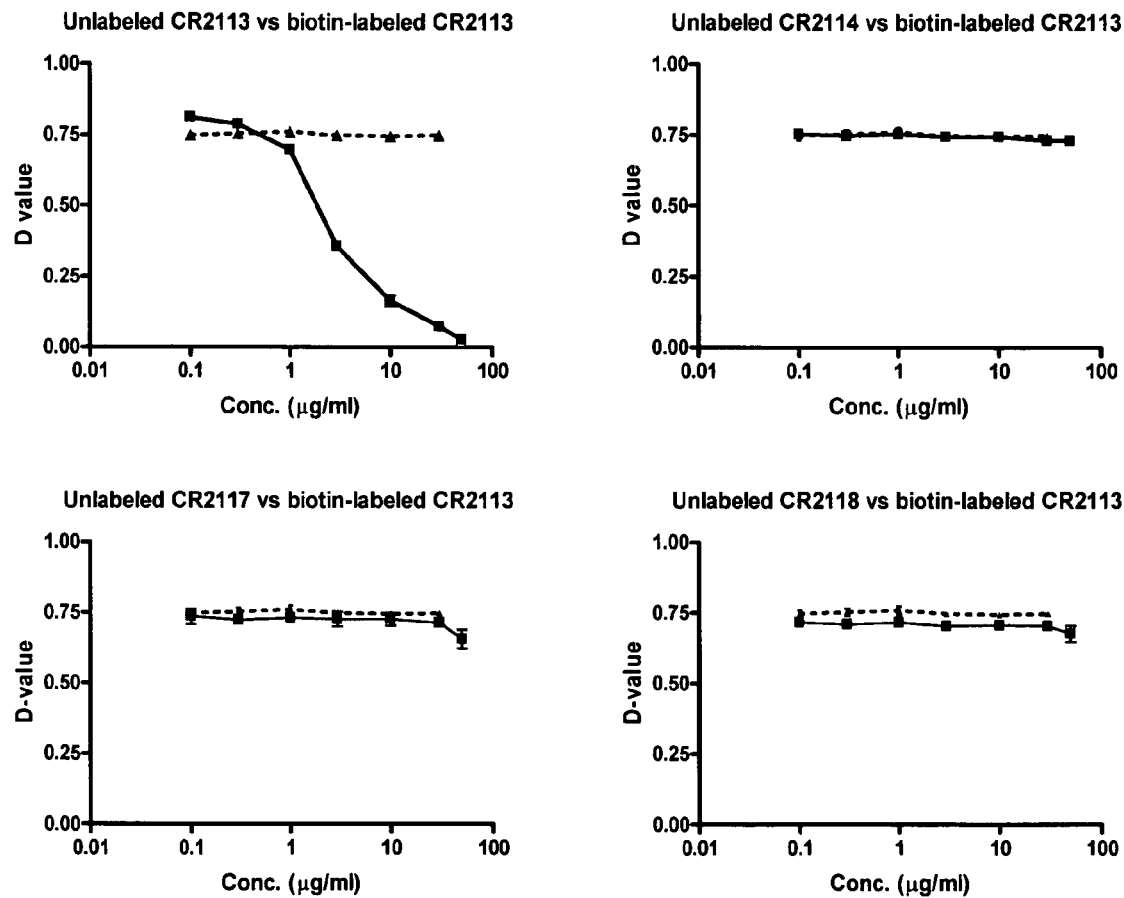
FIGS. 6A-D show competition curves for CR2113, CR2114, CR2117, and CR2118 against the human anti-human CD1a monoclonal antibodies.
Figure 6B:
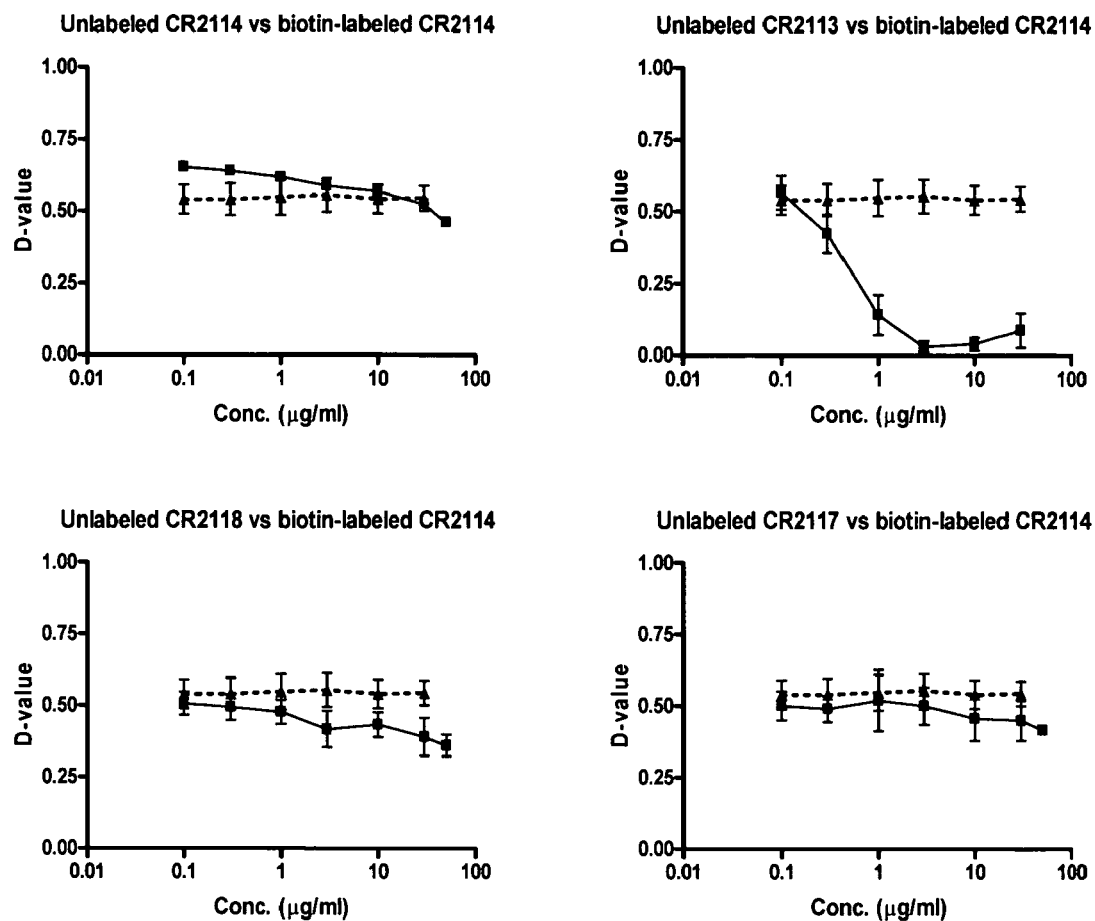
Figure 6C:
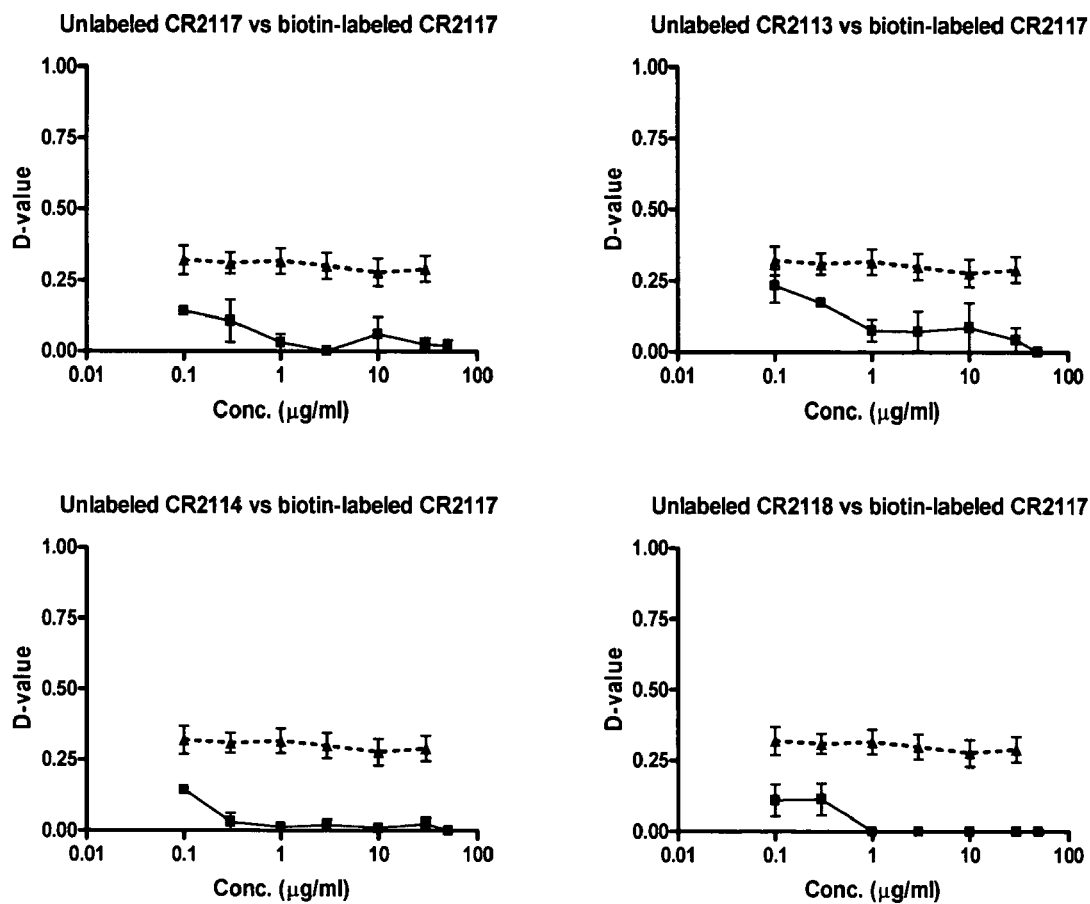
Figure 6D:
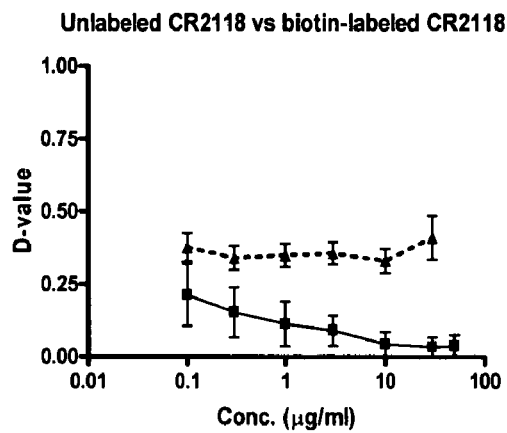
Figure 6D:
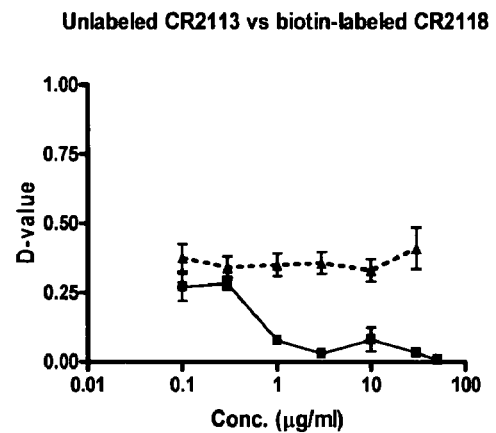
Figure 6D:
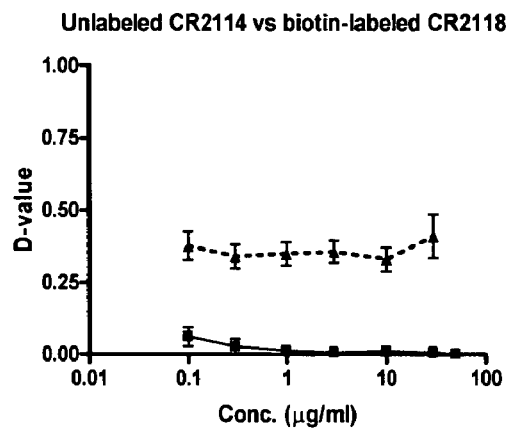
Figure 6D:
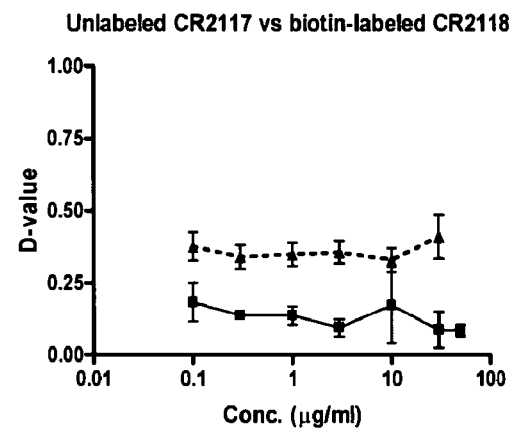

B16 mouse melanoma cells expressing human CD1a were stained with unlabeled CR2113, CR2114, CR2117, CR2118 or the negative control CR2027 at different concentrations (0.1, 0.3, 1, 3, 10, 30, 50, 100 µg/ml) for 30 minutes and then stained with one of the above antibodies labeled with biotin as described above for five minutes at a concentration of 2.5 µg/ml. Detection was by FITC-labeled streptavidin incubated for 20 minutes. Furthermore, staining was performed as described above (see Example 3). Each staining was done three successive times and the D-value calculated with K-S statistics (see above). The staining of unlabeled control antibody CR2027 is shown by the dotted line staining using the test antibody is depicted with a solid line. CR2113 was able to compete with itself in a dose dependent manner, however none of the other antibodies could compete with biotinylated CR2113 for binding (see FIG. 6A). This is likely due to its superior binding affinity for human CD1a compared to the other antibodies. In contrast, unlabeled CR2113 was able to compete for binding of CR2114 (see FIG. 6B), CR2117 (see FIG. 6C) and CR2118 (see FIG. 6D) to B16-CD1a transfectants in a concentration dependent manner. Neither CR2117 nor CR2118 was able to compete with CR2114 for binding to CD1a. This could be due to sub-optimal affinity.

In conclusion all four antibodies tested appear to share overlapping epitopes, although in the case of CR2113 and CR2114 these are unlikely to be identical due to the differences in specificity seen in FIG. 3.

Example 6

Immunohistochemistry with Human Monoclonal Anti-CD1a Antibodies

The human monoclonal anti-CD1a antibody CR2113 was analyzed for its ability to bind to normal tissue by immunohistochemistry. The murine monoclonal anti-CD1a antibody NA1 was used as a positive control antibody. For this purpose, paraffin sections of normal human skin were used. The sections were deparaffinized by melting the paraffin at 68° C. for ten minutes, and were then placed in Xylene (Richard Ellen Sci.) two times for five minutes. Sections were hydrated and then blocked for endogenous peroxidase with 50 mM sodium azide containing 0.03% $H_2O_2$ for five minutes. Subsequently, the sections were incubated with anti-human CD1a human IgG or the murine monoclonal anti-CD1a antibody NA1 for 45 minutes at room temperature. To detect bound IgG molecules the sections stained with the human IgG were incubated with a rabbit anti-human antibody for 30 minutes (Dako) followed by incubation with an anti-rabbit horse radish peroxidase antibody (Dako). Sections stained with the murine monoclonal anti-CD1a antibody NA1 were incubated with an anti-mouse horse radish peroxidase antibody (Dako). The sections were then incubated with diaminobenzidine (Dako), resulting in a local deposition of brown crystals. The sections were counterstained with hematoxilin to visualize nucleated cells within the sections. Prior to analysis the sections were dehydrated and the slides were sealed with eukitt (BDH).

No specific signal could be recovered with CR2113 even in the case where positive control tissue sections were used, suggesting that the antibody epitope is shielded or destroyed during fixation and/or preparation of the tissue sections.

Example 7

Flow Cytometric Analysis of Expression of CD1a Molecules on Fresh Tumor Samples and Tumor Cell Lines with Human Monoclonal Anti-CD1a Antibodies The human anti-CD1a IgG1 antibody panel is used to evaluate CD1a expression on the following fresh tumor samples; acute myeloid leukemia (AML), acute non-lymphocytic leukemia (ANLL), chronic myelogenous leukemia in blast crisis (CML-BC), large granular lymphocytic leukemia (LGLL), B-cell chronic lymphocytic leukemia (B-CLL), T-cell acute lymphoblastic leukemia (T-ALL) and cell line SUP-T1. For this purpose $5\times10^5$ mononuclear cells prepared by ficoll-paque gradient separation (for fresh samples) or from culture according to suppliers instructions (for cell lines) are stained with the human monoclonal anti-CD1a IgG1 antibody of the invention at a concentration of 3 µg/ml at 4° C. Binding of biotinylated 02-113 is visualized using streptavidin-FITC (Becton Dickinson). The biotinylated murine monoclonal anti-CD1a antibody NA1 is used as a positive control antibody. The stained cells are analyzed by flow cytometry.

In addition the human anti-CD1a IgG1 antibody panel was used to evaluate CD1a expression on the following cell lines: U937, Molm13, Molm14, Kg-1a, EOL-1, HEL, NB4 (all derived from AML); KT-1, MEG01, K562, KU812 (all derived from CML-BC); HALO1, REH, RS4;11, UOCB1, RcH-AcV (all derived from B-lineage ALL); Jurkat, MOLT4, MOLT3, CEM, Karpas45 (all derived from T-ALL); RPMI8226, U266, H929, KM412, MDLP8 (all derived from multiple myeloma); and the Hodgkin Disease cell lines L428 and KMH2. For this purpose $5 \times 10^5$ cells prepared from cell culture according to suppliers instructions were stained with the biotinylated human monoclonal anti-CD1a IgG1 antibody 02-113 and the biotinylated murine monoclonal anti-CD1a antibody NA1 at a concentration of 3 µg/ml at 4° C. Binding of 02-113 and NA1 was visualized using streptavidin-FITC (Becton Dickinson). The stained cells were analyzed by flow cytometry.

Figure 7:
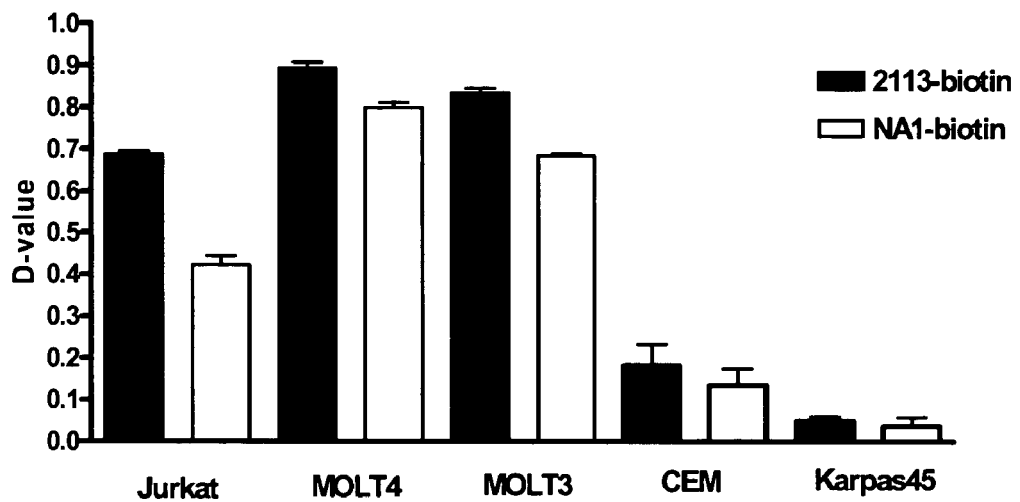
FIG. 7. Detection of CD1a cell surface expression on T-ALL cell lines by means of flow cytometry with the biotinylated antibodies CR2113 (black) and NA1 (white).

High levels of staining were observed in three out of five T-ALL cell lines with CR2113 at 3 µg/ml (see FIG. 7). All T-ALL cell lines stained better with CR2113 than with NA1 used at the same concentration.

Figure 8:
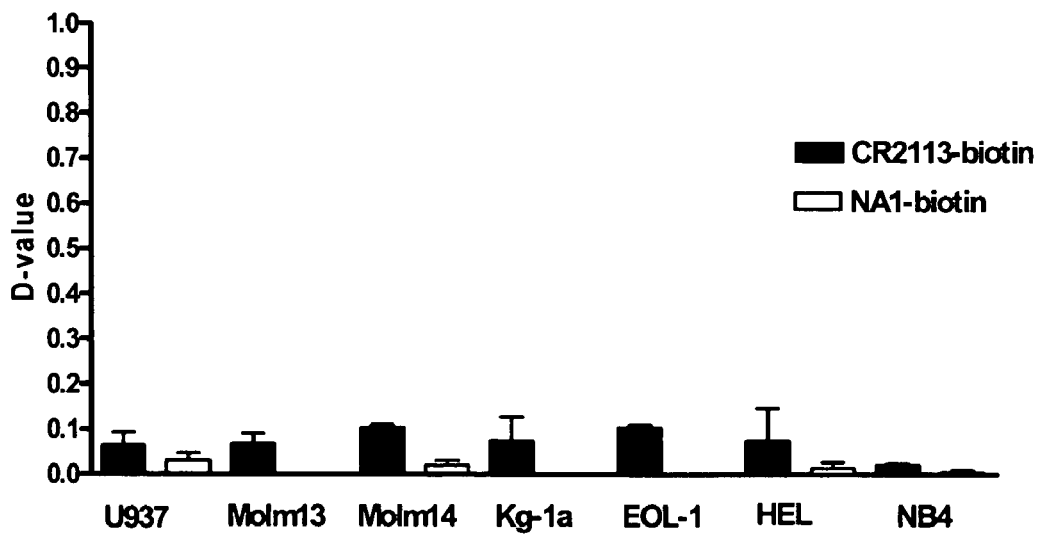
FIG. 8. Detection of CD1a cell surface expression on AML cell lines by means of flow cytometry with the biotinylated antibodies CR2113 (black) and NA1 (white).
Figure 9:
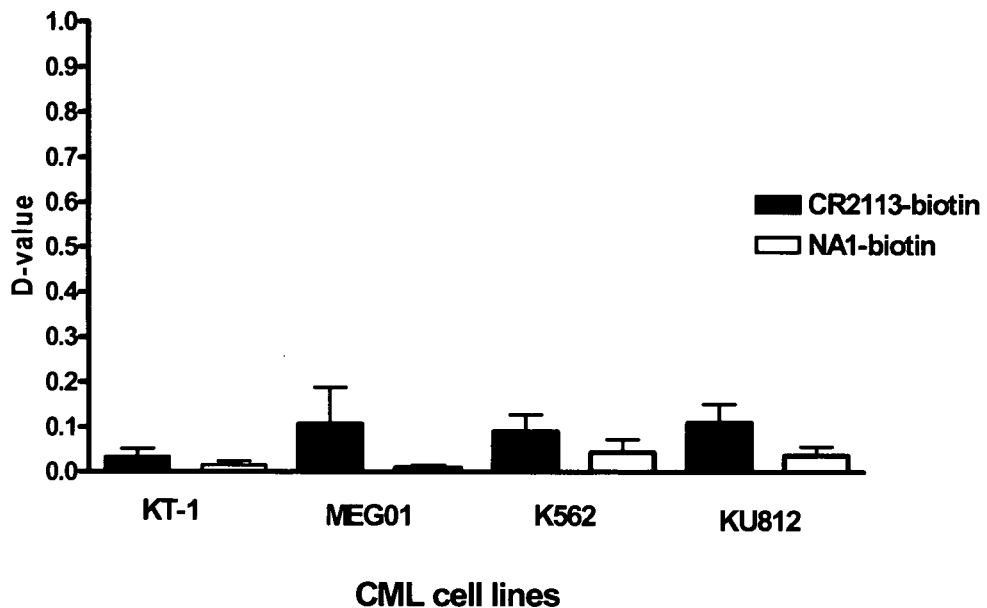
FIG. 9. Detection of CD1a cell surface expression on CML cell lines by means of flow cytometry with the biotinylated antibodies CR2113 (black) and NA1 (white).
Figure 10:
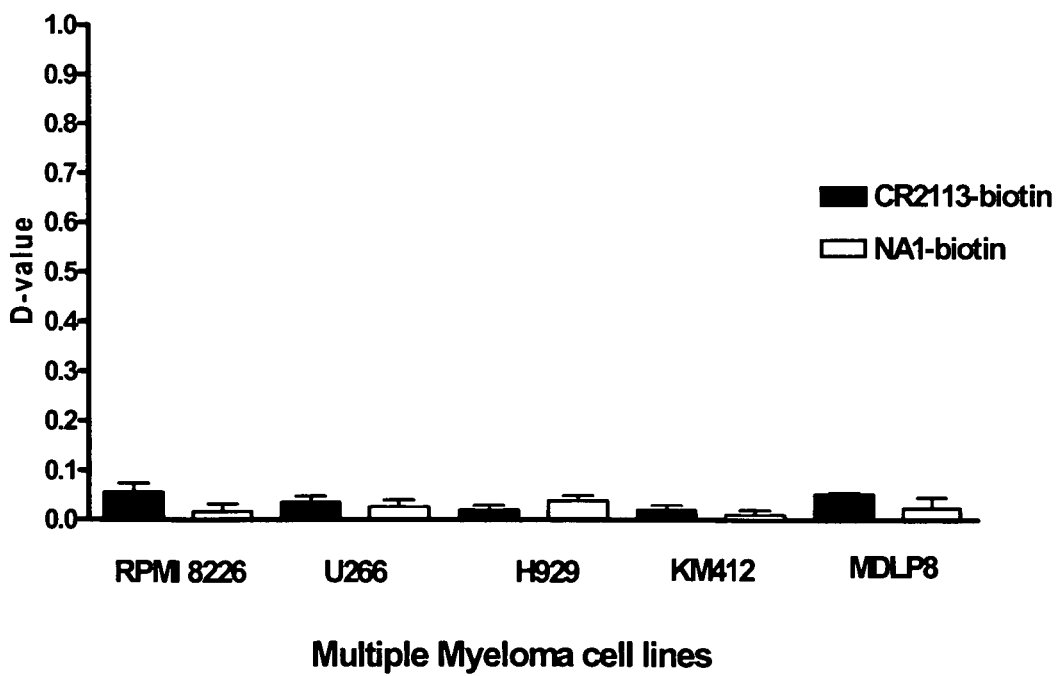
FIG. 10. Detection of CD1a cell surface expression on multiple myeloma cell lines by means of flow cytometry with the biotinylated antibodies CR2113 (black) and NA1 (white).
Figure 11:
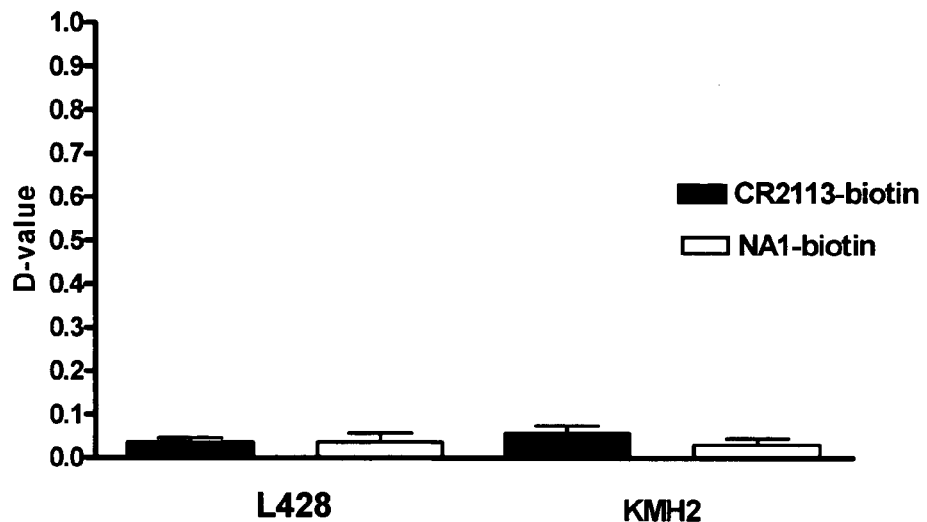
FIG. 11. Detection of CD1a cell surface expression on Hodgkin disease cell lines by means of flow cytometry with the biotinylated antibodies CR2113 (black) and NA1 (white).
Figure 12:
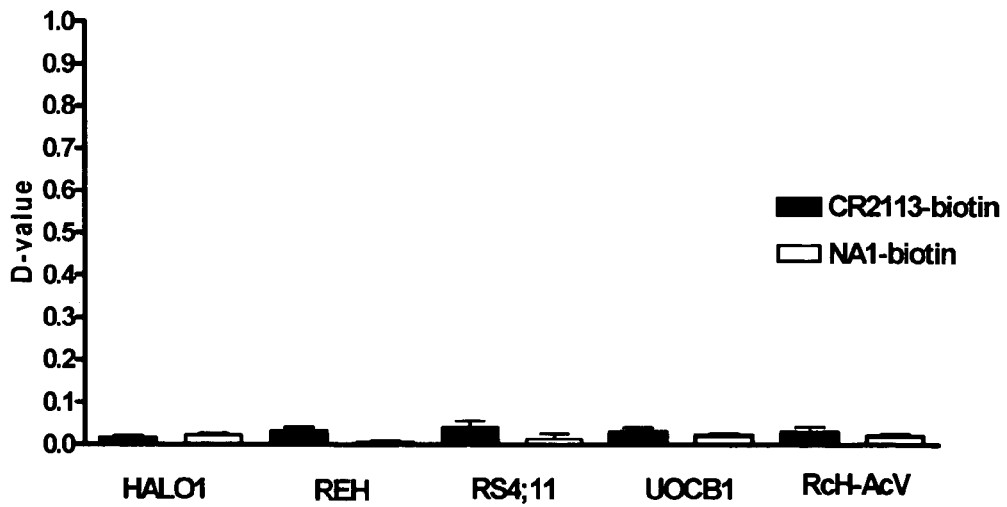
FIG. 12. Detection of CD1a cell surface expression on B-lineage ALL cell lines by means of flow cytometry with the biotinylated antibodies CR2113 (black) and NA1 (white).

CR2113 stained six out of seven AML cell lines (see FIG. 8) and three out of four CML cell lines (see FIG. 9). Again staining was higher than the positive control antibody NA1 when used at the same concentration. No specific staining for CR2113 or NA1 was observed on multiple myeloma cell lines (see FIG. 10), Hodgkin disease cell lines (see FIG. 11) or B-ALL cell lines (see FIG. 12).

Based on the high levels of CD1a staining in T-ALL cell lines, CR2113 might be particularly useful as a diagnostic and/or therapeutic molecule in T-ALL.

Example 8

Internalization Studies with Human Monoclonal Anti-CD1a Antibodies

Internalization assays with CD1a-expressing cell lines such as Jurkatt cells are performed in order to determine the internalizing capacity of the human monoclonal anti-human CD1a IgG1 antibodies. The anti-human CD1a IgG1 antibodies are stained with Oregon Green-480-SE (Molecular Probes) labelling dye as follows: 0.1 mg of dye is dissolved in 10 µl of DMSO, added to 0.4 mg of antibody in a final volume of 0.4 ml PBS, and incubated at room temperature for one hour. Subsequently, this mixture is loaded onto a Sephadex G25 column equilibrated in PBS. The labeled antibody is eluted with PBS and the colored fraction is collected. Aliquots of $5 \times 10^5$ Jurkatt cells are loaded with the appropriate antibody at a saturating concentration on ice for 30 minutes. Unbound antibody is removed by three washes with ice-cold RPMI 1640 medium containing 10% FBS medium. Subsequently, cells are resuspended in 50 µl of the medium and incubated for one hour at either 4° C. (no internalization) or 37° C. to allow internalization of the antibodies. Following three washes with ice-cold PBS, cell surface-bound antibodies are stripped off the cells with 2.5 mg/ml subtilisin for one hour at 4° C. Cells are washed again with ice-cold PBS-1% BSA and samples are analyzed by flow cytometry. With cells that are incubated at 4° C. (a temperature at which no internalization occurs) the cell-bound IgGs can be stripped off the cells as shown by loss of fluorescence. On the other hand, when cells are incubated at 37° C. to allow internalization of antibodies, the cells remain fluorescent after eliminating antibodies bound to CD1a molecules at the cell surface by stripping the cells using subtilisin. This indicates that the anti-CD1 antibodies do internalize into cells and have become resistant to protease treatment. In contrast, a negative control antibody, anti-CD20 (which does not internalize, see Ghetie et al. (2001)), can be stripped off the cells at both temperatures indicating that the antibody binds to its target, but does not internalize into the cell. On the one hand, internalization of anti-CD1a antibodies will allow better efficacy of immunoconjugates containing certain toxin molecules coupled to the internalizing anti-CD1a antibodies, if such toxin molecules need to cross the cellular membrane for efficient functioning/activity. On the other hand, anti-CD1a antibodies not capable of internalizing might be useful in radioconjugates. Such conjugates do not need to cross the cellular membrane to exert a cytotoxic effect. In addition, antibodies bound to the surface of target cells can recruit cytotoxic leukocytes such as natural killer cells (ADCC) or direct the deposition of complement (CDC). Rapid internalization of CD1a upon ligation of the antibodies could interfere with these processes.

Figure 13:
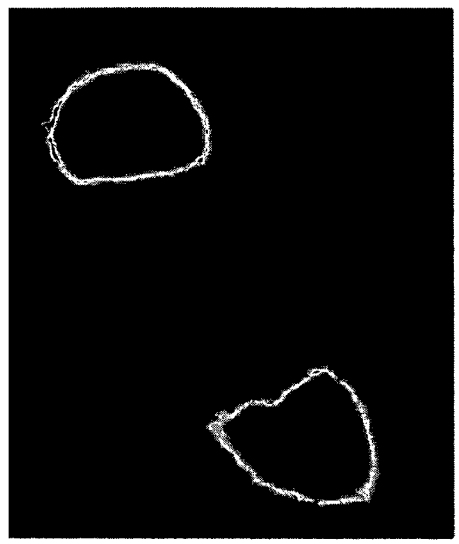
FIG. 13. Internalization of CR2113 on CD1a-positive B16 melanoma cells at 4° C. (left panel) and 37° C. (right panel).
Figure 13:
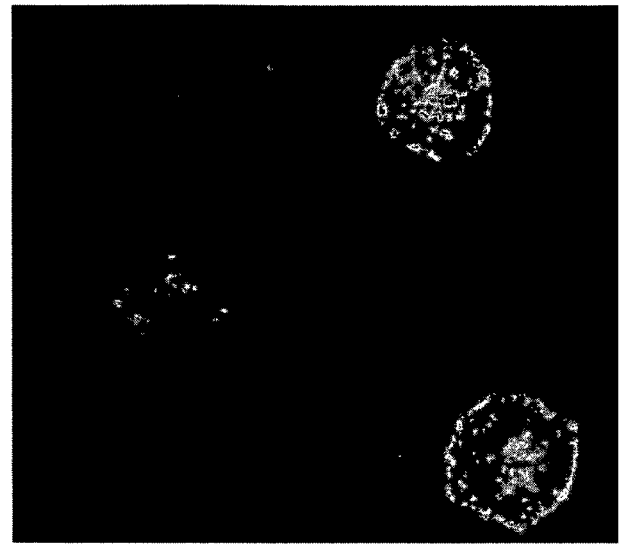
Figure 14:
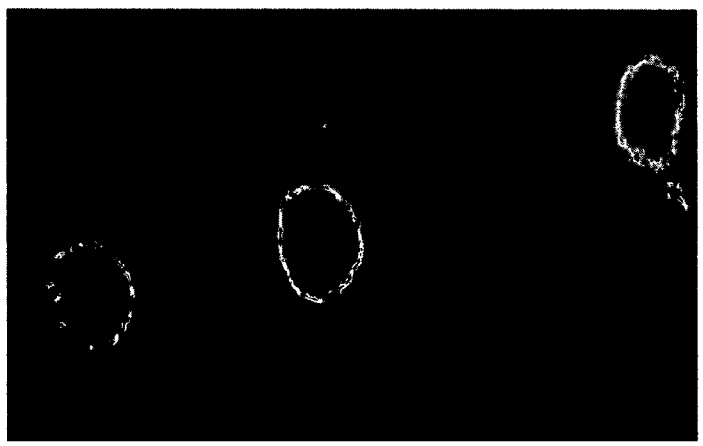
FIG. 14. Internalization of NA1 on CD1a-positive B16 melanoma cells at 4° C. (left panel) and 37° C. (right panel).
Figure 14:

Alternatively, internalization assays were performed with the CD1a transfected B16 cell line to determine the internalizing capacity of the human monoclonal anti-human CD1a IgG1 CR2113. CR2113 and NA1 were labeled with Alexa488-SE (Molecular Probes) labeling dye as follows: 0.1 mg of dye was dissolved in 10 µl of DMSO, added to 0.4 mg of antibody in a final volume of 0.4 ml PBS, and incubated at room temperature for one hour. Subsequently, this mixture was loaded onto a Sephadex-G25 column equilibrated in PBS. The labeled antibody was eluted with PBS and the colored fraction was collected. Aliquots of $5 \times 10^5$ transfected B16 cells were loaded with the appropriate antibody at a saturating concentration on ice for 60 minutes. Unbound antibody was removed by three washes with ice-cold RPMI 1640 medium containing 10% FBS medium. Subsequently, cells were resuspended in 50 µl of the medium and incubated overnight at either 4° C. (no internalization) or 37° C. to allow internalization of the antibodies. Following three washes with ice-cold PBS, the cells were cytospun on to glass slides and visualized by confocal microscope. CR2113 and NA1 did not show internalization, when cells were kept at 4° C. All fluorescent signal was observed at the cell surface (see FIGS. 13 and 14, left panel). However, after incubation at 37° C. a significant proportion of the fluorescent signal in cells incubated with CR2113 and cells incubated with NA1 was present inside the cell (see FIGS. 13 and 14, right panel). The observed internalizing activity might increase the therapeutic value of CR2113 by increasing the delivery efficiency of a toxic payload, if such toxin molecules need to cross the cellular membrane for efficient functioning/activity. In addition, this internalizing activity may allow CR2113 to be used as a vaccine adjuvant by allowing delivery of conjugated immunogens to the antigen presenting pathways of dendritic cells such as Langerhans cells.

Example 9

Induction of Antibody Dependent Cellular Cytotoxicity (ADCC) and Complement Dependent Cytotoxicity (CDC) in Tumor Cells Using Human Anti-CD1A Antibodies To determine the ability of the human monoclonal human anti-CD1a antibodies to induce antibody dependent cellular cytotoxicity (ADCC) and complement dependent cytotoxicity (CDC) standard $^{51}$Cr release assays are performed. For ADCC experiments, HL60 or U937 tumor target cells are labeled with 100 µCi of $^{51}$Cr (Amersham, Buckinghamshire, UK) for one hour at 37° C. Alternatively, B16 tumor target cells transfected with CD1a, CD1d or with empty vector are labeled with 100 µCi of $^{51}$Cr (Amersham, Buckinghamshire, UK) for one hour at 37° C. After extensive washing, the target cells are plated in U-bottom microtiter plates at a concentration of 5×10³ cells/well. Isolated human peripheral blood mononuclear cells are subsequently added at several effector to target ratios ranging from 80:1 to 10:1 or are added not at all. The cell mixtures are incubated in triplicate at 37° C. in the presence of various concentrations of the human monoclonal anti-CD1a antibodies in a final volume of 150 µl. After four hours of incubation, part of the supernatant is harvested and its $^{51}$Cr content is measured. The percentage of specific lysis is calculated using the formula: % specific lysis=([experimental cpm−basal cpm]/[maximal cpm−basal cpm])× 100%. Maximal lysis is determined by lysing the target cells with 1% Triton X-100 while basal release is measured by incubating the target cells with medium alone. For CDC experiments the same procedure was followed as detailed above with the exception that the effector cells were replaced by 50 µl human serum as a source of complement.

Alternatively, non-radioactive cytotoxicity assays (Promega) were performed to measure complement dependent cytotoxicity (CDC) and antibody dependent cellular cytotoxicity (ADCC). For CDC, the human anti-CD1a IgG1 antibody 02-113 or the murine anti-CD1a monoclonal antibody NA1, at a concentration of 4.5 µg/ml, alone or in combination with 25 µl of a 1:10 dilution of normal human serum complement (Quidel) was added to target cells (5×10³ cells per sample), followed by a 3 hour incubation (37° C., 5% $CO_2$). For ADCC, normal peripheral blood mononuclear cells (PBMC) were isolated from healthy volunteers by ficoll-plaque separation. Target cells were incubated (four hours, 37° C., 5% $CO_2$) with the human anti-CD1a IgG1 antibody 02-113 or the murine anti-CD1a monoclonal antibody NA1, at a concentration of 4.5 µg/ml alone or in combination with PBMC in effector/target ratio of 50:1. Cytotoxicity was determined as a function of lactate dehydrogenase (LDH) enzymatic activity released from the cytosol of damaged cells into the supernatant. LDH activity was quantitated by monitoring 490 nm (ELISA reader). Percentage of cytolysis was calculated using the manufacturer's equation: Cytotoxicity (%)=experimental-effector spontaneous-target spontaneous/ (target maximum-target spontaneous)×100.

Figure 15:
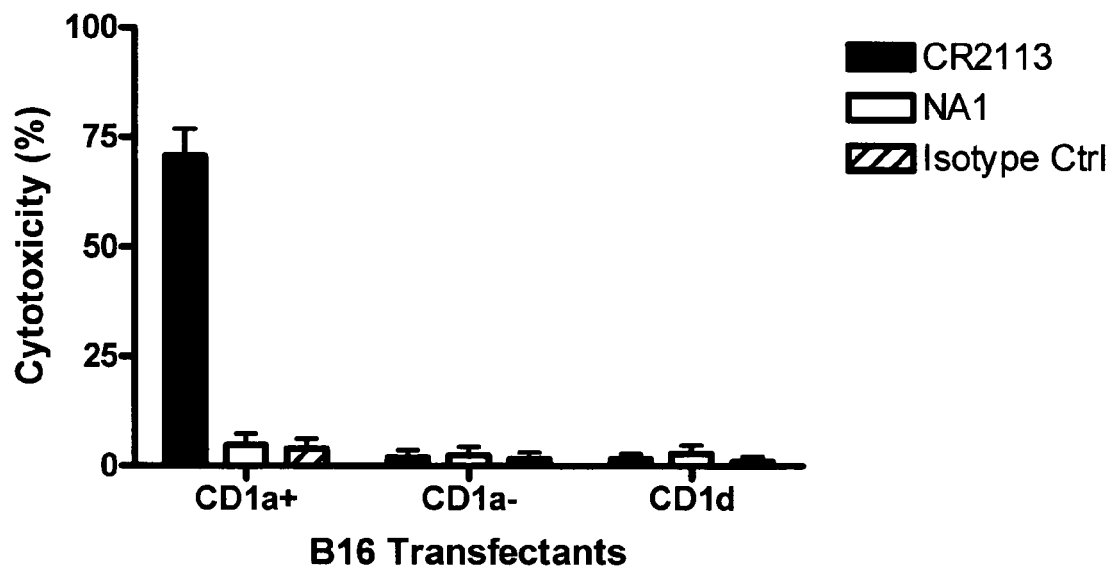
FIG. 15. ADCC-activity of CR2113 (black), NA1 (white) and a control antibody (striped) on CD1a-positive B16 cells, CD1a-negative control B16 cells and CD1d-positive B16 cells.

The ADCC-activity of CR2113 was compared to that of NA1 on CD1a-positive B16 cells as well as negative control untransfected cells and CD1d -positive control cells. Incubation with a fixed concentration of CR2113 (4.5 µg/ml) resulted in 70% cytotoxicity, whereas no activity was observed on the control cells. In contrast, the murine monoclonal anti-CD1a antibody NA1 did not show ADCC-activity (see FIG. 15).

Figure 16:
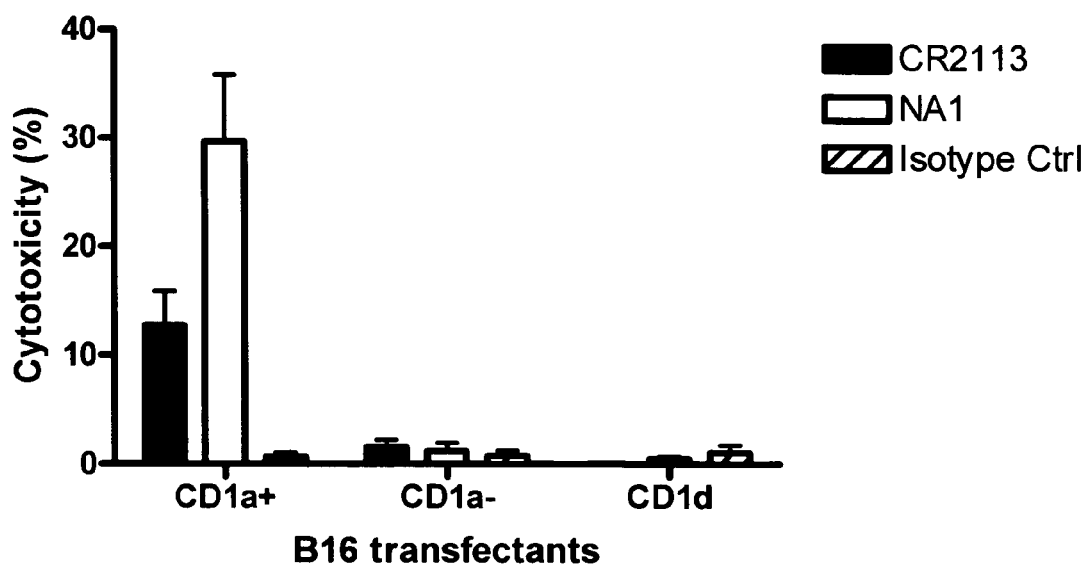
FIG. 16. CDC-activity of CR2113 (black), NA1 (white) and a control antibody (striped) on CD1a-positive B16 cells, CD1a-negative control B16 cells and CD1d-positive B16 cells.

CR2113 and NA1 both exhibited complement dependent cytotoxic activity that was significantly higher on CD1a+B16 cells than on control cells (see FIG. 16).

Together these data strongly suggest that the antibodies may exhibit tumor-killing activity in vivo. In that respect, CR2113 might be particularly suitable, as it has a high ADCC cytotoxicity and particularly ADCC is considered to be an important immunological mechanism in tumor cell killing.

Figure 17:
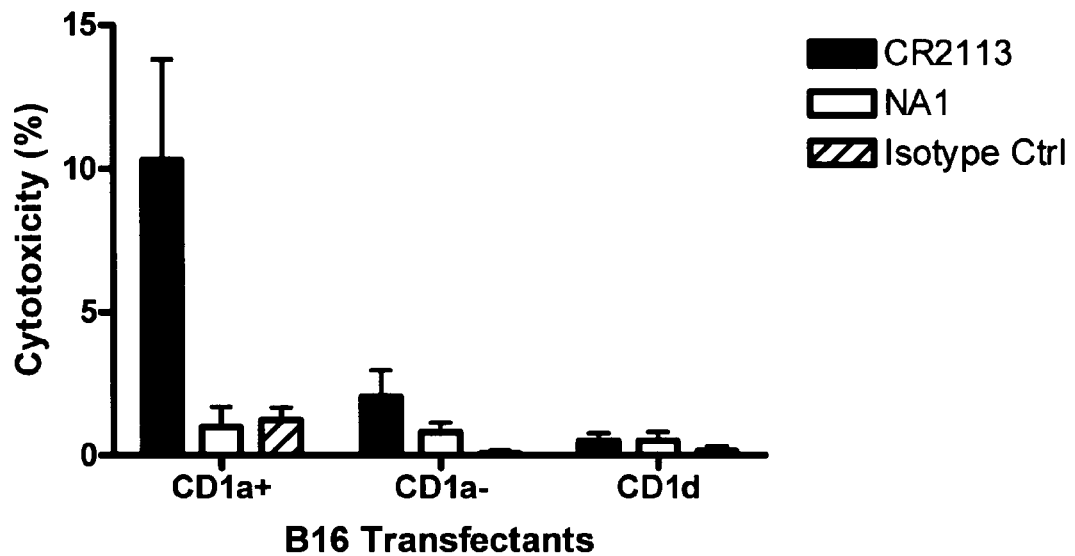
FIG. 17. Cytotoxic activity of CR2113 (black), NA1 (white) and a control antibody (striped) on CD1a-positive B16 cells, CD1a-negative control B16 cells and CD1d-positive B16 cells in the ADCC-assay in the absence of effector cells.
Figure 18:
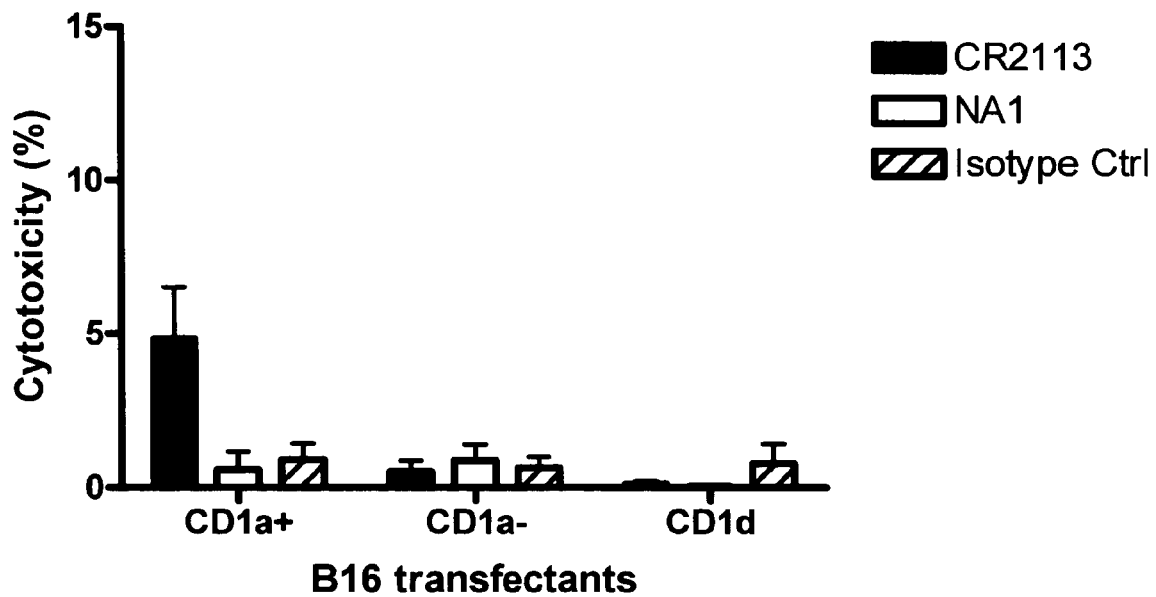
FIG. 18. Cytotoxic activity of CR2113 (black), NA1 (white) and a control antibody (striped) on CD1a-positive B16 cells, CD1a-negative control B16 cells and CD1d-positive B16 cells in the CDC-assay in the absence of complement.

Interestingly, in both the ADCC-assay and the CDC-assay CR2113 exhibited significant activity against the CD1a+ target cells without the presence of effector cells (ADCC-assay; see FIG. 17) or complement (CDC-assay; see FIG. 18). CR2113 did not show this apoptotic activity with both control target cell lines nor did the mouse monoclonal antibody NA1 show this apoptotic activity with CD1a+ target cells. These data suggest that CR2113 is not only able to efficiently recruit effector cells/complement for target killing, but has an intrinsic cytotoxicity/apoptotic activity to kill target cells by interaction with its ligand as well. This feature makes the antibody suitable for use in therapy.

Example 10

In Vivo Anti-tumor Efficacy of Human Anti-CD1a Antibodies in a CD1a-transfected Mouse Tumor Model To analyze the potential anti-tumor efficacy of the human anti-CD1a antibodies in vivo, animal experiments employing a human CD1a-transfected mouse B16 tumor model are performed. This tumor has been described extensively in the tumor-immunology literature (see Fidler et al. (1976)) and grows progressively in, for instance, syngeneic C57B1/6 mice. To test the effect of anti-CD1a treatment, C57B1/6, C57B1/6 nude, SCID or NOD-SCID mice are inoculated subcutaneously at day 0 with 1×10⁶ B16 tumor cells. Each mouse receives B16 cells transfected with CD1a cDNA in the sense orientation (i.e., normally expressed) in one flank. In the opposite flank mice receive B16 cells transfected with CD1a cDNA in the antisense orientation (i.e., not expressed) to act as a negative control. In some experiments CD1a-B16 cells are cotransfected with luciferase for real time detection of tumor growth. The animals are given a dose of 240 µg human anti-CD1a antibody intraperitoneally (i.p.) at day 1, followed by three more doses of 80 µg antibody i.p. at days 3, 6 and 9. The animals are then monitored for tumor growth for over 28 days, animals are sacrificed when tumor sizes exceed 2 cm³ or after ulceration of the tumor. Tumor size can be monitored by means of fluorescent imagery (in case of luciferase transfected B16 cells) or directly by callipers. A potential anti-tumor effect of the antibodies is analyzed by comparing the tumor outgrowth in animals receiving antibody treatment as compared to a control groups that are treated with the saline vehicle or with a human IgG1 control antibody.

All anti-CD1a monoclonal antibodies capable of specifically binding to CD1a might be tested in the in vivo model. Effectiveness in the ADCC and/or CDC assay is not a criterion for inclusion in the in vivo study. Significant inhibition of tumor growth compared to the isotype antibody controls is considered to be a strong indication that the anti-CD1a monoclonal antibodies are efficacious in inhibiting growth of CD1a-expressing tumors in humans.

Example 11

BIACORE Analysis of the Anti-CD1a Antibodies

The BIACORE 3000, which applies the technique of real-time surface plasmon resonance, is used to perform affinity measurements with the anti-CD1a antibodies prepared as described above and a murine anti-CD1a control antibody. First, the ligand, i.e., the CD1a protein (Abnova corporation), is immobilized as a ligand on a research grade CM5 4-flow channel (Fc) sensor chip using amine coupling. Briefly, the dextran matrix of CM5 chip (BIACORE) is activated with a mixture of N-hydroxysuccinimide (NHS) and N-ethyl-N'-(dimethylaminopropyl)carbodiimide (EDC). Next, the CD1A protein (preferably 30 µg/ml) is coupled to the activated carboxyl groups on the matrix. After coupling, 1 M ethanolamine-HCL (pH 8.5) is added to deactivate remaining active carboxyl groups. One of the four channels is activated and deactivated without CD1A protein coupling and serves as a control flow channel. Thereafter, kinetic analyses are performed. For that purpose association rate (Ka), dissociation rate (Kd) and affinity (KD) of the anti-CD1A antibodies are investigated. A concentration series between 0.01 to 1000 nM is applied at 25° C. (dilution factor 2, dilution buffer HBS-EP). One of the four channels is used as reference flow cell and injection of HBS-EP buffer serves as control injection. Fifty µl of the respective antibodies is injected with a constant flow rate of 20 µl/min. At the end of the injection, HBS-EP buffer is applied for 750 seconds followed by regeneration of the CM5 chip with pulses of regeneration buffer (for instance, glycine, pH 2) according to the manufacturer instructions. The experiment is repeated three times to determine the assay variation. Then, BIACORE evaluation software is used to fit the association and dissociation curves of the concentrations in the concentration series. Based on these fits affinity is determined. To minimize possible avidity effects of the bivalent antibodies, the following 4 important parameters are included during evaluation; 1) concentration range of 0.1–10×KD, 2) low standard error values of Ka and Kd rates, 3) low residual Chi$^2$ values, and 4) good precision (preferably <20%). Anti-CD1a antibodies bind preferentially with high affinity in the 0.1-50 nM range.

TABLE 2

Binding of the human anti-CD1a monoclonal antibodies to mouse thymocytes measured by flow cytometry.

| Antibody | Mouse Thymocytes (D-value) |
|---|---|
| CR2113 | 0 |
| CR2114 | 0 |
| CR2115 | 0 |
| CR2116 | 0 |
| CR2117 | 0 |
| CR2118 | 0 |
| Positive control (mouse anti-human CD1a-FITC) | 0.03 |
| Negative control (anti-GBSIII antibody) | 0 |
| Negative control (mouse IgG; k-FITC) | 0 |

TABLE 3

Amino acid sequences of CDR regions of CR2113 and CR2118.

| Name of Ab | Amino acid sequence of HCDR3 | Amino acid sequence of HCDR1 | Amino acid sequence of HCDR2 | Amino acid sequence of LCDR1 | Amino acid sequence of LCDR2 | Amino acid sequence of LCDR3 |
|---|---|---|---|---|---|---|
| CR2113 | APYMMYFDS (SEQ ID NO: 1) | GYYWS (SEQ ID NO: 66) | YIYYSGST NYNPSLKS (SEQ ID NO: 67) | RASQSISS YLN (SEQ ID NO: 68) | AASSLQS (SEQ ID NO: 69) | QQSYSTP (SEQ ID NO: 70) |
| CR2118 | SAWWLSFDS DS (SEQ ID NO: 6) | SYAMH (SEQ ID NO: 71) | AISTGGGT YYADSVKG (SEQ ID NO: 72) | RASQSISS YLN (SEQ ID NO: 68) | AASSLQS (SEQ ID NO: 69) | QQSYSTP (SEQ ID NO: 70) |

TABLE 1

Nucleotide and amino acid sequences, heavy chain CDR3 amino acid sequence and gene identity of the VH and VL genes of the CD1a-specific scFvs.

| Name of scFv | Amino acid sequence of HCDR3 | SEQ ID NO of nucleotide sequence of scFv | SEQ ID NO of amino acid sequence of scFv | VH family | VL family |
|---|---|---|---|---|---|
| SC02-113 | APYMMYFDS (SEQ ID NO: 1) | SEQ ID NO: 25 | SEQ ID NO: 26 | VH4: DP-66 | Vκ1: DPK-9 |
| SC02-114 | ETWWQSFDY (SEQ ID NO: 2) | SEQ ID NO: 27 | SEQ ID NO: 28 | VH3: DP-51 | Vκ1: DPK-9 |
| SC02-115 | SQMPSYFDY (SEQ ID NO: 3) | SEQ ID NO: 29 | SEQ ID NO: 30 | VH1: DP-14 | Vλ3: DPL-16 |
| SC02-116 | DALWLAFDY (SEQ ID NO: 4) | SEQ ID NO: 31 | SEQ ID NO: 32 | VH3: DP-47 | Vκ1: DPK-9 |
| SC02-117 | STPWFSFDY (SEQ ID NO: 5) | SEQ ID NO: 33 | SEQ ID NO: 34 | VH3: DP-48 | Vκ1: DPK-9 |
| SC02-118 | SAWWLSFDS (SEQ ID NO: 6) | SEQ ID NO: 35 | SEQ ID NO: 36 | VH3: DP-48 | Vκ1: DPK-9 |

REFERENCES

Amiot M., Bernard A., Raynal B., Knapp W., Deschildre C. and Boumsell L. (1986), *J. Immunol.* 136:1752-1757.

Boel E., Verlaan S., Poppelier M. J., Westerdaal N .A., Van Strijp J. A. and Logtenberg T. (2000), *J. Immunol. Methods* 239:153-166.

Burton D. R. and Barbas C. F. (1994), *Adv. Immunol.* 57:191-280.

De Kruif J., Terstappen L., Boel E. and Logtenberg T. (1995a), *Proc. Natl. Acad. Sci. USA* 92:3938-3942.

De Kruif J., Boel E. and Logtenberg T. (1995b), *J. Mol. Biol.* 248:97-105.

Fidler I. J., Gersten D. M. and Budmen M. B. (1976), *Cancer Research* 36:3610-3165.

Furue M., Nindl M., Kawabe K., Nakamura K., Ishibashi Y. and Sagawa K. (1992), *J. Am. Acad. Dermatol.* 27:419-426.

Ghetie M. A., Bright H. and Vitetta E. S. (2001), *Blood* 97:1392-1398.

Huls G., Heijnen I. J., Cuomo E., van der Linden J., Boel E., van de Winkel J. and Logtenberg T. (1999), *Cancer Res.* 59: 5778-5784.

Jonuleit H., Kühn U., Müller G., Steinbrink K., Paragnik L., Schmitt E., Knop J., Enk A. H. (1997), *Eur. J. Immunology* 27: 3135-3142.

Kelly K. M., Beverly P. C., Chu A. C., Davenport V., Gordon I., Smith M. and Pritchard J. (1994), *J. Pediatr.* 125:717-722.

Merle-Beral H., Boumsell L., Michel A. and Debre P. (1989), *Br. J. Haematol.* 72:209-212.

Salomone M. C., Roisman F. R., Santiago J., Satz M. L. and Fainboim L. (1990a), *Dis. Markers* 8:265-274.

Salomone M. C., Roisman F. R., Santiago J., Satz M. L. and Fainboim L. (1990b), *Dis. Markers* 8:275-281.

Teunissen M. B. (1992), *Histochem. J.* 24:697-716.

Van Kroonenburgh M. J. and Pauwels E. K. (1988), *Nucl. Med. Commun.* 9:919-930.

---

What is claimed is:

1. A monoclonal antibody that binds to human CD1a, wherein the monoclonal antibody is selected from the group consisting of:
   a) a monoclonal antibody that comprises a heavy chain variable region comprising the amino acid sequence of SEQ ID NO:8, and a light chain variable region comprising SEQ ID NO: 20; and
   b) a monoclonal antibody that comprises a heavy chain variable region comprising the amino acid sequence of SEQ ID NO:18, and a light chain variable region comprising SEQ ID NO: 20.

2. A monoclonal antibody capable of specifically binding to human CD1a, wherein the monoclonal antibody is selected from the group consisting of:
   a) a monoclonal antibody that comprises a heavy chain variable region comprising the amino acid sequence of SEQ ID NO:8, and a light chain variable region comprising SEQ ID NO: 20; and
   b) a monoclonal antibody that comprises a heavy chain variable region comprising the amino acid sequence of SEQ ID NO:18, and a light chain variable region comprising SEQ ID NO: 20.

3. The monoclonal antibody of claim 1, wherein the monoclonal antibody is an IgG1.

4. The monoclonal antibody of claim 1, wherein the antibody has cytotoxic activity against a CD1a-expressing cell.

5. A composition comprising the monoclonal antibody of claim 1.

* * * * *

UNITED STATES PATENT AND TRADEMARK OFFICE
CERTIFICATE OF CORRECTION

PATENT NO. : 7,968,092 B2  Page 1 of 1
APPLICATION NO. : 11/387997
DATED : June 28, 2011
INVENTOR(S) : Mark Throsby et al.

It is certified that error appears in the above-identified patent and that said Letters Patent is hereby corrected as shown below:

In the specification:
COLUMN 1,  LINE 13,  change "PCT/EP03151096," to --PCT/EP03/51096,--

Signed and Sealed this
Thirty-first Day of December, 2013

Margaret A. Focarino
*Commissioner for Patents of the United States Patent and Trademark Office*

```
                        SEQUENCE LISTING

<160> NUMBER OF SEQ ID NOS: 72

<210> SEQ ID NO 1
<211> LENGTH: 9
<212> TYPE: PRT
<213> ORGANISM: Artificial sequence
<220> FEATURE:
<223> OTHER INFORMATION: Chemically synthesized - HCDR3 of SC02-113

<400> SEQUENCE: 1

Ala Pro Tyr Met Met Tyr Phe Asp Ser
1               5

<210> SEQ ID NO 2
<211> LENGTH: 9
<212> TYPE: PRT
<213> ORGANISM: Artificial sequence
<220> FEATURE:
<223> OTHER INFORMATION: Chemically synthesized - HCDR3 of SC02-114

<400> SEQUENCE: 2

Glu Thr Trp Trp Gln Ser Phe Asp Tyr
1               5

<210> SEQ ID NO 3
<211> LENGTH: 9
<212> TYPE: PRT
<213> ORGANISM: Artificial sequence
<220> FEATURE:
<223> OTHER INFORMATION: Chemically synthesized - HCDR3 of SC02-115

<400> SEQUENCE: 3

Ser Gln Met Pro Ser Tyr Phe Asp Tyr
1               5

<210> SEQ ID NO 4
<211> LENGTH: 9
<212> TYPE: PRT
<213> ORGANISM: Artificial sequence
<220> FEATURE:
<223> OTHER INFORMATION: Chemically synthesized - HCDR3 of SC02-116

<400> SEQUENCE: 4

Asp Ala Leu Trp Leu Ala Phe Asp Tyr
1               5

<210> SEQ ID NO 5
<211> LENGTH: 9
<212> TYPE: PRT
<213> ORGANISM: Artificial sequence
<220> FEATURE:
<223> OTHER INFORMATION: Chemically synthesized - HCDR3 of SC02-117

<400> SEQUENCE: 5

Ser Thr Pro Trp Phe Ser Phe Asp Tyr
1               5
```

<210> SEQ ID NO 6
<211> LENGTH: 9
<212> TYPE: PRT
<213> ORGANISM: Artificial sequence
<220> FEATURE:
<223> OTHER INFORMATION: Chemically synthesized - HCDR3 of SC02-118

<400> SEQUENCE: 6

Ser Ala Trp Trp Leu Ser Phe Asp Ser
1               5

<210> SEQ ID NO 7
<211> LENGTH: 351
<212> TYPE: DNA
<213> ORGANISM: Artificial sequence
<220> FEATURE:
<223> OTHER INFORMATION: Chemically synthesized - Variable region of
      heavy chain of 02-113
<220> FEATURE:
<221> NAME/KEY: CDS
<222> LOCATION: (1)..(351)

<400> SEQUENCE: 7 cag gtg cag ctg cag gag tcc ggc gca gga ctg ttg aag cct tcg gag      48
Gln Val Gln Leu Gln Glu Ser Gly Ala Gly Leu Leu Lys Pro Ser Glu
1               5                   10                  15 acc ctg tcc ctc acc tgc gct gtc tat ggt ggg tct ttc agt ggc tac      96
Thr Leu Ser Leu Thr Cys Ala Val Tyr Gly Gly Ser Phe Ser Gly Tyr
                20                  25                  30 tac tgg agc tgg atc cgg cag ccc cca ggg aag gga ctg gag tgg att     144
Tyr Trp Ser Trp Ile Arg Gln Pro Pro Gly Lys Gly Leu Glu Trp Ile
            35                  40                  45 ggg tat atc tat tac agt ggg agc acc aac tac aac ccc tcc ctc aag     192
Gly Tyr Ile Tyr Tyr Ser Gly Ser Thr Asn Tyr Asn Pro Ser Leu Lys
        50                  55                  60 agt cga gtc acc ata tca gta gac acg tcc aag aac cag ttc tcc ctg     240
Ser Arg Val Thr Ile Ser Val Asp Thr Ser Lys Asn Gln Phe Ser Leu
65                  70                  75                  80 aag ctg agc tct gtg acc gct gcg gac acg gcc gtg tat tac tgt gca     288
Lys Leu Ser Ser Val Thr Ala Ala Asp Thr Ala Val Tyr Tyr Cys Ala
                85                  90                  95 aag gcc cct tat atg atg tat ttt gac tcc tgg ggc cag ggc acc ctg     336
Lys Ala Pro Tyr Met Met Tyr Phe Asp Ser Trp Gly Gln Gly Thr Leu
            100                 105                 110 gtg acc gtc tcc agc                                                 351
Val Thr Val Ser Ser
        115

<210> SEQ ID NO 8
<211> LENGTH: 117
<212> TYPE: PRT
<213> ORGANISM: Artificial sequence
<220> FEATURE:
<223> OTHER INFORMATION: Chemically synthesized - Variable region of
      heavy chain of 02-113

<400> SEQUENCE: 8

Gln Val Gln Leu Gln Glu Ser Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
        50                  55                  60

```
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Lys Ala Pro Tyr Met Met Tyr Phe Asp Ser Trp Gly Gln Gly Thr Leu
            100                 105                 110

Val Thr Val Ser Ser
        115

<210> SEQ ID NO 9
<211> LENGTH: 354
<212> TYPE: DNA
<213> ORGANISM: Artificial sequence
<220> FEATURE:
<223> OTHER INFORMATION: Chemically synthesized - Variable region of
      heavy chain of 02-114
<220> FEATURE:
<221> NAME/KEY: CDS
<222> LOCATION: (1)..(354)

<400> SEQUENCE: 9 gag gtg cag ctg gtg gag tct ggg gga ggc ttg gta cag cct ggg ggg      48
Glu Val Gln Leu Val Glu Ser Gly Gly Gly Leu Val Gln Pro Gly Gly
 1               5                  10                  15 tcc ctg aga ctc tcc tgt gca gcc tct gga ttc acc ttc agt agc tat      96
Ser Leu Arg Leu Ser Cys Ala Ala Ser Gly Phe Thr Phe Ser Ser Tyr
             20                  25                  30 agc atg aac tgg gtc cgc cag gct cca ggg aag ggg ctg gag tgg gtt     144
Ser Met Asn Trp Val Arg Gln Ala Pro Gly Lys Gly Leu Glu Trp Val
         35                  40                  45 tca tac att agt agt agt agt acc ata tac tac gca gac tct gtg         192
Ser Tyr Ile Ser Ser Ser Ser Thr Ile Tyr Tyr Ala Asp Ser Val
     50                  55                  60 aag ggc cga ttc acc atc tcc aga gac aat gcc aag aac tca ctg tat     240
Lys Gly Arg Phe Thr Ile Ser Arg Asp Asn Ala Lys Asn Ser Leu Tyr
 65                  70                  75                  80 ctg caa atg aac agc ctg aga gac gag gac acg gcc gtg tat tac tgt     288
Leu Gln Met Asn Ser Leu Arg Asp Glu Asp Thr Ala Val Tyr Tyr Cys
                 85                  90                  95 gca aag gag act tgg tgg cag tcc ttt gac tac tgg ggc cag ggc acc     336
Ala Lys Glu Thr Trp Trp Gln Ser Phe Asp Tyr Trp Gly Gln Gly Thr
            100                 105                 110 ctg gtg acc gtc tcc agc                                             354
Leu Val Thr Val Ser Ser
        115

<210> SEQ ID NO 10
<211> LENGTH: 118
<212> TYPE: PRT
<213> ORGANISM: Artificial sequence
<220> FEATURE:
<223> OTHER INFORMATION: Chemically synthesized - Variable region of
      heavy chain of 02-114

<400> SEQUENCE: 10

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ser Tyr Ile Ser Ser Ser Ser Thr Ile Tyr Tyr Ala Asp Ser Val
```

```
                50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Lys Glu Thr Trp Trp Gln Ser Phe Asp Tyr Trp Gly Gln Gly Thr
            100                 105                 110

Leu Val Thr Val Ser Ser
            115

<210> SEQ ID NO 11
<211> LENGTH: 354
<212> TYPE: DNA
<213> ORGANISM: Artificial sequence
<220> FEATURE:
<223> OTHER INFORMATION: Chemically synthesized - Variable region of
      heavy chain of 02-115
<220> FEATURE:
<221> NAME/KEY: CDS
<222> LOCATION: (1)..(354)

<400> SEQUENCE: 11 cag gtg cag ctg gtg cag tct ggg gct gag gcg aag aag cct ggg gcc       48
Gln Val Gln Leu Val Gln Ser Gly Ala Glu Ala Lys Lys Pro Gly Ala
 1               5                  10                  15 tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
             20                  25                  30 tat atg cac tgg gtg cga cag gcc cct gga caa ggg ctt gag tgg atg      144
Tyr Met His Trp Val Arg Gln Ala Pro Gly Gln Gly Leu Glu Trp Met
         35                  40                  45 gga tgg atc agc gct tac aat ggt aac aca aac tat gca cag aag ctc      192
Gly Trp Ile Ser Ala Tyr Asn Gly Asn Thr Asn Tyr Ala Gln Lys Leu
     50                  55                  60 cag ggc aga gtc acc atg acc aca gac aca tcc acg agc aca gcc tac      240
Gln Gly Arg Val Thr Met Thr Thr Asp Thr Ser Thr Ser Thr Ala Tyr
 65                  70                  75                  80 atg gag ctg agg agc ctg aga tct gac gac acg gcc gtg tat tac tgt      288
Met Glu Leu Arg Ser Leu Arg Ser Asp Asp Thr Ala Val Tyr Tyr Cys
                 85                  90                  95 gca agg tcg cag atg ccg agt tac ttt gac tac tgg ggc cag ggc acc      336
Ala Arg Ser Gln Met Pro Ser Tyr Phe Asp Tyr Trp Gly Gln Gly Thr
            100                 105                 110 ctg gtg acc gtc tcc agc                                              354
Leu Val Thr Val Ser Ser
            115

<210> SEQ ID NO 12
<211> LENGTH: 118
<212> TYPE: PRT
<213> ORGANISM: Artificial sequence
<220> FEATURE:
<223> OTHER INFORMATION: Chemically synthesized - Variable region of
      heavy chain of 02-115

<400> SEQUENCE: 12

Gln Val Gln Leu Val Gln Ser Gly Ala Glu Ala Lys Lys Pro Gly Ala
 1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45
```

```
Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Gln Met Pro Ser Tyr Phe Asp Tyr Trp Gly Gln Gly Thr
            100                 105                 110

Leu Val Thr Val Ser Ser
            115

<210> SEQ ID NO 13
<211> LENGTH: 354
<212> TYPE: DNA
<213> ORGANISM: Artificial sequence
<220> FEATURE:
<223> OTHER INFORMATION: Chemically synthesized - Variable region of
      heavy chain of 02-116
<220> FEATURE:
<221> NAME/KEY: CDS
<222> LOCATION: (1)..(354)

<400> SEQUENCE: 13 gag gtg cag ctg gtg gag tct ggg gga ggc ttg gta cag cct ggg ggg       48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45 tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60 aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80 ctg caa atg aac agc cta aga gcc gag gac acg gcc gtg tat tac tgt      288
Leu Gln Met Asn Ser Leu Arg Ala Glu Asp Thr Ala Val Tyr Tyr Cys
                85                  90                  95 gca aag gac gct ctt tgg ctg gct ttt gac tac tgg ggc cag ggc acc      336
Ala Lys Asp Ala Leu Trp Leu Ala Phe Asp Tyr Trp Gly Gln Gly Thr
            100                 105                 110 ctg gtg acc gtc tcc agc                                              354
Leu Val Thr Val Ser Ser
            115

<210> SEQ ID NO 14
<211> LENGTH: 118
<212> TYPE: PRT
<213> ORGANISM: Artificial sequence
<220> FEATURE:
<223> OTHER INFORMATION: Chemically synthesized - Variable region of
      heavy chain of 02-116

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ala Leu Trp Leu Ala Phe Asp Tyr Trp Gly Gln Gly Thr
            100                 105                 110

Leu Val Thr Val Ser Ser
            115

<210> SEQ ID NO 15
<211> LENGTH: 351
<212> TYPE: DNA
<213> ORGANISM: Artificial sequence
<220> FEATURE:
<223> OTHER INFORMATION: Chemically synthesized - Variable region of
      heavy chain of 02-117
<220> FEATURE:
<221> NAME/KEY: CDS
<222> LOCATION: (1)..(351)

<400> SEQUENCE: 15 gag gtg cag ctg gtg gag tct ggg gga ggc ttg gta cat cct ggg ggg      48
Glu Val Gln Leu Val Glu Ser Gly Gly Gly Leu Val His Pro Gly Gly
 1               5                  10                  15 tcc ctg aga ctc tcc tgt gca ggc tct gga ttc acc ttc agt agc tat      96
Ser Leu Arg Leu Ser Cys Ala Gly Ser Gly Phe Thr Phe Ser Ser Tyr
                 20                  25                  30 gct atg cac tgg gtt cgc cag gct cca gga aaa ggt ctg gag tgg gta     144
Ala Met His Trp Val Arg Gln Ala Pro Gly Lys Gly Leu Glu Trp Val
             35                  40                  45 tca gct att ggt act ggt ggt ggc aca tac tat gca gac tcc gtg aag     192
Ser Ala Ile Gly Thr Gly Gly Gly Thr Tyr Tyr Ala Asp Ser Val Lys
        50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
 65                  70                  75                  80 caa atg aac agc ctg aga gcc gag gac acg gcc gtg tat tac tgt gca     288
Gln Met Asn Ser Leu Arg Ala Glu Asp Thr Ala Val Tyr Tyr Cys Ala
                 85                  90                  95 agg tct acg cct tgg ttt tcc ttt gac tac tgg ggc cag ggc acc ctg     336
Arg Ser Thr Pro Trp Phe Ser Phe Asp Tyr Trp Gly Gln Gly Thr Leu
            100                 105                 110 gtg acc gtc tcc agc                                                 351
Val Thr Val Ser Ser
            115

<210> SEQ ID NO 16
<211> LENGTH: 117
<212> TYPE: PRT
<213> ORGANISM: Artificial sequence
<220> FEATURE:
<223> OTHER INFORMATION: Chemically synthesized - Variable region of
      heavy chain of 02-117

<400> SEQUENCE: 16

Glu Val Gln Leu Val Glu Ser Gly Gly Gly Leu Val His Pro Gly Gly
 1               5                  10                  15

Ser Leu Arg Leu Ser Cys Ala Gly Ser Gly Phe Thr Phe Ser Ser Tyr
                 20                  25                  30

Ala Met His Trp Val Arg Gln Ala Pro Gly Lys Gly Leu Glu Trp Val

```
                35                  40                  45
Ser Ala Ile Gly Thr Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Ser Thr Pro Trp Phe Ser Phe Asp Tyr Trp Gly Gln Gly Thr Leu
            100                 105                 110

Val Thr Val Ser Ser
        115

<210> SEQ ID NO 17
<211> LENGTH: 351
<212> TYPE: DNA
<213> ORGANISM: Artificial sequence
<220> FEATURE:
<223> OTHER INFORMATION: Chemically synthesized - Variable region of
      heavy chain of 02-118
<220> FEATURE:
<221> NAME/KEY: CDS
<222> LOCATION: (1)..(351)

<400> SEQUENCE: 17 gag gtg cag ctg gtg gag tct ggg gga ggc ttg gta cat cct ggg ggg      48
Glu Val Gln Leu Val Glu Ser Gly Gly Gly Leu Val His Pro Gly Gly
1               5                   10                  15 tcc ctg aga ctc tcc tgt gca ggc tct gga ttc acc ttc agt agc tat      96
Ser Leu Arg Leu Ser Cys Ala Gly Ser Gly Phe Thr Phe Ser Ser Tyr
            20                  25                  30 gct atg cac tgg gtt cgc cag gct cca gga aaa ggt ctg gag tgg gta     144
Ala Met His Trp Val Arg Gln Ala Pro Gly Lys Gly Leu Glu Trp Val
        35                  40                  45 tca gct att agt act ggt ggt ggc aca tac tat gca gac tcc gtg aag     192
Ser Ala Ile Ser Thr Gly Gly Gly Thr Tyr Tyr Ala Asp Ser Val Lys
    50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
65                  70                  75                  80 caa atg aac agc ctg aga gcc gag gac acg gcc gtg tat tac tgt gca     288
Gln Met Asn Ser Leu Arg Ala Glu Asp Thr Ala Val Tyr Tyr Cys Ala
                85                  90                  95 agg agt gct tgg tgg ctg tcc ttt gac tcc tgg ggc cag ggc acc ctg     336
Arg Ser Ala Trp Trp Leu Ser Phe Asp Ser Trp Gly Gln Gly Thr Leu
            100                 105                 110 gtg acc gtc tcc agc                                                  351
Val Thr Val Ser Ser
        115

<210> SEQ ID NO 18
<211> LENGTH: 117
<212> TYPE: PRT
<213> ORGANISM: Artificial sequence
<220> FEATURE:
<223> OTHER INFORMATION: Chemically synthesized - Variable region of
      heavy chain of 02-118

<400> SEQUENCE: 18

Glu Val Gln Leu Val Glu Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30
```

```
Ala Met His Trp Val Arg Gln Ala Pro Gly Lys Gly Leu Glu Trp Val
        35                  40                  45

Ser Ala Ile Ser Thr Gly Gly Thr Tyr Tyr Ala Asp Ser Val Lys
 50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Arg Ser Ala Trp Trp Leu Ser Phe Asp Ser Trp Gly Gln Gly Thr Leu
            100                 105                 110

Val Thr Val Ser Ser
        115

<210> SEQ ID NO 19
<211> LENGTH: 330
<212> TYPE: DNA
<213> ORGANISM: Artificial sequence
<220> FEATURE:
<223> OTHER INFORMATION: Chemically synthesized - Variable region of
      light chain of 02-113, 02-114, 02-116, 02-117 and 02-118
<220> FEATURE:
<221> NAME/KEY: CDS
<222> LOCATION: (1)..(330)

<400> SEQUENCE: 19 gac att cag atg acc cag tct cca tcc tcc ctg tct gca tct gta gga      48
Asp Ile Gln Met Thr Gln Ser Pro Ser Ser Leu Ser Ala Ser Val Gly
 1               5                  10                  15 gac aga gtc acc atc act tgc cgg gca agt cag agc att agc agc tac      96
Asp Arg Val Thr Ile Thr Cys Arg Ala Ser Gln Ser Ile Ser Ser Tyr
             20                  25                  30 tta aat tgg tat cag cag aaa cca ggg aaa gcc cct aag ctc ctg atc     144
Leu Asn Trp Tyr Gln Gln Lys Pro Gly Lys Ala Pro Lys Leu Leu Ile
         35                  40                  45 tat gct gca tcc agt ttg caa agt ggg gtc cca tca agg ttc agt ggc     192
Tyr Ala Ala Ser Ser Leu Gln Ser Gly Val Pro Ser Arg Phe Ser Gly
 50                  55                  60 agt gga tct ggg aca gat ttc act ctc acc atc agc agt ctg caa cct     240
Ser Gly Ser Gly Thr Asp Phe Thr Leu Thr Ile Ser Ser Leu Gln Pro
 65                  70                  75                  80 gaa gat ttt gca act tac tac tgt caa cag agt tac agt acc cct cca     288
Glu Asp Phe Ala Thr Tyr Tyr Cys Gln Gln Ser Tyr Ser Thr Pro Pro
                 85                  90                  95 acg ttc ggc caa ggg acc aag gtg gag atc aaa cgg acc gtg             330
Thr Phe Gly Gln Gly Thr Lys Val Glu Ile Lys Arg Thr Val
            100                 105                 110

<210> SEQ ID NO 20
<211> LENGTH: 110
<212> TYPE: PRT
<213> ORGANISM: Artificial sequence
<220> FEATURE:
<223> OTHER INFORMATION: Chemically synthesized - Variable region of
      light chain of 02-113, 02-114, 02-116, 02-117 and 02-118

<400> SEQUENCE: 20

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45
```

```
Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Thr Phe Gly Gln Gly Thr Lys Val Glu Ile Lys Arg Thr Val
             100                 105                 110

<210> SEQ ID NO 21
<211> LENGTH: 354
<212> TYPE: DNA
<213> ORGANISM: Artificial sequence
<220> FEATURE:
<223> OTHER INFORMATION: Chemically synthesized - Variable region of
      light chain of 02-115
<220> FEATURE:
<221> NAME/KEY: CDS
<222> LOCATION: (1)..(354)

<400> SEQUENCE: 21 tcc tcc gag ctg acc cag gac cct gct gtg tct gtg gcc ttg gga cag      48
Ser Ser Glu Leu Thr Gln Asp Pro Ala Val Ser Val Ala Leu Gly Gln
 1               5                  10                  15 aca gtc agg atc aca tgc caa gga gac agc ctc aga agc tat tat gca      96
Thr Val Arg Ile Thr Cys Gln Gly Asp Ser Leu Arg Ser Tyr Tyr Ala
             20                  25                  30 agc tgg tac cag cag aag cca gga cag gcc cct gta ctt gtc atc tat     144
Ser Trp Tyr Gln Gln Lys Pro Gly Gln Ala Pro Val Leu Val Ile Tyr
         35                  40                  45 ggt aaa aac aac cgg ccc tca ggg atc cca gac cga ttc tct ggc tcc     192
Gly Lys Asn Asn Arg Pro Ser Gly Ile Pro Asp Arg Phe Ser Gly Ser
     50                  55                  60 agc tca gga aac aca gct tcc ttg acc atc act ggg gct cag gcg gaa     240
Ser Ser Gly Asn Thr Ala Ser Leu Thr Ile Thr Gly Ala Gln Ala Glu
 65                  70                  75                  80 gat gag gct gac tat tac tgt aac tcc cgg gac agc agt ggt aac cat     288
Asp Glu Ala Asp Tyr Tyr Cys Asn Ser Arg Asp Ser Ser Gly Asn His
                 85                  90                  95 gtg gta ttc ggc gga ggg acc aag ctg acc gtc cta ggt gag tcg cgg     336
Val Val Phe Gly Gly Gly Thr Lys Leu Thr Val Leu Gly Glu Ser Arg
            100                 105                 110 ccg caa gct tac cgt gct                                              354
Pro Gln Ala Tyr Arg Ala
        115

<210> SEQ ID NO 22
<211> LENGTH: 118
<212> TYPE: PRT
<213> ORGANISM: Artificial sequence
<220> FEATURE:
<223> OTHER INFORMATION: Chemically synthesized - Variable region of
      light chain of 02-115

<400> SEQUENCE: 22

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
     50                  55                  60
```

```
Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Val Val Phe Gly Gly Gly Thr Lys Leu Thr Val Leu Gly Glu Ser Arg
            100                 105                 110

Pro Gln Ala Tyr Arg Ala
        115

<210> SEQ ID NO 23
<211> LENGTH: 16
<212> TYPE: DNA
<213> ORGANISM: Artificial sequence
<220> FEATURE:
<223> OTHER INFORMATION: Chemically synthesized - Primer M13rev

<400> SEQUENCE: 23
aacagctatg accatg                                                       16

<210> SEQ ID NO 24
<211> LENGTH: 17
<212> TYPE: DNA
<213> ORGANISM: Artificial sequence
<220> FEATURE:
<223> OTHER INFORMATION: Chemically synthesized - Primer fdSeq

<400> SEQUENCE: 24
gaattttctg tatgagg                                                      17

<210> SEQ ID NO 25
<211> LENGTH: 720
<212> TYPE: DNA
<213> ORGANISM: Artificial sequence
<220> FEATURE:
<223> OTHER INFORMATION: Chemically synthesized - Sequence of scFv
      SC02-113
<220> FEATURE:
<221> NAME/KEY: CDS
<222> LOCATION: (1)..(720)

<400> SEQUENCE: 25 cag gtg cag ctg cag gag tcg ggc gca gga ctg ttg aag cct tcg gag      48
Gln Val Gln Leu Gln Glu Ser Gly Ala Gly Leu Leu Lys Pro Ser Glu
 1               5                  10                  15 acc ctg tcc ctc acc tgc gct gtc tat ggt ggg tct ttc agt ggc tac      96
Thr Leu Ser Leu Thr Cys Ala Val Tyr Gly Gly Ser Phe Ser Gly Tyr
             20                  25                  30 tac tgg agc tgg atc cgg cag ccc cca ggg aag gga ctg gag tgg att     144
Tyr Trp Ser Trp Ile Arg Gln Pro Pro Gly Lys Gly Leu Glu Trp Ile
         35                  40                  45 ggg tat atc tat tac agt ggg agc acc aac tac aac ccc tcc ctc aag     192
Gly Tyr Ile Tyr Tyr Ser Gly Ser Thr Asn Tyr Asn Pro Ser Leu Lys
     50                  55                  60 agt cga gtc acc ata tca gta gac acg tcc aag aac cag ttc tcc ctg     240
Ser Arg Val Thr Ile Ser Val Asp Thr Ser Lys Asn Gln Phe Ser Leu
 65                  70                  75                  80 aag ctg agc tct gtg acc gct gcg gac acg gcc gtg tat tac tgt gca     288
Lys Leu Ser Ser Val Thr Ala Ala Asp Thr Ala Val Tyr Tyr Cys Ala
                 85                  90                  95 aag gcc cct tat atg atg tat ttt gac tcc tgg ggc caa ggt acc ctg     336
Lys Ala Pro Tyr Met Met Tyr Phe Asp Ser Trp Gly Gln Gly Thr Leu
            100                 105                 110 gtc acc gtc tcg agt ggt gga ggc ggt tca ggc gga ggt ggc tct ggc     384
```

```
Val Thr Val Ser Ser Gly Gly Gly Ser Gly Gly Gly Ser Gly
        115                 120                 125 ggt ggc gga tcg gaa att gag ctc acc cag tct cca tcc tcc ctg tct      432
Gly Gly Gly Ser Glu Ile Glu Leu Thr Gln Ser Pro Ser Ser Leu Ser
130                 135                 140 gca tct gta gga gac aga gtc acc atc act tgc cgg gca agt cag agc      480
Ala Ser Val Gly Asp Arg Val Thr Ile Thr Cys Arg Ala Ser Gln Ser
145                 150                 155                 160 att agc agc tac tta aat tgg tat cag cag aaa cca ggg aaa gcc cct      528
Ile Ser Ser Tyr Leu Asn Trp Tyr Gln Gln Lys Pro Gly Lys Ala Pro
                165                 170                 175 aag ctc ctg atc tat gct gca tcc agt ttg caa agt ggg gtc cca tca      576
Lys Leu Leu Ile Tyr Ala Ala Ser Ser Leu Gln Ser Gly Val Pro Ser
            180                 185                 190 agg ttc agt ggc agt gga tct ggg aca gat ttc act ctc acc atc agc      624
Arg Phe Ser Gly Ser Gly Ser Gly Thr Asp Phe Thr Leu Thr Ile Ser
        195                 200                 205 agt ctg caa cct gaa gat ttt gca act tac tac tgt caa cag agt tac      672
Ser Leu Gln Pro Glu Asp Phe Ala Thr Tyr Tyr Cys Gln Gln Ser Tyr
    210                 215                 220 agt acc cct cca acg ttc ggc caa ggg acc aag gtg gag atc aaa cgt      720
Ser Thr Pro Pro Thr Phe Gly Gln Gly Thr Lys Val Glu Ile Lys Arg
225                 230                 235                 240

<210> SEQ ID NO 26
<211> LENGTH: 240
<212> TYPE: PRT
<213> ORGANISM: Artificial sequence
<220> FEATURE:
<223> OTHER INFORMATION: Chemically synthesized - Sequence of scFv
      SC02-113

<400> SEQUENCE: 26

Gln Val Gln Leu Gln Glu Ser Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Ala Pro Tyr Met Met Tyr Phe Asp Ser Trp Gly Gln Gly Thr Leu
            100                 105                 110

Val Thr Val Ser Ser Gly Gly Gly Ser Gly Gly Gly Ser Gly
        115                 120                 125

Gly Gly Gly Ser Glu Ile Glu Leu Thr Gln Ser Pro Ser Ser Leu Ser
130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205
```

```
Ser Leu Gln Pro Glu Asp Phe Ala Thr Tyr Tyr Cys Gln Gln Ser Tyr
    210                 215                 220

Ser Thr Pro Pro Thr Phe Gly Gln Gly Thr Lys Val Glu Ile Lys Arg
225                 230                 235                 240

<210> SEQ ID NO 27
<211> LENGTH: 723
<212> TYPE: DNA
<213> ORGANISM: Artificial sequence
<220> FEATURE:
<223> OTHER INFORMATION: Chemically synthesized - Sequence of scFv
      SC02-114
<220> FEATURE:
<221> NAME/KEY: CDS
<222> LOCATION: (1)..(723)

<400> SEQUENCE: 27 gag gtg cag ctg gtg gag tct ggg gga ggc ttg gta cag cct ggg ggg        48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttc agt agc tat        96
Ser Leu Arg Leu Ser Cys Ala Ala Ser Gly Phe Thr Phe Ser Ser Tyr
            20                  25                  30 agc atg aac tgg gtc cgc cag gct cca ggg aag ggg ctg gag tgg gtt       144
Ser Met Asn Trp Val Arg Gln Ala Pro Gly Lys Gly Leu Glu Trp Val
        35                  40                  45 tca tac att agt agt agt agt agt acc ata tac tac gca gac tct gtg       192
Ser Tyr Ile Ser Ser Ser Ser Ser Thr Ile Tyr Tyr Ala Asp Ser Val
    50                  55                  60 aag ggc cga ttc acc atc tcc aga gac aat gcc aag aac tca ctg tat       240
Lys Gly Arg Phe Thr Ile Ser Arg Asp Asn Ala Lys Asn Ser Leu Tyr
65                  70                  75                  80 ctg caa atg aac agc ctg aga gac gag gac acg gcc gtg tat tac tgt       288
Leu Gln Met Asn Ser Leu Arg Asp Glu Asp Thr Ala Val Tyr Tyr Cys
                85                  90                  95 gca aag gag act tgg tgg cag tcc ttt gac tac tgg ggc caa ggt acc       336
Ala Lys Glu Thr Trp Trp Gln Ser Phe Asp Tyr Trp Gly Gln Gly Thr
            100                 105                 110 ctg gtc acc gtc tcg agt ggt gga ggc ggt tca ggc gga ggt ggc tct       384
Leu Val Thr Val Ser Ser Gly Gly Gly Gly Ser Gly Gly Gly Gly Ser
        115                 120                 125 ggc ggt ggc gga tcg gaa att gag ctc acc cag tct cca tcc tcc ctg       432
Gly Gly Gly Gly Ser Glu Ile Glu Leu Thr Gln Ser Pro Ser Ser Leu
    130                 135                 140 tct gca tct gta gga gac aga gtc acc atc act tgc cgg gca agt cag       480
Ser Ala Ser Val Gly Asp Arg Val Thr Ile Thr Cys Arg Ala Ser Gln
145                 150                 155                 160 agc att agc agc tac tta aat tgg tat cag cag aaa cca ggg aaa gcc       528
Ser Ile Ser Ser Tyr Leu Asn Trp Tyr Gln Gln Lys Pro Gly Lys Ala
                165                 170                 175 cct aag ctc ctg atc tat gct gca tcc agt ttg caa agt ggg gtc cca       576
Pro Lys Leu Leu Ile Tyr Ala Ala Ser Ser Leu Gln Ser Gly Val Pro
            180                 185                 190 tca agg ttc agt ggc agt gga tct ggg aca gat ttc act ctc acc atc       624
Ser Arg Phe Ser Gly Ser Gly Ser Gly Thr Asp Phe Thr Leu Thr Ile
        195                 200                 205 agc agt ctg caa cct gaa gat ttt gca act tac tac tgt caa cag agt       672
Ser Ser Leu Gln Pro Glu Asp Phe Ala Thr Tyr Tyr Cys Gln Gln Ser
    210                 215                 220 tac agt acc cct cca acg ttc ggc caa ggg acc aag gtg gag atc aaa       720
Tyr Ser Thr Pro Pro Thr Phe Gly Gln Gly Thr Lys Val Glu Ile Lys
225                 230                 235                 240
``` cgt                                                                     723
Arg

<210> SEQ ID NO 28
<211> LENGTH: 241
<212> TYPE: PRT
<213> ORGANISM: Artificial sequence
<220> FEATURE:
<223> OTHER INFORMATION: Chemically synthesized - Sequence of scFv
      SC02-114

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Lys Glu Thr Trp Trp Gln Ser Phe Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Glu Ile Glu Leu Thr Gln Ser Pro Ser Ser Leu
130                 135                 140

Ser Ala Ser Val Gly Asp Arg Val Thr Ile Thr Cys Arg Ala Ser Gln
145                 150                 155                 160

Ser Ile Ser Ser Tyr Leu Asn Trp Tyr Gln Gln Lys Pro Gly Lys Ala
                165                 170                 175

Pro Lys Leu Leu Ile Tyr Ala Ala Ser Ser Leu Gln Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Tyr Cys Gln Gln Ser
210                 215                 220

Tyr Ser Thr Pro Pro Thr Phe Gly Gln Gly Thr Lys Val Glu Ile Lys
225                 230                 235                 240

Arg

<210> SEQ ID NO 29
<211> LENGTH: 723
<212> TYPE: DNA
<213> ORGANISM: Artificial sequence
<220> FEATURE:
<223> OTHER INFORMATION: Chemically synthesized - Sequence of scFv
      SC02-115

<400> SEQUENCE: 29
caggtgcagc tggtgcagtc tggggctgag gcgaagaagc ctggggcctc agtgaaggtc      60
tcctgcaagg cttctggata caccttcacc ggctactata tgcactgggt gcgacaggcc    120
cctggacaag gcttgagtg gatgggatgg atcagcgctt acaatggtaa cacaaactat     180
gcacagaagc tccagggcag agtcaccatg accacagaca catccacgag cacagcctac    240

```
atggagctga ggagcctgag atctgacgac acggccgtgt attactgtgc aaggtcgtag   300
atgccgagtt actttgacta ctggggccaa ggtaccctgg tcaccgtctc gagaggtgga   360
ggcggttcag gcggaggtgg ctctggcggt ggcggatcgt ctgagctgac tcaggaccct   420
gctgtgtctg tggccttggg acagacagtc aggatcacat gccaaggaga cagcctcaga   480
agctattatg caagctggta ccagcagaag ccaggacagg cccctgtact tgtcatctat   540
ggtaaaaaca accggccctc aggatcccca gaccgattct ctggctccag ctcaggaaac   600
acagcttcct tgaccatcac tgggctcagg cggaagatg aggctgacta ttactgtaac   660
tcccgggaca gcagtggtaa ccatgtggta ttcggcggag ggaccaagct gaccgtccta   720
ggt                                                                 723
```

<210> SEQ ID NO 30
<211> LENGTH: 241
<212> TYPE: PRT
<213> ORGANISM: Artificial sequence
<220> FEATURE:
<223> OTHER INFORMATION: Chemically synthesized - Sequence of scFv SC02-115

<400> SEQUENCE: 30

```
Gln Val Gln Leu Val Gln Ser Gly Ala Glu Ala Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Gln Met Pro Ser Tyr Phe Asp Tyr Trp Gly Gln Gly Thr
            100                 105                 110

Leu Val Thr Val Ser Arg Gly Gly Gly Gly Ser Gly Gly Gly Gly Ser
        115                 120                 125

Gly Gly Gly Gly Ser Ser Glu Leu Thr Gln Asp Pro Ala Val Ser Val
    130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
            180                 185                 190

Phe Ser Gly Ser Ser Ser Gly Asn Thr Ala Ser Leu Thr Ile Thr Gly
        195                 200                 205

Ala Gln Ala Glu Asp Glu Ala Asp Tyr Tyr Cys Asn Ser Arg Asp Ser
    210                 215                 220

Ser Gly Asn His Val Val Phe Gly Gly Gly Thr Lys Leu Thr Val Leu
225                 230                 235                 240

Gly
```

<210> SEQ ID NO 31
<211> LENGTH: 723

<212> TYPE: DNA
<213> ORGANISM: Artificial sequence
<220> FEATURE:
<223> OTHER INFORMATION: Chemically synthesized - Sequence of scFv SC02-116
<220> FEATURE:
<221> NAME/KEY: CDS
<222> LOCATION: (1)..(723)

<400> SEQUENCE: 31

```
gag gtg cag ctg gtg gag tct ggg gga ggc ttg gta cag cct ggg ggg    48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agc agc tat    96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc   144
Ala Met Ser Trp Val Arg Gln Ala Pro Gly Lys Gly Leu Glu Trp Val
        35                  40                  45 tca gct att agt ggt agt ggt ggt agc aca tac tac gca gac tcc gtg   192
Ser Ala Ile Ser Gly Ser Gly Gly Ser Thr Tyr Tyr Ala Asp Ser Val
    50                  55                  60 aag ggc cgg ttc acc atc tcc aga gac aat tcc aag aac acg ctg tat   240
Lys Gly Arg Phe Thr Ile Ser Arg Asp Asn Ser Lys Asn Thr Leu Tyr
65                  70                  75                  80 ctg caa atg aac agc cta aga gcc gag gac acg gcc gtg tat tac tgt   288
Leu Gln Met Asn Ser Leu Arg Ala Glu Asp Thr Ala Val Tyr Tyr Cys
                85                  90                  95 gca aag gac gct ctt tgg ctg gct ttt gac tac tgg ggc caa ggt acc   336
Ala Lys Asp Ala Leu Trp Leu Ala Phe Asp Tyr Trp Gly Gln Gly Thr
            100                 105                 110 ctg gtc acc gtc tcg agt ggt gga ggc ggt tca ggc gga ggt ggc tct   384
Leu Val Thr Val Ser Ser Gly Gly Gly Gly Ser Gly Gly Gly Gly Ser
        115                 120                 125 ggc ggt ggc gga tcg gaa att gag ctc acc cag tct cca tcc tcc ctg   432
Gly Gly Gly Gly Ser Glu Ile Glu Leu Thr Gln Ser Pro Ser Ser Leu
    130                 135                 140 tct gca tct gta gga gac aga gtc acc atc act tgc cgg gca agt cag   480
Ser Ala Ser Val Gly Asp Arg Val Thr Ile Thr Cys Arg Ala Ser Gln
145                 150                 155                 160 agc att agc agc tat tta aat tgg tat cag cag aaa cca ggg aaa gcc   528
Ser Ile Ser Ser Tyr Leu Asn Trp Tyr Gln Gln Lys Pro Gly Lys Ala
                165                 170                 175 cct aag ctc ctg atc tat gct gca tcc agt ttg caa agt ggg gtc cca   576
Pro Lys Leu Leu Ile Tyr Ala Ala Ser Ser Leu Gln Ser Gly Val Pro
            180                 185                 190 tca agg ttc agt ggc agt gga tct ggg aca gat ttc act ctc acc atc   624
Ser Arg Phe Ser Gly Ser Gly Ser Gly Thr Asp Phe Thr Leu Thr Ile
        195                 200                 205 agc agt ctg caa cct gaa gat ttt gca act tac tac tgt gct cag agg   672
Ser Ser Leu Gln Pro Glu Asp Phe Ala Thr Tyr Tyr Cys Ala Gln Arg
    210                 215                 220 agt tat ccg cct cct aag ttc ggc caa ggg acc aag gtg gat atc aaa   720
Ser Tyr Pro Pro Pro Lys Phe Gly Gln Gly Thr Lys Val Asp Ile Lys
225                 230                 235                 240 cgt                                                                723
Arg

<210> SEQ ID NO 32
<211> LENGTH: 241
<212> TYPE: PRT
<213> ORGANISM: Artificial sequence
<220> FEATURE:
```

<223> OTHER INFORMATION: Chemically synthesized - Sequence of scFv
      SC02-116

<400> SEQUENCE: 32

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ala Leu Trp Leu Ala Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Glu Leu Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Ser Ile Ser Ser Tyr Leu Asn Trp Tyr Gln Gln Lys Pro Gly Lys Ala
                165                 170                 175

Pro Lys Leu Leu Ile Tyr Ala Ala Ser Ser Leu Gln Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Tyr Cys Ala Gln Arg
    210                 215                 220

Ser Tyr Pro Pro Pro Lys Phe Gly Gln Gly Thr Lys Val Asp Ile Lys
225                 230                 235                 240

Arg
```

<210> SEQ ID NO 33
<211> LENGTH: 720
<212> TYPE: DNA
<213> ORGANISM: Artificial sequence
<220> FEATURE:
<223> OTHER INFORMATION: Chemically synthesized - Sequence of scFv
      SC02-117
<220> FEATURE:
<221> NAME/KEY: CDS
<222> LOCATION: (1)..(720)

<400> SEQUENCE: 33

```
gag gtg cag ctg gtg gag tct ggg gga ggc ttg gta cat cct ggg ggg      48
Glu Val Gln Leu Val Glu Ser Gly Gly Gly Leu Val His Pro Gly Gly
1               5                   10                  15 tcc ctg aga ctc tcc tgt gca ggc tct gga ttc acc ttc agt agc tat      96
Ser Leu Arg Leu Ser Cys Ala Gly Ser Gly Phe Thr Phe Ser Ser Tyr
            20                  25                  30 gct atg cac tgg gtt cgc cag gct cca gga aaa ggt ctg gag tgg gta     144
Ala Met His Trp Val Arg Gln Ala Pro Gly Lys Gly Leu Glu Trp Val
        35                  40                  45 tca gct att ggt act ggt ggt ggc aca tac tat gca gac tcc gtg aag     192
Ser Ala Ile Gly Thr Gly Gly Gly Thr Tyr Tyr Ala Asp Ser Val Lys
```

```
                50                   55                   60
ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
 65                  70                  75                  80 caa atg aac agc ctg aga gcc gag gac acg gcc gtg tat tac tgt gca     288
Gln Met Asn Ser Leu Arg Ala Glu Asp Thr Ala Val Tyr Tyr Cys Ala
                 85                  90                  95 agg tct acg cct tgg ttt tcc ttt gac tac tgg ggc caa ggt acc ctg     336
Arg Ser Thr Pro Trp Phe Ser Phe Asp Tyr Trp Gly Gln Gly Thr Leu
                100                 105                 110 gtc acc gtc tcg agt ggt gga ggc ggt tca ggc gga ggt ggc tct ggc     384
Val Thr Val Ser Ser Gly Gly Gly Gly Ser Gly Gly Gly Gly Ser Gly
                115                 120                 125 ggt ggc gga tcg gaa att gag ctc acc cag tct cca tcc tcc ctg tct     432
Gly Gly Gly Ser Glu Ile Glu Leu Thr Gln Ser Pro Ser Ser Leu Ser
130                 135                 140 gca tct gta gga gac aga gtc acc atc act tgc cgg gca agt cag agc     480
Ala Ser Val Gly Asp Arg Val Thr Ile Thr Cys Arg Ala Ser Gln Ser
145                 150                 155                 160 att agc agc tac tta aat tgg tat cag cag aaa cca ggg aaa gcc cct     528
Ile Ser Ser Tyr Leu Asn Trp Tyr Gln Gln Lys Pro Gly Lys Ala Pro
                165                 170                 175 aag ctc ctg atc tat gct gca tcc agt ttg caa agt ggg gtc cca tca     576
Lys Leu Leu Ile Tyr Ala Ala Ser Ser Leu Gln Ser Gly Val Pro Ser
                180                 185                 190 agg ttc agt ggc agt gga tct ggg aca gat ttc act ctc acc atc agc     624
Arg Phe Ser Gly Ser Gly Ser Gly Thr Asp Phe Thr Leu Thr Ile Ser
                195                 200                 205 agt ctg caa cct gaa gat ttt gca act tac tac tgt caa cag agt tac     672
Ser Leu Gln Pro Glu Asp Phe Ala Thr Tyr Tyr Cys Gln Gln Ser Tyr
210                 215                 220 agt acc cct cca acg ttc ggc caa ggg acc aag gtg gag atc aaa cgt     720
Ser Thr Pro Pro Thr Phe Gly Gln Gly Thr Lys Val Glu Ile Lys Arg
225                 230                 235                 240

<210> SEQ ID NO 34
<211> LENGTH: 240
<212> TYPE: PRT
<213> ORGANISM: Artificial sequence
<220> FEATURE:
<223> OTHER INFORMATION: Chemically synthesized - Sequence of scFv
      SC02-117

<400> SEQUENCE: 34

Glu Val Gln Leu Val Glu Ser Gly Gly Gly Leu Val His Pro Gly Gly
 1               5                  10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Arg Ser Thr Pro Trp Phe Ser Phe Asp Tyr Trp Gly Gln Gly Thr Leu
                100                 105                 110

Val Thr Val Ser Ser Gly Gly Gly Gly Ser Gly Gly Gly Gly Ser Gly
                115                 120                 125
```

```
Gly Gly Gly Ser Glu Ile Glu Leu Thr Gln Ser Pro Ser Ser Leu Ser
        130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Tyr
    210                 215                 220

Ser Thr Pro Pro Thr Phe Gly Gln Gly Thr Lys Val Glu Ile Lys Arg
225                 230                 235                 240
```

<210> SEQ ID NO 35
<211> LENGTH: 720
<212> TYPE: DNA
<213> ORGANISM: Artificial sequence
<220> FEATURE:
<223> OTHER INFORMATION: Chemically synthesized - Sequence of scFv SC02-118

<400> SEQUENCE: 35

```
gaggtgcagc tggtggagtc tgggggaggc taggtacatc ctggggggtc cctgagactc    60
tcctgtgcag gctctggatt caccttcagt agctatgcta tgcactgggt tcgccaggct   120
ccaggaaaag gtctggagtg gtatcagct attagtactg gtggtggcac atactatgca   180
gactccgtga aggccgatt caccatctcc agagacaatg ccaagaactc cttgtatctt   240
caaatgaaca gcctgagagc cgaggacacg gccgtgtatt actgtgcaag gagtgcttgg   300
tggctgtcct ttgactcctg gggccaaggt accctggtca ccgtctcgag tggtggaggc   360
ggttcaggcg gaggtggctc tggcggtggc ggatcggaaa ttgagctcac ccagtctcca   420
tcctccctgt ctgcatctgt aggagacaga gtcaccatca cttgccgggc aagtcagagc   480
attagcagct acttaaattg gtatcagcag aaaccaggga agcccctaa gctcctgatc   540
tatgctgcat ccagtttgca aagtggggtc ccatcaaggt tcagtggcag tggatctggg   600
acagatttca ctctcaccat cagcagtctg caacctgaag attttgcaac ttactactgt   660
caacagagtt acagtacccc tccaacgttc ggccaaggga ccaaggtgga gatcaaacgt   720
```

<210> SEQ ID NO 36
<211> LENGTH: 240
<212> TYPE: PRT
<213> ORGANISM: Artificial sequence
<220> FEATURE:
<223> OTHER INFORMATION: Chemically synthesized - Sequence of scFv SC02-118

<400> SEQUENCE: 36

```
Glu Val Gln Leu Val Glu Ser Gly Gly Gly Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Thr Gly Gly Gly Thr Tyr Tyr Ala Asp Ser Val Lys
    50                  55                  60
```

```
Gly Arg Phe Thr Ile Ser Arg Asp Asn Ala Lys Asn Ser Leu Tyr Leu
 65                  70                  75                  80
Gln Met Asn Ser Leu Arg Ala Glu Asp Thr Ala Val Tyr Tyr Cys Ala
                 85                  90                  95
Arg Ser Ala Trp Trp Leu Ser Phe Asp Ser Trp Gly Gln Gly Thr Leu
            100                 105                 110
Val Thr Val Ser Ser Gly Gly Gly Gly Ser Gly Gly Gly Ser Gly
        115                 120                 125
Gly Gly Gly Ser Glu Ile Glu Leu Thr Gln Ser Pro Ser Ser Leu Ser
130                 135                 140
Ala Ser Val Gly Asp Arg Val Thr Ile Thr Cys Arg Ala Ser Gln Ser
145                 150                 155                 160
Ile Ser Ser Tyr Leu Asn Trp Tyr Gln Gln Lys Pro Gly Lys Ala Pro
                165                 170                 175
Lys Leu Leu Ile Tyr Ala Ala Ser Ser Leu Gln Ser Gly Val Pro Ser
            180                 185                 190
Arg Phe Ser Gly Ser Gly Ser Gly Thr Asp Phe Thr Leu Thr Ile Ser
        195                 200                 205
Ser Leu Gln Pro Glu Asp Phe Ala Thr Tyr Tyr Cys Gln Gln Ser Tyr
210                 215                 220
Ser Thr Pro Pro Thr Phe Gly Gln Gly Thr Lys Val Glu Ile Lys Arg
225                 230                 235                 240

<210> SEQ ID NO 37
<211> LENGTH: 6778
<212> TYPE: DNA
<213> ORGANISM: Artificial sequence
<220> FEATURE:
<223> OTHER INFORMATION: Chemically synthesized - pSyn-C03-HCgamma1

<400> SEQUENCE: 37
gacggatcgg gagatctccc gatccctat  ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgct aggtggtcaa tattggccat agccatatt    240
attcattggt tatatagcat aaatcaatat tggctattgg ccattgcata cgttgtatcc    300
atatcataat atgtacattt atattggctc atgtccaaca ttaccgccat gttgacattg    360
attattgact agttattaat agtaatcaat tacgggtca ttagttcata gcccatatat    420
ggagttccgc gttacataac ttacggtaaa tggcccgcct ggctgaccgc ccaacgaccc    480
ccgcccattg acgtcaataa tgacgtatgt tcccatagta acgccaatag ggactttcca    540
ttgacgtcaa tgggtggagt atttacggta aactgcccac ttggcagtac atcaagtgta    600
tcatatgcca agtacgcccc ctattgacgt caatgacggt aaatggcccg cctggcatta    660
tgcccagtac atgaccttat gggactttcc tacttggcag tacatctacg tattagtcat    720
cgctattacc atggtgatgc ggttttggca gtacatcaat gggcgtggat agcggtttga    780
ctcacgggga tttccaagtc tccacccat gacgtcaat gggagtttgt tttggcacca    840
aaatcaacgg gactttccaa atgtcgtaa caactccgcc ccattgacgc aaatgggcgg    900
taggcgtgta cggtgggagg tctatataag cagagctcgt ttagtgaacc gtcagatcgc    960
ctggagacgc catccacgct gttttgacct ccatagaaga caccgggacc gatccagcct   1020
ccgcggccgg gaacgtgca ttggaagctg gcctggatgg cctgactctc ttaggtagcc   1080
ttgcagaagt tggtcgtgag gcactgggca ggtaagtatc aaggttacaa gacaggttta   1140
```

```
aggagatcaa tagaaactgg gcttgtcgag acagagaaga ctcttgcgtt tctgataggc    1200
acctattggt cttactgaca tccactttgc ctttctctcc acaggtgtcc actcccagtt    1260
caattacagc tcgccaccat ggcctgcccc ggcttcctgt gggccctggt gatcagcacc    1320
tgcctggaat tcagcatgag cagcgctagc accaagggcc ccagcgtgtt cccctggcc    1380 cccagcagca agagcaccag cggcggcaca gccgccctgg gctgcctggt gaaggactac    1440
ttccccgagc ccgtgaccgt gagctggaac agcggcgcct tgaccagcgg cgtgcacacc    1500
ttccccgccg tgctgcagag cagcggcctg tacagcctga gcagcgtggt gaccgtgccc    1560
agcagcagcc tgggcaccca gacctacatc tgcaacgtga accacaagcc cagcaacacc    1620
aaggtggaca acgcgtggag cccaagagc tgcgacaaga cccacacctg ccccccctgc    1680 cctgccccg agctgctggg cggacccctcc gtgttcctgt tcccccccaa gcccaaggac    1740
accctcatga tcagccggac ccccgaggtg acctgcgtgg tggtggacgt gagccacgag    1800
gaccccgagg tgaagttcaa ctggtacgtg gacggcgtgg aggtgcacaa cgccaagacc    1860
aagccccggg aggagcagta caacagcacc taccgggtgg tgagcgtgct caccgtgctg    1920
caccaggact ggctgaacgg caaggagtac aagtgcaagg tgagcaacaa ggccctgcct    1980
gcccccatcg agaagaccat cagcaaggcc aagggccagc ccgggagcc ccaggtgtac    2040 accctgcccc ccagccggga ggagatgacc aagaaccagg tgtccctcac ctgtctggtg    2100
aagggcttct accccagcga catcgccgtg gagtgggaga gcaacggcca gcccgagaac    2160
aactacaaga ccacccccc tgtgctggac agcgacggca gcttcttcct gtacagcaag    2220
ctcaccgtgg acaagagccg gtggcagcag ggcaacgtgt tcagctgcag cgtgatgcac    2280
gaggccctgc acaaccacta cacccagaag agcctgagcc tgagccccgg caagtgataa    2340
tctagagggc ccgtttaaac ccgctgatca gcctcgactg tgccttctag ttgccagcca    2400
tctgttgttt gcccctcccc cgtgccttcc ttgaccctgg aaggtgccac tcccactgtc    2460
ctttcctaat aaaatgagga aattgcatcg cattgtctga gtaggtgtca ttctattctg    2520
gggggtgggg tggggcagga cagcaagggg gaggattggg aagacaatag caggcatgct    2580
ggggatgcgg tgggctctat ggcttctgag gcggaaagaa ccagctgggg ctctagggggg    2640 tatccccacg cgccctgtag cggcgcatta agcgcggcgg gtgtggtggt tacgcgcagc    2700
gtgaccgcta cacttgccag cgccctagcg cccgctcctt tcgctttctt cccttccttt    2760
ctcgccacgt tcgccggctt tccccgtcaa gctctaaatc gggggctccc tttagggttc    2820
cgatttagtg ctttacggca cctcgacccc aaaaaacttg attagggtga tggttcacgt    2880
agtgggccat cgccctgata gacggttttt cgccctttga cgttggagtc acgttctttt    2940
aatagtggac tcttgttcca aactggaaca acactcaacc ctatctcggt ctattctttt    3000
gatttataag ggattttgcc gatttcggcc tattggttaa aaaatgagct gatttaacaa    3060
aaatttaacg cgaattaatt ctgtggaatg tgtgtcagtt agggtgtgga aagtccccag    3120 gctcccagc aggcagaagt atgcaaagca tgcatctcaa ttagtcagca accaggtgtg    3180
gaaagtcccc aggctcccca gcaggcagaa gtatgcaaag catgcatctc aattagtcag    3240
caaccatagt cccgccccta actccgccca tcccgcccct aactccgccc agttccgccc    3300
attctccgcc ccatgctga ctaattttt ttatttatgc agaggccgag gccgcctctg    3360
cctctgagct attccagaag tagtgaggag gcttttttgg aggcctaggc ttttgcaaaa    3420
agctcccggg agcttgtata tccatttttcg gatctgatca agagacagga tgaggatcgt    3480
ttcgcatgat tgaacaagat ggattgcacg caggttctcc ggccgcttgg gtggagaggc    3540
```

```
tattcggcta tgactgggca caacagacaa tcggctgctc tgatgccgcc gtgttccggc   3600
tgtcagcgca ggggcgcccg gttcttttg tcaagaccga cctgtccggt gccctgaatg    3660
aactgcagga cgaggcagcg cggctatcgt ggctggccac gacgggcgtt ccttgcgcag   3720
ctgtgctcga cgttgtcact gaagcgggaa gggactggct gctattgggc gaagtgccgg   3780
ggcaggatct cctgtcatct caccttgctc ctgccgagaa agtatccatc atggctgatg   3840
caatgcggcg gctgcatacg cttgatccgg ctacctgccc attcgaccac caagcgaaac   3900
atcgcatcga gcgagcacgt actcggatgg aagccggtct tgtcgatcag gatgatctgg   3960
acgaagagca tcagggctc gcgccagccg aactgttcgc caggctcaag gcgcgcatgc    4020
ccgacggcga ggatctcgtc gtgacccatg gcgatgcctg cttgccgaat atcatggtgg   4080
aaaatggccg cttttctgga ttcatcgact gtggccggct gggtgtggcg gatcgctatc   4140
aggacatagc gttggctacc cgtgatattg ctgaagagct tggcggcgaa tgggctgacc   4200
gcttcctcgt gctttacggt atcgccgctc ccgattcgca gcgcatcgcc ttctatcgcc   4260
ttcttgacga gttcttctga gcgggactct ggggttcgaa atgaccgacc aagcgacgcc   4320
caacctgcca tcacgagatt tcgattccac cgccgccttc tatgaaaggt tgggcttcgg   4380
aatcgttttc cgggacgccg gctggatgat cctccagcgc ggggatctca tgctggagtt   4440
cttcgcccac cccaacttgt ttattgcagc ttataatggt tacaaataaa gcaatagcat   4500
cacaaatttc acaaataaag catttttttc actgcattct agttgtggtt tgtccaaact   4560
catcaatgta tcttatcatg tctgtatacc gtcgacctct agctagagct tggcgtaatc   4620
atggtcatag ctgtttcctg tgtgaaattg ttatccgctc acaattccac acaacatacg   4680
agccggaagc ataaagtgta aagcctgggg tgcctaatga gtgagctaac tcacattaat   4740
tgcgttgcgc tcactgcccg ctttccagtc gggaaacctg tcgtgccagc tgcattaatg   4800
aatcggccaa cgcgcgggga gaggcggttt gcgtattggg cgctcttccg cttcctcgct   4860
cactgactcg ctgcgctcgg tcgttcggct gcggcgagcg gtatcagctc actcaaaggc   4920
ggtaatacgg ttatccacag aatcagggga taacgcagga agaacatgt gagcaaaagg    4980 ccagcaaaag gccaggaacc gtaaaaaggc cgcgttgctg gcgtttttcc ataggctccg   5040
cccccctgac gagcatcaca aaaatcgacg ctcaagtcag aggtggcgaa acccgacagg   5100
actataaaga taccaggcgt ttccccctgg aagctccctc gtgcgctctc ctgttccgac   5160
cctgccgctt accggatacc tgtccgcctt tctcccttcg ggaagcgtgg cgctttctca   5220
tagctcacgc tgtaggtatc tcagttcggt gtaggtcgtt cgctccaagc tgggctgtgt   5280
gcacgaaccc cccgttcagc ccgaccgctg cgccttatcc ggtaactatc gtcttgagtc   5340
caacccggta agacacgact tatcgccact ggcagcagcc actggtaaca ggattagcag   5400
agcgaggtat gtaggcggtg ctacagagtt cttgaagtgg tggcctaact acggctacac   5460
tagaagaaca gtatttggta tctgcgctct gctgaagcca gttaccttcg gaaaaagagt   5520
tggtagctct tgatccggca aacaaaccac cgctggtagc ggtttttttg tttgcaagca   5580
gcagattacg cgcagaaaaa aaggatctca agaagatcct ttgatctttt ctacgggtc    5640 tgacgctcag tggaacgaaa actcacgtta agggattttg gtcatgagat tatcaaaaag   5700
gatcttcacc tagatccttt taaattaaaa atgaagtttt aaatcaatct aaagtatata   5760
tgagtaaact tggtctgaca gttaccaatg cttaatcagt gaggcaccta tctcagcgat   5820
ctgtctattt cgttcatcca tagttgcctg actccccgtc gtgtagataa ctacgatacg   5880
ggagggctta ccatctggcc ccagtgctgc aatgataccg cgagacccac gctcaccggc   5940
```

-continued

| | |
|---|---|
| tccagattta tcagcaataa accagccagc cggaagggcc gagcgcagaa gtggtcctgc | 6000 |
| aactttatcc gcctccatcc agtctattaa ttgttgccgg gaagctagag taagtagttc | 6060 |
| gccagttaat agtttgcgca acgttgttgc cattgctaca ggcatcgtgg tgtcacgctc | 6120 |
| gtcgtttggt atggcttcat tcagctccgg ttcccaacga tcaaggcgag ttacatgatc | 6180 |
| ccccatgttg tgcaaaaaag cggttagctc cttcggtcct ccgatcgttg tcagaagtaa | 6240 |
| gttggccgca gtgttatcac tcatggttat ggcagcactg cataattctc ttactgtcat | 6300 |
| gccatccgta agatgctttt ctgtgactgg tgagtactca accaagtcat tctgagaata | 6360 |
| gtgtatgcgg cgaccgagtt gctcttgccc ggcgtcaata cgggataata ccgcgccaca | 6420 |
| tagcagaact ttaaaagtgc tcatcattgg aaaacgttct cggggcgaaa actctcaag | 6480 |
| gatcttaccg ctgttgagat ccagttcgat gtaacccact cgtgcaccca actgatcttc | 6540 |
| agcatctttt actttcacca gcgtttctgg gtgagcaaaa acaggaaggc aaaatgccgc | 6600 |
| aaaaaaggga taagggcga cacggaaatg ttgaatactc atactcttcc tttttcaata | 6660 |
| ttattgaagc atttatcagg gttattgtct catgagcgga tacatatttg aatgtattta | 6720 |
| gaaaaataaa caaatagggg ttccgcgcac atttccccga aaagtgccac ctgacgtc | 6778 |

<210> SEQ ID NO 38
<211> LENGTH: 6267
<212> TYPE: DNA
<213> ORGANISM: Artificial sequence
<220> FEATURE:
<223> OTHER INFORMATION: Chemically synthesized - pSyn-C05-Ckappa

<400> SEQUENCE: 38

| | |
|---|---|
| gacggatcgg gagatctccc gatccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag cttgaccga caattgttaa ttaacatgaa | 180 |
| gaatctgctt agggttaggc gttttgcgct gcttcgctag gtggtcaata ttggccatta | 240 |
| gccatattat tcattggtta tagcataaa atcaatattg gctattggcc attgcatacg | 300 |
| ttgtatccat atcataatat gtacatttat attggctcat gtccaacatt accgccatgt | 360 |
| tgacattgat tattgactag ttattaatag taatcaatta cggggtcatt agttcatagc | 420 |
| ccatatatgg agttccgcgt tacataactt acggtaaatg gcccgcctgg ctgaccgccc | 480 |
| aacgaccccc gcccattgac gtcaataatg acgtatgttc ccatagtaac gccaataggg | 540 |
| actttccatt gacgtcaatg ggtggagtat ttacggtaaa ctgcccactt ggcagtacat | 600 |
| caagtgtatc atatgccaag tacgcccct attgacgtca atgacggtaa atggcccgcc | 660 |
| tggcattatg cccagtacat gaccttatgg gactttccta cttggcagta catctacgta | 720 |
| ttagtcatcg ctattaccat ggtgatgcgg ttttggcagt acatcaatgg gcgtggatag | 780 |
| cggtttgact cacggggatt tccaagtctc caccccattg acgtcaatgg gagtttgttt | 840 |
| tggcaccaaa atcaacggga ctttccaaaa tgtcgtaaca actccgcccc attgacgcaa | 900 |
| atgggcggta ggcgtgtacg gtgggaggtc tatataagca gagctcgttt agtgaaccgt | 960 |
| cagatcgcct ggagacgcca tccacgctgt tttgacctcc atagaagaca ccgggaccga | 1020 |
| tccagcctcc gcggccggga acggtgcatt ggaatcgatg actctcttag gtagccttgc | 1080 |
| agaagttggt cgtgaggcac tgggcaggta agtatcaagg ttacaagaca ggtttaagga | 1140 |
| gatcaataga aactgggctt gtcgagacag agaagactct tgcgtttctg ataggcacct | 1200 |
| attggtctta ctgacatcca ctttgccttt ctctccacag gtgtccactc ccagttcaat | 1260 |

```
tacagctcgc caccatggcc tgccccggct tcctgtgggc cctggtgatc agcacctgcc    1320
tcgagttcag cggccctaag cggaccgtgg ccgctcccag cgtgttcatc ttccccccct    1380
ccgacgagca gctgaagagc ggcaccgcca gcgtggtgtg cctgctgaac aacttctacc    1440
cccgggaggc caaggtgcag tggaaggtgg acaacgccct gcagagcggc aacagccagg    1500
agagcgtgac cgagcaggac agcaaggact ccacctacag cctgagcagc accctcaccc    1560
tgagcaaggc cgactacgag aagcacaagg tgtacgcctg cgaggtgacc caccagggcc    1620
tgagcagccc cgtgaccaag agcttcaacc ggggcgagtg ttaatagact taagtttaaa    1680
ccgctgatca gcctcgactg tgccttctag ttgccagcca tctgttgttt gcccctcccc    1740
cgtgccttcc ttgaccctgg aaggtgccac tcccactgtc ctttcctaat aaaatgagga    1800
aattgcatcg cattgtctga gtaggtgtca ttctattctg gggggtgggg tgggcagga    1860 cagcaagggg gaggattggg aagacaatag caggcatgct ggggatgcgg tgggctctat    1920
ggcttctgag gcggaaagaa ccagctgggg ctctagggga tatccccacg cgccctgtag    1980
cggcgcatta agcgcggcgg gtgtggtggt tacgcgcagc gtgaccgcta cacttgccag    2040
cgccctagcg cccgctcctt tcgctttctt cccttccttt ctcgccacgt tcgccggctt    2100
tccccgtcaa gctctaaatc gggggctccc tttagggttc cgatttagtg ctttacggca    2160
cctcgacccc aaaaaacttg attagggtga tggttcacgt agtgggccat cgccctgata    2220
gacggttttt cgcccttga cgttggagtc cacgttcttt aatagtggac tcttgttcca    2280
aactggaaca cactcaacc ctatctcggt ctattctttt gatttataag gattttggc    2340 catttcggcc tattggttaa aaatgagct gatttaacaa aatttaacg cgaattaatt    2400 ctgtggaatg tgtgtcagtt agggtgtgga aagtccccag gctccccagc aggcagaagt    2460
atgcaaagca tgcatctcaa ttagtcagca accaggtgtg gaaagtcccc aggctcccca    2520
gcaggcagaa gtatgcaaag catgcatctc aattagtcag caaccatagt cccgccccta    2580
actccgccca tcccgcccct aactccgccc agttccgccc attctccgcc ccatggctga    2640 ctaattttt ttatttatgc agaggccgag gccgcctctg cctctgagct attccagaag    2700
tagtgaggag gcttttttgg aggcctaggc ttttgcaaaa agctcccggg agcttgtata    2760 tccatttcg gatctgatca gcacgtgatg aaaaagcctg aactcaccgc gacgtctgtc    2820
gagaagtttc tgatcgaaaa gttcgacagc gtctccgacc tgatgcagct ctcggagggc    2880
gaagaatctc gtgctttcag cttcgatgta ggagggcgtg gatatgtcct gcgggtaaat    2940
agctgcgccg atggtttcta caaagatcgt tatgtttatc ggcactttgc atcggccgcg    3000
ctcccgattc cggaagtgct tgacattggg gaattcagcg agagcctgac ctattgcatc    3060
tcccgccgtg cacagggtgt cacgttgcaa gacctgcctg aaaccgaact gcccgctgtt    3120
ctgcagccgg tcgcggaggc catggatgcg atcgctgcgg ccgatcttag ccagacgagc    3180
gggttcggcc cattcggacc acaaggaatc ggtcaataca ctacatggcg tgatttcata    3240
tgcgcgattg ctgatcccca tgtgtatcac tggcaaactg tgatggacga caccgtcagt    3300
gcgtccgtcg cgcaggctct cgatgagctg atgctttggg ccgaggactg ccccgaagtc    3360
cggcacctcg tgcacgcgga tttcggctcc aacaatgtcc tgacggacaa tggccgcata    3420
acagcggtca ttgactggag cgaggcgatg ttcgggatt cccaatacga ggtcgccaac    3480
atcttcttct ggaggccgtg gttggcttgt atggagcagc agacgcgcta cttcgagcgg    3540
aggcatccgg agcttgcagg atcgccgcgg ctccgggcgt atatgctccg cattggtctt    3600
gaccaactct atcagagctt ggttgacggc aatttcgatg atgcagcttg ggcgcagggt    3660
```

```
cgatgcgacg caatcgtccg atccggagcc gggactgtcg ggcgtacaca aatcgcccgc    3720
agaagcgcgg ccgtctggac cgatggctgt gtagaagtac tcgccgatag tggaaaccga    3780
cgccccagca ctcgtccgag ggcaaaggaa tagcacgtgc tacgagattt cgattccacc    3840
gccgccttct atgaaaggtt gggcttcgga atcgttttcc gggacgccgg ctggatgatc    3900
ctccagcgcg gggatctcat gctggagttc ttcgcccacc ccaacttgtt tattgcagct    3960
tataatggtt acaaataaag caatagcatc acaaatttca caaataaagc attttttca    4020 ctgcattcta gttgtggttt gtccaaactc atcaatgtat cttatcatgt ctgtataccg    4080
tcgacctcta gctagagctt ggcgtaatca tggtcatagc tgtttcctgt gtgaaattgt    4140
tatccgctca caattccaca acatacga gccggaagca taaagtgtaa agcctgggt     4200 gcctaatgag tgagctaact cacattaatt gcgttgcgct cactgcccgc tttccagtcg    4260
ggaaacctgt cgtgccagct gcattaatga atcggccaac gcgcggggag aggcggtttg    4320
cgtattgggc gctcttccgc ttcctcgctc actgactcgc tgcgctcggt cgttcggctg    4380
cggcgagcgg tatcagctca ctcaaaggcg gtaatacggt tatccacaga atcaggggat    4440
aacgcaggaa agaacatgtg agcaaaaggc cagcaaaagg ccaggaaccg taaaaaggcc    4500
gcgttgctgg cgtttttcca taggctccgc cccctgacg agcatcacaa aaatcgacgc     4560
tcaagtcaga ggtggcgaaa cccgacagga ctataaagat accaggcgtt ccccctgga     4620 agctccctcg tgcgctctcc tgttccgacc ctgccgctta ccggatacct gtccgccttt    4680
ctcccttcgg gaagcgtggc gctttctcat agctcacgct gtaggtatct cagttcggtg    4740
taggtcgttc gctccaagct gggctgtgtg cacgaacccc ccgttcagcc cgaccgctgc    4800
gccttatccg gtaactatcg tcttgagtcc aacccggtaa gacacgactt atcgccactg    4860
gcagcagcca ctggtaacag gattagcaga gcgaggtatg taggcggtgc tacagagttc    4920
ttgaagtggt ggcctaacta cggctacact agaagaacag tatttggtat ctgcgctctg    4980
ctgaagccag ttaccttcgg aaaaagagtt ggtagctctt gatccggcaa acaaaccacc    5040
gctggtagcg gtttttttgt ttgcaagcag cagattacgc gcagaaaaaa aggatctcaa    5100
gaagatcctt tgatcttttc tacggggtct gacgctcagt ggaacgaaaa ctcacgttaa    5160
gggattttgg tcatgagatt atcaaaaagg atcttcacct agatcctttt aaattaaaaa    5220
tgaagtttta aatcaatcta agtatatat gagtaaactt ggtctgacag ttaccaatgc    5280
ttaatcagtg aggcacctat ctcagcgatc tgtctatttc gttcatccat agttgcctga    5340
ctccccgtcg tgtagataac tacgatacgg gagggcttac catctggccc cagtgctgca    5400
atgataccgc gagacccacg ctcaccggct ccagatttat cagcaataaa ccagccagcc    5460
ggaagggccg agcgcagaag tggtcctgca actttatccg cctccatcca gtctattaat    5520
tgttgccggg aagctagagt aagtagttcg ccagttaata gtttgcgcaa cgttgttgcc    5580
attgctacag gcatcgtggt gtcacgctcg tcgtttggta tggcttcatt cagctccggt    5640
tcccaacgat caaggcgagt tacatgatcc cccatgttgt gcaaaaaagc ggttagctcc    5700
ttcggtcctc cgatcgttgt cagaagtaag ttggccgcag tgttatcact catggttatg    5760
gcagcactgc ataattctct tactgtcatg ccatccgtaa gatgcttttc tgtgactggt    5820
gagtactcaa ccaagtcatt ctgagaatag tgtatgcggc gaccgagttg ctcttgcccg    5880
gcgtcaatac gggataatac cgcgccacat agcagaactt taaaagtgct catcattgga    5940
aaacgttctt cggggcgaaa actctcaagg atcttaccgc tgttgagatc cagttcgatg    6000
taacccactc gtgcacccaa ctgatcttca gcatctttta ctttcaccag cgtttctggg    6060
```

```
tgagcaaaaa caggaaggca aaatgccgca aaaagggaa taagggcgac acggaaatgt    6120
tgaatactca tactcttcct ttttcaatat tattgaagca tttatcaggg ttattgtctc    6180
atgagcggat acatatttga atgtatttag aaaaataaac aaataggggt tccgcgcaca    6240
tttccccgaa aagtgccacc tgacgtc                                        6267

<210> SEQ ID NO 39
<211> LENGTH: 6283
<212> TYPE: DNA
<213> ORGANISM: Artificial sequence
<220> FEATURE:
<223> OTHER INFORMATION: Chemically synthesized - pSyn-C04-Clambda

<400> SEQUENCE: 39
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgttaa ttaacatgaa    180
gaatctgctt agggttaggc gttttgcgct gcttcgctag gtggtcaata ttggccatta    240
gccatattat tcattggtta tatagcataa atcaatattg gctattggcc attgcatacg    300
ttgtatccat atcataatat gtacatttat attggctcat gtccaacatt accgccatgt    360
tgacattgat tattgactag ttattaatag taatcaatta cggggtcatt agttcatagc    420
ccatatatgg agttccgcgt tacataactt acggtaaatg gcccgcctgg ctgaccgccc    480
aacgaccccc gcccattgac gtcaataatg acgtatgttc ccatagtaac gccaataggg    540
actttccatt gacgtcaatg ggtggagtat ttacggtaaa ctgcccactt ggcagtacat    600
caagtgtatc atatgccaag tacgccccct attgacgtca atgacggtaa atggcccgcc    660
tggcattatg cccagtacat gaccttatgg gactttccta cttggcagta catctacgta    720
ttagtcatcg ctattaccat ggtgatgcgg ttttggcagt acatcaatgg gcgtggatag    780
cggtttgact cacggggatt tccaagtctc cacccattg acgtcaatgg gagtttgttt    840
tggcaccaaa atcaacggga ctttccaaaa tgtcgtaaca actccgcccc attgacgcaa    900
atgggcggta ggcgtgtacg gtgggaggtc tatataagca gagctcgttt agtgaaccgt    960
cagatcgcct ggagacgcca tccacgctgt tttgacctcc atagaagaca ccgggaccga   1020
tccagcctcc gcggccggga acggtgcatt ggaatcgatg actctcttag gtagccttgc   1080
agaagttggt cgtgaggcac tgggcaggta agtatcaagg ttacaagaca ggtttaagga   1140
gatcaataga aactgggctt gtcgagacag agaagactct tgcgtttctg ataggcacct   1200
attggtctta ctgacatcca ctttgccttt ctctccacag gtgtccactc ccagttcaat   1260
tacagctcgc caccatggcc tgccccggct tcctgtgggc cctggtgatc agcacctgcc   1320
tcgagatccc cggaccgcgg ccgcaagctt accgtgctgg ccagcccaa ggccgctccc    1380 agcgtgaccc tgttccccc ctcctccgag gagctgcagg ccaacaaggc caccctggtg   1440
tgcctcatca gcgacttcta ccctggcgcc gtgaccgtgg cctggaaggc cgacagcagc   1500
cccgtgaagg ccggcgtgga gaccaccacc cccagcaagc agagcaacaa caagtacgcc   1560
gccagcagct acctgagcct cacccccgag cagtggaaga gccaccggag ctacagctgc   1620
caggtgaccc acgagggcag caccgtggag aagaccgtgg ccccaccga gtgcagctaa   1680 tagacttaag tttaaaccgc tgatcagcct cgactgtgcc ttctagttgc cagccatctg   1740
ttgtttgccc ctcccccgtg ccttccttga ccctggaagg tgccactccc actgtccttt   1800
cctaataaaa tgaggaaatt gcatcgcatt gtctgagtag gtgtcattct attctggggg   1860
```

```
gtggggtggg gcaggacagc aaggggagg attgggaaga caatagcagg catgctgggg      1920
atgcggtggg ctctatggct tctgaggcgg aaagaaccag ctggggctct aggggtatc      1980 cccacgcgcc ctgtagcggc gcattaagcg cggcgggtgt ggtggttacg cgcagcgtga      2040
ccgctacact tgccagcgcc ctagcgcccg ctcctttcgc tttcttccct tcctttctcg      2100
ccacgttcgc cggctttccc cgtcaagctc taaatcgggg gctccctttt ggggttccgat     2160 ttagtgcttt acggcacctc gaccccaaaa aacttgatta gggtgatggt tcacgtagtg      2220
ggccatcgcc ctgatagacg gttttttcgcc ctttgacgtt ggagtccacg ttctttaata    2280
gtggactctt gttccaaact ggaacaacac tcaaccctat ctcggtctat tcttttgatt     2340
tataagggat tttggccatt tcggcctatt ggttaaaaaa tgagctgatt taacaaaaat    2400
ttaacgcgaa ttaattctgt ggaatgtgtg tcagttaggg tgtggaaagt ccccaggctc     2460
cccagcaggc agaagtatgc aaagcatgca tctcaattag tcagcaacca ggtgtggaaa     2520
gtccccaggc tccccagcag gcagaagtat gcaaagcatg catctcaatt agtcagcaac     2580
catagtcccg cccctaactc cgcccatccc gcccctaact ccgcccagtt ccgcccattc     2640
tccgccccat ggctgactaa ttttttttat ttatgcagag gccgaggccg cctctgcctc     2700
tgagctattc cagaagtagt gaggaggctt ttttggaggc ctaggctttt gcaaaaagct    2760
cccgggagct tgtatatcca ttttcggatc tgatcagcac gtgatgaaaa agcctgaact    2820
caccgcgacg tctgtcgaga agtttctgat cgaaaagttc gacagcgtct ccgacctgat    2880
gcagctctcg gagggcgaag aatctcgtgc tttcagcttc gatgtaggag ggcgtggata    2940
tgtcctgcgg gtaaatagct gcgccgatgg tttctacaaa gatcgttatg tttatcggca    3000
ctttgcatcg gccgcgctcc cgattccgga agtgcttgac attggggaat tcagcgagag    3060
cctgacctat tgcatctccc gccgtgcaca gggtgtcacg ttgcaagacc tgcctgaaac    3120
cgaactgccc gctgttctgc agccggtcgc ggaggccatg gatgcgatcg ctgcggccga    3180
tcttagccag acgagcgggt tcggcccatt cggaccgcaa ggaatcggtc aatacactac    3240
atggcgtgat ttcatatgcg cgattgctga tccccatgtg tatcactggc aaactgtgat    3300
ggacgacacc gtcagtgcgt ccgtcgcgca ggctctcgat gagctgatgc tttgggccga    3360
ggactgcccc gaagtccggc acctcgtgca cgcggatttc ggctccaaca atgtcctgac    3420
ggacaatggc cgcataacag cggtcattga ctggagcgag gcgatgttcg gggattccca    3480
atacgaggtc gccaacatct tcttctggag gccgtggttg gcttgtatgg agcagcagac    3540
gcgctacttc gagcggaggc atccggagct tgcaggatcg ccgcggctcc gggcgtatat    3600
gctccgcatt ggtcttgacc aactctatca gagcttggtt gacggcaatt tcgatgatgc    3660
agcttgggcg cagggtcgat gcgacgcaat cgtccgatcc ggagccggga ctgtcgggcg    3720
tacacaaatc gcccgcagaa gcgcggccgt ctggaccgat ggctgtgtag aagtactcgc    3780
cgatagtgga aaccgacgcc ccagcactcg tccgagggca aaggaatagc acgtgctacg    3840
agatttcgat tccaccgccg ccttctatga aaggttgggc ttcggaatcg ttttccggga    3900
cgccggctgg atgatcctcc agcgcgggga tctcatgctg gagttcttcg cccaccccaa    3960
cttgtttatt gcagcttata atggttacaa ataaagcaat agcatcacaa atttcacaaa    4020
taaagcattt ttttcactgc attctagttg tggtttgtcc aaactcatca atgtatctta    4080
tcatgtctgt ataccgtcga cctctagcta gagcttggcg taatcatggt catagctgtt    4140
tcctgtgtga aattgttatc cgctcacaat tccacacaac atacgagccg gaagcataaa    4200
gtgtaaagcc tggggtgcct aatgagtgag ctaactcaca ttaattgcgt tgcgctcact    4260
```

```
gcccgctttc cagtcgggaa acctgtcgtg ccagctgcat taatgaatcg gccaacgcgc    4320
ggggagaggc ggtttgcgta ttgggcgctc ttccgcttcc tcgctcactg actcgctgcg    4380
ctcggtcgtt cggctgcggc gagcggtatc agctcactca aaggcggtaa tacggttatc    4440
cacagaatca ggggataacg caggaaagaa catgtgagca aaaggccagc aaaaggccag    4500
gaaccgtaaa aaggccgcgt tgctggcgtt tttccatagg ctccgccccc ctgacgagca    4560
tcacaaaaat cgacgctcaa gtcagaggtg gcgaaacccg acaggactat aaagatacca    4620
ggcgtttccc cctggaagct ccctcgtgcg ctctcctgtt ccgaccctgc cgcttaccgg    4680
atacctgtcc gcctttctcc cttcgggaag cgtggcgctt tctcatagct cacgctgtag    4740
gtatctcagt tcggtgtagg tcgttcgctc caagctgggc tgtgtgcacg aaccccccgt    4800
tcagcccgac cgctgcgcct tatccggtaa ctatcgtctt gagtccaacc cggtaagaca    4860
cgacttatcg ccactggcag cagccactgg taacaggatt agcagagcga ggtatgtagg    4920
cggtgctaca gagttcttga agtggtggcc taactacggc tacactagaa gaacagtatt    4980
tggtatctgc gctctgctga agccagttac cttcggaaaa agagttggta gctcttgatc    5040
cggcaaacaa accaccgctg gtagcggttt ttttgtttgc aagcagcaga ttacgcgcag    5100
aaaaaaagga tctcaagaag atcctttgat cttttctacg gggtctgacg ctcagtggaa    5160
cgaaaactca cgttaaggga ttttggtcat gagattatca aaaaggatct tcacctagat    5220
ccttttaaat taaaaatgaa gttttaaatc aatctaaagt atatatgagt aaacttggtc    5280
tgacagttac caatgcttaa tcagtgaggc acctatctca gcgatctgtc tatttcgttc    5340
atccatagtt gcctgactcc ccgtcgtgta gataactacg atacgggagg gcttaccatc    5400
tggccccagt gctgcaatga taccgcgaga cccacgctca ccggctccag atttatcagc    5460
aataaaccag ccagccggaa gggccgagcg cagaagtggt cctgcaactt tatccgcctc    5520
catccagtct attaattgtt gccgggaagc tagagtaagt agttcgccag ttaatagttt    5580
gcgcaacgtt gttgccattg ctacaggcat cgtggtgtca cgctcgtcgt ttggtatggc    5640
ttcattcagc tccggttccc aacgatcaag gcgagttaca tgatccccca tgttgtgcaa    5700
aaaagcggtt agctccttcg gtcctccgat cgttgtcaga agtaagttgg ccgcagtgtt    5760
atcactcatg gttatggcag cactgcataa ttctcttact gtcatgccat ccgtaagatg    5820
cttttctgtg actggtgagt actcaaccaa gtcattctga gaatagtgta tgcggcgacc    5880
gagttgctct tgcccggcgt caatacggga taataccgcg ccacatagca gaactttaaa    5940
agtgctcatc attggaaaac gttcttcggg gcgaaaactc tcaaggatct taccgctgtt    6000
gagatccagt tcgatgtaac ccactcgtgc acccaactga tcttcagcat cttttacttt    6060
caccagcgtt tctgggtgag caaaaacagg aaggcaaaat gccgcaaaaa agggaataag    6120
ggcgacacgg aaatgttgaa tactcatact cttcctttt caatattatt gaagcattta    6180
tcagggttat tgtctcatga gcggatacat atttgaatgt atttagaaaa ataaacaaat    6240 agggggttccg cgcacatttc cccgaaaagt gccacctgac gtc                    6283
```

<210> SEQ ID NO 40
<211> LENGTH: 54
<212> TYPE: DNA
<213> ORGANISM: Artificial sequence
<220> FEATURE:
<223> OTHER INFORMATION: Chemically synthesized - Oligonucleotide 5k-I

<400> SEQUENCE: 40

```
acctgtctcg agttttccat ggctgacatc cagatgaccc agtctccatc ctcc          54
```

<210> SEQ ID NO 41
<211> LENGTH: 42
<212> TYPE: DNA
<213> ORGANISM: Artificial sequence
<220> FEATURE:
<223> OTHER INFORMATION: Chemically synthesized - Oligonucleotide
      sy3K-C

<400> SEQUENCE: 41
gggaccaagg tggagatcaa acggaccgtg ccgcccccca gc                         42

<210> SEQ ID NO 42
<211> LENGTH: 52
<212> TYPE: DNA
<213> ORGANISM: Artificial sequence
<220> FEATURE:
<223> OTHER INFORMATION: Chemically synthesized - Oligonucleotide
      sy5L-A

<400> SEQUENCE: 42
acctgtctcg agttttccat ggcttcctcc gagctgaccc aggaccctgc tg              52

<210> SEQ ID NO 43
<211> LENGTH: 44
<212> TYPE: DNA
<213> ORGANISM: Artificial sequence
<220> FEATURE:
<223> OTHER INFORMATION: Chemically synthesized - Oligonucleotide 3L-B

<400> SEQUENCE: 43
ttttccttag cggccgcgac tcacctagga cggtcagctt ggtc                       44

<210> SEQ ID NO 44
<211> LENGTH: 49
<212> TYPE: DNA
<213> ORGANISM: Artificial sequence
<220> FEATURE:
<223> OTHER INFORMATION: Chemically synthesized - Oligonucleotide
      5H-Fshort

<400> SEQUENCE: 44
acctgtcttg aattctccat ggcccaggtg cagctgcagg agtccggcc                  49

<210> SEQ ID NO 45
<211> LENGTH: 47
<212> TYPE: DNA
<213> ORGANISM: Artificial sequence
<220> FEATURE:
<223> OTHER INFORMATION: Chemically synthesized - Oligonucleotide
      sy3H-A

<400> SEQUENCE: 45
gcccttggtg ctagcgctgg agacggtcac cagggtgccc tggcccc                    47

<210> SEQ ID NO 46
<211> LENGTH: 46
<212> TYPE: DNA
<213> ORGANISM: Artificial sequence
<220> FEATURE:
<223> OTHER INFORMATION: Chemically synthesized - Oligonucleotide 5H-B

<400> SEQUENCE: 46
acctgtcttg aattctccat ggccgaggtg cagctggtgg agtctg                     46

<210> SEQ ID NO 47
<211> LENGTH: 65

```
<212> TYPE: DNA
<213> ORGANISM: Artificial sequence
<220> FEATURE:
<223> OTHER INFORMATION: Chemically synthesized - Oligonucleotide
      5H-B**65

<400> SEQUENCE: 47
acctgtcttg aattctccat ggccgaggtg cagctggtgg agtctggggg aggcttggta      60
catcc                                                                  65

<210> SEQ ID NO 48
<211> LENGTH: 47
<212> TYPE: DNA
<213> ORGANISM: Artificial sequence
<220> FEATURE:
<223> OTHER INFORMATION: Chemically synthesized - Oligonucleotide 5H-A

<400> SEQUENCE: 48
acctgtcttg aattctccat ggcccaggtg cagctggtgc agtctgg                    47

<210> SEQ ID NO 49
<211> LENGTH: 68
<212> TYPE: DNA
<213> ORGANISM: Artificial sequence
<220> FEATURE:
<223> OTHER INFORMATION: Chemically synthesized - Oligonucleotide
      115int68

<400> SEQUENCE: 49
caccagggtg ccctggcccc agtagtcaaa gtaactcggc atctgcgacc ttgcacagta      60
atacacgg                                                               68

<210> SEQ ID NO 50
<211> LENGTH: 1341
<212> TYPE: DNA
<213> ORGANISM: Artificial sequence
<220> FEATURE:
<223> OTHER INFORMATION: Chemically synthesized - Heavy chain of
      O2-113
<220> FEATURE:
<221> NAME/KEY: CDS
<222> LOCATION: (1)..(1341)

<400> SEQUENCE: 50 cag gtg cag ctg cag gag tcc ggc gca gga ctg ttg aag cct tcg gag         48
Gln Val Gln Leu Gln Glu Ser Gly Ala Gly Leu Leu Lys Pro Ser Glu
1               5                   10                  15 acc ctg tcc ctc acc tgc gct gtc tat ggt ggg tct ttc agt ggc tac         96
Thr Leu Ser Leu Thr Cys Ala Val Tyr Gly Gly Ser Phe Ser Gly Tyr
            20                  25                  30 tac tgg agc tgg atc cgg cag ccc cca ggg aag gga ctg gag tgg att        144
Tyr Trp Ser Trp Ile Arg Gln Pro Pro Gly Lys Gly Leu Glu Trp Ile
        35                  40                  45 ggg tat atc tat tac agt ggg agc acc aac tac aac ccc tcc ctc aag        192
Gly Tyr Ile Tyr Tyr Ser Gly Ser Thr Asn Tyr Asn Pro Ser Leu Lys
    50                  55                  60 agt cga gtc acc ata tca gta gac acg tcc aag aac cag ttc tcc ctg        240
Ser Arg Val Thr Ile Ser Val Asp Thr Ser Lys Asn Gln Phe Ser Leu
65                  70                  75                  80 aag ctg agc tct gtg acc gct gcg gac acg gcc gtg tat tac tgt gca        288
Lys Leu Ser Ser Val Thr Ala Ala Asp Thr Ala Val Tyr Tyr Cys Ala
                85                  90                  95 aag gcc cct tat atg atg tat ttt gac tcc tgg ggc cag ggc acc ctg        336
Lys Ala Pro Tyr Met Met Tyr Phe Asp Ser Trp Gly Gln Gly Thr Leu
            100                 105                 110
```

```
gtg acc gtc tcc agc gct agc acc aag ggc ccc agc gtg ttc ccc ctg       384
Val Thr Val Ser Ser Ala Ser Thr Lys Gly Pro Ser Val Phe Pro Leu
        115                 120                 125 gcc ccc agc agc aag agc acc agc ggc ggc aca gcc gcc ctg ggc tgc       432
Ala Pro Ser Ser Lys Ser Thr Ser Gly Gly Thr Ala Ala Leu Gly Cys
130                 135                 140 ctg gtg aag gac tac ttc ccc gag ccc gtg acc gtg agc tgg aac agc       480
Leu Val Lys Asp Tyr Phe Pro Glu Pro Val Thr Val Ser Trp Asn Ser
145                 150                 155                 160 ggc gcc ttg acc agc ggc gtg cac acc ttc ccc gcc gtg ctg cag agc       528
Gly Ala Leu Thr Ser Gly Val His Thr Phe Pro Ala Val Leu Gln Ser
                165                 170                 175 agc ggc ctg tac agc ctg agc agc gtg gtg acc gtg ccc agc agc agc       576
Ser Gly Leu Tyr Ser Leu Ser Ser Val Val Thr Val Pro Ser Ser Ser
                180                 185                 190 ctg ggc acc cag acc tac atc tgc aac gtg aac cac aag ccc agc aac       624
Leu Gly Thr Gln Thr Tyr Ile Cys Asn Val Asn His Lys Pro Ser Asn
                195                 200                 205 acc aag gtg gac aaa cgc gtg gag ccc aag agc tgc gac aag acc cac       672
Thr Lys Val Asp Lys Arg Val Glu Pro Lys Ser Cys Asp Lys Thr His
210                 215                 220 acc tgc ccc ccc tgc cct gcc ccc gag ctg ctg ggc gga ccc tcc gtg       720
Thr Cys Pro Pro Cys Pro Ala Pro Glu Leu Leu Gly Gly Pro Ser Val
225                 230                 235                 240 ttc ctg ttc ccc ccc aag ccc aag gac acc ctc atg atc agc cgg acc       768
Phe Leu Phe Pro Pro Lys Pro Lys Asp Thr Leu Met Ile Ser Arg Thr
                245                 250                 255 ccc gag gtg acc tgc gtg gtg gtg gac gtg agc cac gag gac ccc gag       816
Pro Glu Val Thr Cys Val Val Val Asp Val Ser His Glu Asp Pro Glu
                260                 265                 270 gtg aag ttc aac tgg tac gtg gac ggc gtg gag gtg cac aac gcc aag       864
Val Lys Phe Asn Trp Tyr Val Asp Gly Val Glu Val His Asn Ala Lys
                275                 280                 285 acc aag ccc cgg gag gag cag tac aac agc acc tac cgg gtg gtg agc       912
Thr Lys Pro Arg Glu Glu Gln Tyr Asn Ser Thr Tyr Arg Val Val Ser
290                 295                 300 gtg ctc acc gtg ctg cac cag gac tgg ctg aac ggc aag gag tac aag       960
Val Leu Thr Val Leu His Gln Asp Trp Leu Asn Gly Lys Glu Tyr Lys
305                 310                 315                 320 tgc aag gtg agc aac aag gcc ctg cct gcc ccc atc gag aag acc atc      1008
Cys Lys Val Ser Asn Lys Ala Leu Pro Ala Pro Ile Glu Lys Thr Ile
                325                 330                 335 agc aag gcc aag ggc cag ccc cgg gag ccc cag gtg tac acc ctg ccc      1056
Ser Lys Ala Lys Gly Gln Pro Arg Glu Pro Gln Val Tyr Thr Leu Pro
                340                 345                 350 ccc agc cgg gag gag atg acc aag aac cag gtg tcc ctc acc tgt ctg      1104
Pro Ser Arg Glu Glu Met Thr Lys Asn Gln Val Ser Leu Thr Cys Leu
                355                 360                 365 gtg aag ggc ttc tac ccc agc gac atc gcc gtg gag tgg gag agc aac      1152
Val Lys Gly Phe Tyr Pro Ser Asp Ile Ala Val Glu Trp Glu Ser Asn
370                 375                 380 ggc cag ccc gag aac aac tac aag acc acc ccc cct gtg ctg gac agc      1200
Gly Gln Pro Glu Asn Asn Tyr Lys Thr Thr Pro Pro Val Leu Asp Ser
385                 390                 395                 400 gac ggc agc ttc ttc ctg tac agc aag ctc acc gtg gac aag agc cgg      1248
Asp Gly Ser Phe Phe Leu Tyr Ser Lys Leu Thr Val Asp Lys Ser Arg
                405                 410                 415 tgg cag cag ggc aac gtg ttc agc tgc agc gtg atg cac gag gcc ctg      1296
Trp Gln Gln Gly Asn Val Phe Ser Cys Ser Val Met His Glu Ala Leu
                420                 425                 430
```

-continued

```
cac aac cac tac acc cag aag agc ctg agc ctg agc ccc ggc aag          1341
His Asn His Tyr Thr Gln Lys Ser Leu Ser Leu Ser Pro Gly Lys
            435                 440                 445
```

<210> SEQ ID NO 51
<211> LENGTH: 447
<212> TYPE: PRT
<213> ORGANISM: Artificial sequence
<220> FEATURE:
<223> OTHER INFORMATION: Chemically synthesized - Heavy chain of
      O2-113

<400> SEQUENCE: 51

```
Gln Val Gln Leu Gln Glu Ser Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Ala Pro Tyr Met Met Tyr Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
```

-continued

```
                    340                 345                 350
Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445
```

<210> SEQ ID NO 52
<211> LENGTH: 1344
<212> TYPE: DNA
<213> ORGANISM: Artificial sequence
<220> FEATURE:
<223> OTHER INFORMATION: Chemically synthesized - Heavy chain of 02-114
<220> FEATURE:
<221> NAME/KEY: CDS
<222> LOCATION: (1)..(1344)

<400> SEQUENCE: 52

```
gag gtg cag ctg gtg gag tct ggg gga ggc ttg gta cag cct ggg ggg     48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttc agt agc tat     96
Ser Leu Arg Leu Ser Cys Ala Ala Ser Gly Phe Thr Phe Ser Ser Tyr
            20                  25                  30 agc atg aac tgg gtc cgc cag gct cca ggg aag ggg ctg gag tgg gtt    144
Ser Met Asn Trp Val Arg Gln Ala Pro Gly Lys Gly Leu Glu Trp Val
        35                  40                  45 tca tac att agt agt agt agt agt acc ata tac tac gca gac tct gtg    192
Ser Tyr Ile Ser Ser Ser Ser Ser Thr Ile Tyr Tyr Ala Asp Ser Val
    50                  55                  60 aag ggc cga ttc acc atc tcc aga gac aat gcc aag aac tca ctg tat    240
Lys Gly Arg Phe Thr Ile Ser Arg Asp Asn Ala Lys Asn Ser Leu Tyr
65                  70                  75                  80 ctg caa atg aac agc ctg aga gac gag gac acg gcc gtg tat tac tgt    288
Leu Gln Met Asn Ser Leu Arg Asp Glu Asp Thr Ala Val Tyr Tyr Cys
                85                  90                  95 gca aag gag act tgg tgg cag tcc ttt gac tac tgg ggc cag ggc acc    336
Ala Lys Glu Thr Trp Trp Gln Ser Phe Asp Tyr Trp Gly Gln Gly Thr
            100                 105                 110 ctg gtg acc gtc tcc agc gct agc acc aag ggc ccc agc gtg ttc ccc    384
Leu Val Thr Val Ser Ser Ala Ser Thr Lys Gly Pro Ser Val Phe Pro
        115                 120                 125 ctg gcc ccc agc agc aag agc acc agc ggc ggc aca gcc gcc ctg ggc    432
Leu Ala Pro Ser Ser Lys Ser Thr Ser Gly Gly Thr Ala Ala Leu Gly
    130                 135                 140 tgc ctg gtg aag gac tac ttc ccc gag ccc gtg acc gtg agc tgg aac    480
Cys Leu Val Lys Asp Tyr Phe Pro Glu Pro Val Thr Val Ser Trp Asn
145                 150                 155                 160 agc ggc gcc ttg acc agc ggc gtg cac acc ttc ccc gcc gtg ctg cag    528
Ser Gly Ala Leu Thr Ser Gly Val His Thr Phe Pro Ala Val Leu Gln
                165                 170                 175 agc agc ggc ctg tac agc ctg agc agc gtg gtg acc gtg ccc agc agc    576
Ser Ser Gly Leu Tyr Ser Leu Ser Ser Val Val Thr Val Pro Ser Ser
```

```
agc ctg ggc acc cag acc tac atc tgc aac gtg aac cac aag ccc agc      624
Ser Leu Gly Thr Gln Thr Tyr Ile Cys Asn Val Asn His Lys Pro Ser
        195                 200                 205 aac acc aag gtg gac aaa cgc gtg gag ccc aag agc tgc gac aag acc      672
Asn Thr Lys Val Asp Lys Arg Val Glu Pro Lys Ser Cys Asp Lys Thr
    210                 215                 220 cac acc tgc ccc ccc tgc cct gcc ccc gag ctg ctg ggc gga ccc tcc      720
His Thr Cys Pro Pro Cys Pro Ala Pro Glu Leu Leu Gly Gly Pro Ser
225                 230                 235                 240 gtg ttc ctg ttc ccc ccc aag ccc aag gac acc ctc atg atc agc cgg      768
Val Phe Leu Phe Pro Pro Lys Pro Lys Asp Thr Leu Met Ile Ser Arg
                245                 250                 255 acc ccc gag gtg acc tgc gtg gtg gtg gac gtg agc cac gag gac ccc      816
Thr Pro Glu Val Thr Cys Val Val Val Asp Val Ser His Glu Asp Pro
            260                 265                 270 gag gtg aag ttc aac tgg tac gtg gac ggc gtg gag gtg cac aac gcc      864
Glu Val Lys Phe Asn Trp Tyr Val Asp Gly Val Glu Val His Asn Ala
        275                 280                 285 aag acc aag ccc cgg gag gag cag tac aac agc acc tac cgg gtg gtg      912
Lys Thr Lys Pro Arg Glu Glu Gln Tyr Asn Ser Thr Tyr Arg Val Val
    290                 295                 300 agc gtg ctc acc gtg ctg cac cag gac tgg ctg aac ggc aag gag tac      960
Ser Val Leu Thr Val Leu His Gln Asp Trp Leu Asn Gly Lys Glu Tyr
305                 310                 315                 320 aag tgc aag gtg agc aac aag gcc ctg cct gcc ccc atc gag aag acc     1008
Lys Cys Lys Val Ser Asn Lys Ala Leu Pro Ala Pro Ile Glu Lys Thr
                325                 330                 335 atc agc aag gcc aag ggc cag ccc cgg gag ccc cag gtg tac acc ctg     1056
Ile Ser Lys Ala Lys Gly Gln Pro Arg Glu Pro Gln Val Tyr Thr Leu
            340                 345                 350 ccc ccc agc cgg gag gag atg acc aag aac cag gtg tcc ctc acc tgt     1104
Pro Pro Ser Arg Glu Glu Met Thr Lys Asn Gln Val Ser Leu Thr Cys
        355                 360                 365 ctg gtg aag ggc ttc tac ccc agc gac atc gcc gtg gag tgg gag agc     1152
Leu Val Lys Gly Phe Tyr Pro Ser Asp Ile Ala Val Glu Trp Glu Ser
    370                 375                 380 aac ggc cag ccc gag aac aac tac aag acc acc ccc cct gtg ctg gac     1200
Asn Gly Gln Pro Glu Asn Asn Tyr Lys Thr Thr Pro Pro Val Leu Asp
385                 390                 395                 400 agc gac ggc agc ttc ttc ctg tac agc aag ctc acc gtg gac aag agc     1248
Ser Asp Gly Ser Phe Phe Leu Tyr Ser Lys Leu Thr Val Asp Lys Ser
                405                 410                 415 cgg tgg cag cag ggc aac gtg ttc agc tgc agc gtg atg cac gag gcc     1296
Arg Trp Gln Gln Gly Asn Val Phe Ser Cys Ser Val Met His Glu Ala
            420                 425                 430 ctg cac aac cac tac acc cag aag agc ctg agc ctg agc ccc ggc aag     1344
Leu His Asn His Tyr Thr Gln Lys Ser Leu Ser Leu Ser Pro Gly Lys
        435                 440                 445
```

<210> SEQ ID NO 53
<211> LENGTH: 448
<212> TYPE: PRT
<213> ORGANISM: Artificial sequence
<220> FEATURE:
<223> OTHER INFORMATION: Chemically synthesized - Heavy chain of
      02-114

<400> SEQUENCE: 53

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
        20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Lys Glu Thr Trp Trp Gln Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 54
<211> LENGTH: 1344
<212> TYPE: DNA
<213> ORGANISM: Artificial sequence
<220> FEATURE:
<223> OTHER INFORMATION: Chemically synthesized - Heavy chain of 02-115
<220> FEATURE:
<221> NAME/KEY: CDS
<222> LOCATION: (1)..(1344)

<400> SEQUENCE: 54

| | | | | | | | | | | | | | | | | |
|---|---|---|---|---|---|---|---|---|---|---|---|---|---|---|---|---|
| cag | gtg | cag | ctg | gtg | cag | tct | ggg | gct | gag | gcg | aag | aag | cct | ggg | gcc | 48 |
| Gln | Val | Gln | Leu | Val | Gln | Ser | Gly | Ala | Glu | Ala | Lys | Lys | Pro | Gly | Ala | |
| 1 | | | | 5 | | | | | 10 | | | | | 15 | | |
| tca | gtg | aag | gtc | tcc | tgc | aag | gct | tct | gga | tac | acc | ttc | acc | ggc | tac | 96 |
| Ser | Val | Lys | Val | Ser | Cys | Lys | Ala | Ser | Gly | Tyr | Thr | Phe | Thr | Gly | Tyr | |
| | | | 20 | | | | | 25 | | | | | 30 | | | |
| tat | atg | cac | tgg | gtg | cga | cag | gcc | cct | gga | caa | ggg | ctt | gag | tgg | atg | 144 |
| Tyr | Met | His | Trp | Val | Arg | Gln | Ala | Pro | Gly | Gln | Gly | Leu | Glu | Trp | Met | |
| | | 35 | | | | | 40 | | | | | 45 | | | | |
| gga | tgg | atc | agc | gct | tac | aat | ggt | aac | aca | aac | tat | gca | cag | aag | ctc | 192 |
| Gly | Trp | Ile | Ser | Ala | Tyr | Asn | Gly | Asn | Thr | Asn | Tyr | Ala | Gln | Lys | Leu | |
| 50 | | | | | 55 | | | | | 60 | | | | | | |
| cag | ggc | aga | gtc | acc | atg | acc | aca | gac | aca | tcc | acg | agc | aca | gcc | tac | 240 |
| Gln | Gly | Arg | Val | Thr | Met | Thr | Thr | Asp | Thr | Ser | Thr | Ser | Thr | Ala | Tyr | |
| 65 | | | | 70 | | | | | 75 | | | | | 80 | | |
| atg | gag | ctg | agg | agc | ctg | aga | tct | gac | gac | acg | gcc | gtg | tat | tac | tgt | 288 |
| Met | Glu | Leu | Arg | Ser | Leu | Arg | Ser | Asp | Asp | Thr | Ala | Val | Tyr | Tyr | Cys | |
| | | | | 85 | | | | | 90 | | | | | 95 | | |
| gca | agg | tcg | cag | atg | ccg | agt | tac | ttt | gac | tac | tgg | ggc | cag | ggc | acc | 336 |
| Ala | Arg | Ser | Gln | Met | Pro | Ser | Tyr | Phe | Asp | Tyr | Trp | Gly | Gln | Gly | Thr | |
| | | | 100 | | | | | 105 | | | | | 110 | | | |
| ctg | gtg | acc | gtc | tcc | agc | gct | agc | acc | aag | ggc | ccc | agc | gtg | ttc | ccc | 384 |
| Leu | Val | Thr | Val | Ser | Ser | Ala | Ser | Thr | Lys | Gly | Pro | Ser | Val | Phe | Pro | |
| | | 115 | | | | | 120 | | | | | 125 | | | | |
| ctg | gcc | ccc | agc | agc | aag | agc | acc | agc | ggc | gga | aca | gcc | gcc | ctg | ggc | 432 |
| Leu | Ala | Pro | Ser | Ser | Lys | Ser | Thr | Ser | Gly | Gly | Thr | Ala | Ala | Leu | Gly | |
| | | 130 | | | | | 135 | | | | | 140 | | | | |
| tgc | ctg | gtg | aag | gac | tac | ttc | ccc | gag | ccc | gtg | acc | gtg | agc | tgg | aac | 480 |
| Cys | Leu | Val | Lys | Asp | Tyr | Phe | Pro | Glu | Pro | Val | Thr | Val | Ser | Trp | Asn | |
| 145 | | | | | 150 | | | | | 155 | | | | | 160 | |
| agc | ggc | gcc | ttg | acc | agc | ggc | gtg | cac | acc | ttc | ccc | gcc | gtg | ctg | cag | 528 |
| Ser | Gly | Ala | Leu | Thr | Ser | Gly | Val | His | Thr | Phe | Pro | Ala | Val | Leu | Gln | |
| | | | | 165 | | | | | 170 | | | | | 175 | | |
| agc | agc | ggc | ctg | tac | agc | ctg | agc | agc | gtg | gtg | acc | gtg | ccc | agc | agc | 576 |
| Ser | Ser | Gly | Leu | Tyr | Ser | Leu | Ser | Ser | Val | Val | Thr | Val | Pro | Ser | Ser | |
| | | | 180 | | | | | 185 | | | | | 190 | | | |
| agc | ctg | ggc | acc | cag | acc | tac | atc | tgc | aac | gtg | aac | cac | aag | ccc | agc | 624 |
| Ser | Leu | Gly | Thr | Gln | Thr | Tyr | Ile | Cys | Asn | Val | Asn | His | Lys | Pro | Ser | |
| | | 195 | | | | | 200 | | | | | 205 | | | | |
| aac | acc | aag | gtg | gac | aaa | cgc | gtg | gag | ccc | aag | agc | tgc | gac | aag | acc | 672 |
| Asn | Thr | Lys | Val | Asp | Lys | Arg | Val | Glu | Pro | Lys | Ser | Cys | Asp | Lys | Thr | |
| | 210 | | | | | 215 | | | | | 220 | | | | | |
| cac | acc | tgc | ccc | ccc | tgc | cct | gcc | ccc | gag | ctg | ctg | ggc | gga | ccc | tcc | 720 |
| His | Thr | Cys | Pro | Pro | Cys | Pro | Ala | Pro | Glu | Leu | Leu | Gly | Gly | Pro | Ser | |
| 225 | | | | | 230 | | | | | 235 | | | | | 240 | |
| gtg | ttc | ctg | ttc | ccc | ccc | aag | ccc | aag | gac | acc | ctc | atg | atc | agc | cgg | 768 |
| Val | Phe | Leu | Phe | Pro | Pro | Lys | Pro | Lys | Asp | Thr | Leu | Met | Ile | Ser | Arg | |
| | | | | 245 | | | | | 250 | | | | | 255 | | |
| acc | ccc | gag | gtg | acc | tgc | gtg | gtg | gtg | gac | gtg | agc | cac | gag | gac | ccc | 816 |

```
                Thr Pro Glu Val Thr Cys Val Val Asp Val Ser His Glu Asp Pro
                        260                 265                 270 gag gtg aag ttc aac tgg tac gtg gac ggc gtg gag gtg cac aac gcc         864
Glu Val Lys Phe Asn Trp Tyr Val Asp Gly Val Glu Val His Asn Ala
            275                 280                 285 aag acc aag ccc cgg gag gag cag tac aac agc acc tac cgg gtg gtg         912
Lys Thr Lys Pro Arg Glu Glu Gln Tyr Asn Ser Thr Tyr Arg Val Val
        290                 295                 300 agc gtg ctc acc gtg ctg cac cag gac tgg ctg aac ggc aag gag tac         960
Ser Val Leu Thr Val Leu His Gln Asp Trp Leu Asn Gly Lys Glu Tyr
305                 310                 315                 320 aag tgc aag gtg agc aac aag gcc ctg cct gcc ccc atc gag aag acc        1008
Lys Cys Lys Val Ser Asn Lys Ala Leu Pro Ala Pro Ile Glu Lys Thr
                325                 330                 335 atc agc aag gcc aag ggc cag ccc cgg gag ccc cag gtg tac acc ctg        1056
Ile Ser Lys Ala Lys Gly Gln Pro Arg Glu Pro Gln Val Tyr Thr Leu
            340                 345                 350 ccc ccc agc cgg gag gag atg acc aag aac cag gtg tcc ctc acc tgt        1104
Pro Pro Ser Arg Glu Glu Met Thr Lys Asn Gln Val Ser Leu Thr Cys
        355                 360                 365 ctg gtg aag ggc ttc tac ccc agc gac atc gcc gtg gag tgg gag agc        1152
Leu Val Lys Gly Phe Tyr Pro Ser Asp Ile Ala Val Glu Trp Glu Ser
    370                 375                 380 aac ggc cag ccc gag aac aac tac aag acc acc ccc cct gtg ctg gac        1200
Asn Gly Gln Pro Glu Asn Asn Tyr Lys Thr Thr Pro Pro Val Leu Asp
385                 390                 395                 400 agc gac ggc agc ttc ttc ctg tac agc aag ctc acc gtg gac aag agc        1248
Ser Asp Gly Ser Phe Phe Leu Tyr Ser Lys Leu Thr Val Asp Lys Ser
                405                 410                 415 cgg tgg cag cag ggc aac gtg ttc agc tgc agc gtg atg cac gag gcc        1296
Arg Trp Gln Gln Gly Asn Val Phe Ser Cys Ser Val Met His Glu Ala
            420                 425                 430 ctg cac aac cac tac acc cag aag agc ctg agc ctg agc ccc ggc aag        1344
Leu His Asn His Tyr Thr Gln Lys Ser Leu Ser Leu Ser Pro Gly Lys
        435                 440                 445

<210> SEQ ID NO 55
<211> LENGTH: 448
<212> TYPE: PRT
<213> ORGANISM: Artificial sequence
<220> FEATURE:
<223> OTHER INFORMATION: Chemically synthesized - Heavy chain of
      02-115

<400> SEQUENCE: 55

Gln Val Gln Leu Val Gln Ser Gly Ala Glu Ala Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Gln Met Pro Ser Tyr Phe Asp Tyr Trp Gly Gln Gly Thr
            100                 105                 110

Leu Val Thr Val Ser Ser Ala Ser Thr Lys Gly Pro Ser Val Phe Pro
```

```
                    115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Arg Val Glu Pro Lys Ser Cys Asp Lys Thr
210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 56
<211> LENGTH: 1344
<212> TYPE: DNA
<213> ORGANISM: Artificial sequence
<220> FEATURE:
<223> OTHER INFORMATION: Chemically synthesized - Heavy chain of
      02-116
<220> FEATURE:
<221> NAME/KEY: CDS
<222> LOCATION: (1)..(1344)

<400> SEQUENCE: 56 gag gtg cag ctg gtg gag tct ggg gga ggc ttg gta cag cct ggg ggg    48
Glu Val Gln Leu Val Glu Ser Gly Gly Gly Leu Val Gln Pro Gly Gly
1               5                   10                  15
```

| | | |
|---|---|---|
| tcc ctg aga ctc tcc tgt gca gcc tct gga ttc acc ttt agc agc tat<br>Ser Leu Arg Leu Ser Cys Ala Ala Ser Gly Phe Thr Phe Ser Ser Tyr<br>        20                    25                    30 | | 96 |
| gcc atg agc tgg gtc cgc cag gct cca ggg aag ggg ctg gag tgg gtc<br>Ala Met Ser Trp Val Arg Gln Ala Pro Gly Lys Gly Leu Glu Trp Val<br>      35                    40                    45 | | 144 |
| tca gct att agt ggt agt ggt ggt agc aca tac tac gca gac tcc gtg<br>Ser Ala Ile Ser Gly Ser Gly Gly Ser Thr Tyr Tyr Ala Asp Ser Val<br>50                    55                    60 | | 192 |
| aag ggc cgg ttc acc atc tcc aga gac aat tcc aag aac acg ctg tat<br>Lys Gly Arg Phe Thr Ile Ser Arg Asp Asn Ser Lys Asn Thr Leu Tyr<br>65                    70                    75                    80 | | 240 |
| ctg caa atg aac agc cta aga gcc gag gac acg gcc gtg tat tac tgt<br>Leu Gln Met Asn Ser Leu Arg Ala Glu Asp Thr Ala Val Tyr Tyr Cys<br>                    85                    90                    95 | | 288 |
| gca aag gac gct ctt tgg ctg gct ttt gac tac tgg ggc cag ggc acc<br>Ala Lys Asp Ala Leu Trp Leu Ala Phe Asp Tyr Trp Gly Gln Gly Thr<br>                  100                  105 | | 336 |
| ctg gtg acc gtc tcc agc gct agc acc aag ggc ccc agc gtg ttc ccc<br>Leu Val Thr Val Ser Ser Ala Ser Thr Lys Gly Pro Ser Val Phe Pro<br>        115                    120                  125 | | 384 |
| ctg gcc ccc agc agc aag agc acc agc ggc ggc aca gcc gcc ctg ggc<br>Leu Ala Pro Ser Ser Lys Ser Thr Ser Gly Gly Thr Ala Ala Leu Gly<br>130                    135                    140 | | 432 |
| tgc ctg gtg aag gac tac ttc ccc gag ccc gtg acc gtg agc tgg aac<br>Cys Leu Val Lys Asp Tyr Phe Pro Glu Pro Val Thr Val Ser Trp Asn<br>145                    150                    155                    160 | | 480 |
| agc ggc gcc ttg acc agc ggc gtg cac acc ttc ccc gcc gtg ctg cag<br>Ser Gly Ala Leu Thr Ser Gly Val His Thr Phe Pro Ala Val Leu Gln<br>                  165                    170                    175 | | 528 |
| agc agc ggc ctg tac agc ctg agc agc gtg gtg acc gtg ccc agc agc<br>Ser Ser Gly Leu Tyr Ser Leu Ser Ser Val Val Thr Val Pro Ser Ser<br>                  180                    185                    190 | | 576 |
| agc ctg ggc acc cag acc tac atc tgc aac gtg aac cac aag ccc agc<br>Ser Leu Gly Thr Gln Thr Tyr Ile Cys Asn Val Asn His Lys Pro Ser<br>        195                    200                  205 | | 624 |
| aac acc aag gtg gac aaa cgc gtg gag ccc aag agc tgc gac aag acc<br>Asn Thr Lys Val Asp Lys Arg Val Glu Pro Lys Ser Cys Asp Lys Thr<br>210                    215                    220 | | 672 |
| cac acc tgc ccc ccc tgc cct gcc ccc gag ctg ctg ggc gga ccc tcc<br>His Thr Cys Pro Pro Cys Pro Ala Pro Glu Leu Leu Gly Gly Pro Ser<br>225                    230                    235                    240 | | 720 |
| gtg ttc ctg ttc ccc ccc aag ccc aag gac acc ctc atg atc agc cgg<br>Val Phe Leu Phe Pro Pro Lys Pro Lys Asp Thr Leu Met Ile Ser Arg<br>                  245                    250                    255 | | 768 |
| acc ccc gag gtg acc tgc gtg gtg gtg gac gtg agc cac gag gac ccc<br>Thr Pro Glu Val Thr Cys Val Val Val Asp Val Ser His Glu Asp Pro<br>                  260                    265                    270 | | 816 |
| gag gtg aag ttc aac tgg tac gtg gac ggc gtg gag gtg cac aac gcc<br>Glu Val Lys Phe Asn Trp Tyr Val Asp Gly Val Glu Val His Asn Ala<br>        275                    280                  285 | | 864 |
| aag acc aag ccc cgg gag gag cag tac aac agc acc tac cgg gtg gtg<br>Lys Thr Lys Pro Arg Glu Glu Gln Tyr Asn Ser Thr Tyr Arg Val Val<br>290                    295                    300 | | 912 |
| agc gtg ctc acc gtg ctg cac cag gac tgg ctg aac ggc aag gag tac<br>Ser Val Leu Thr Val Leu His Gln Asp Trp Leu Asn Gly Lys Glu Tyr<br>305                    310                    315                    320 | | 960 |
| aag tgc aag gtg agc aac aag gcc ctg cct gcc ccc atc gag aag acc<br>Lys Cys Lys Val Ser Asn Lys Ala Leu Pro Ala Pro Ile Glu Lys Thr<br>                  325                    330                    335 | | 1008 |

| | | | | | | | | | | | | | | | |
|---|---|---|---|---|---|---|---|---|---|---|---|---|---|---|---|
| atc | agc | aag | gcc | aag | ggc | cag | ccc | cgg | gag | ccc | cag | gtg | tac | acc | ctg | 1056 |
| Ile | Ser | Lys | Ala | Lys | Gly | Gln | Pro | Arg | Glu | Pro | Gln | Val | Tyr | Thr | Leu |
| | | | 340 | | | | | 345 | | | | | 350 | | |

| ccc | ccc | agc | cgg | gag | gag | atg | acc | aag | aac | cag | gtg | tcc | ctc | acc | tgt | 1104 |
| Pro | Pro | Ser | Arg | Glu | Glu | Met | Thr | Lys | Asn | Gln | Val | Ser | Leu | Thr | Cys |
| | | 355 | | | | | 360 | | | | | 365 | | | |

| ctg | gtg | aag | ggc | ttc | tac | ccc | agc | gac | atc | gcc | gtg | gag | tgg | gag | agc | 1152 |
| Leu | Val | Lys | Gly | Phe | Tyr | Pro | Ser | Asp | Ile | Ala | Val | Glu | Trp | Glu | Ser |
| 370 | | | | | 375 | | | | | 380 | | | | | |

| aac | ggc | cag | ccc | gag | aac | aac | tac | aag | acc | acc | ccc | cct | gtg | ctg | gac | 1200 |
| Asn | Gly | Gln | Pro | Glu | Asn | Asn | Tyr | Lys | Thr | Thr | Pro | Pro | Val | Leu | Asp |
| 385 | | | | | 390 | | | | | 395 | | | | | 400 |

| agc | gac | ggc | agc | ttc | ttc | ctg | tac | agc | aag | ctc | acc | gtg | gac | aag | agc | 1248 |
| Ser | Asp | Gly | Ser | Phe | Phe | Leu | Tyr | Ser | Lys | Leu | Thr | Val | Asp | Lys | Ser |
| | | | | 405 | | | | | 410 | | | | | 415 | |

| cgg | tgg | cag | cag | ggc | aac | gtg | ttc | agc | tgc | agc | gtg | atg | cac | gag | gcc | 1296 |
| Arg | Trp | Gln | Gln | Gly | Asn | Val | Phe | Ser | Cys | Ser | Val | Met | His | Glu | Ala |
| | | | 420 | | | | | 425 | | | | | 430 | | |

| ctg | cac | aac | cac | tac | acc | cag | aag | agc | ctg | agc | ctg | agc | ccc | ggc | aag | 1344 |
| Leu | His | Asn | His | Tyr | Thr | Gln | Lys | Ser | Leu | Ser | Leu | Ser | Pro | Gly | Lys |
| | | 435 | | | | | 440 | | | | | 445 | | | |

<210> SEQ ID NO 57
<211> LENGTH: 448
<212> TYPE: PRT
<213> ORGANISM: Artificial sequence
<220> FEATURE:
<223> OTHER INFORMATION: Chemically synthesized - Heavy chain of 02-116

<400> SEQUENCE: 57

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ala Leu Trp Leu Ala Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220
```

```
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 58
<211> LENGTH: 1341
<212> TYPE: DNA
<213> ORGANISM: Artificial sequence
<220> FEATURE:
<223> OTHER INFORMATION: Chemically synthesized - Heavy chain of
      02-117
<220> FEATURE:
<221> NAME/KEY: CDS
<222> LOCATION: (1)..(1341)

<400> SEQUENCE: 58 gag gtg cag ctg gtg gag tct ggg gga ggc ttg gta cat cct ggg ggg     48
Glu Val Gln Leu Val Glu Ser Gly Gly Gly Leu Val His Pro Gly Gly
1               5                   10                  15 tcc ctg aga ctc tcc tgt gca ggc tct gga ttc acc ttc agt agc tat     96
Ser Leu Arg Leu Ser Cys Ala Gly Ser Gly Phe Thr Phe Ser Ser Tyr
            20                  25                  30 gct atg cac tgg gtt cgc cag gct cca gga aaa ggt ctg gag tgg gta    144
Ala Met His Trp Val Arg Gln Ala Pro Gly Lys Gly Leu Glu Trp Val
        35                  40                  45 tca gct att ggt act ggt ggt ggc aca tac tat gca gac tcc gtg aag    192
Ser Ala Ile Gly Thr Gly Gly Gly Thr Tyr Tyr Ala Asp Ser Val Lys
    50                  55                  60 ggc cga ttc acc atc tcc aga gac aat gcc aag aac tcc ttg tat ctt    240
Gly Arg Phe Thr Ile Ser Arg Asp Asn Ala Lys Asn Ser Leu Tyr Leu
65                  70                  75                  80 caa atg aac agc ctg aga gcc gag gac acg gcc gtg tat tac tgt gca    288
Gln Met Asn Ser Leu Arg Ala Glu Asp Thr Ala Val Tyr Tyr Cys Ala
                85                  90                  95
```

-continued

| | | |
|---|---|---|
| agg tct acg cct tgg ttt tcc ttt gac tac tgg ggc cag ggc acc ctg<br>Arg Ser Thr Pro Trp Phe Ser Phe Asp Tyr Trp Gly Gln Gly Thr Leu<br>            100                 105                 110 | 336 | |
| gtg acc gtc tcc agc gct agc acc aag ggc ccc agc gtg ttc ccc ctg<br>Val Thr Val Ser Ser Ala Ser Thr Lys Gly Pro Ser Val Phe Pro Leu<br>        115                 120                 125 | 384 | |
| gcc ccc agc agc aag agc acc agc ggc ggc aca gcc gcc ctg ggc tgc<br>Ala Pro Ser Ser Lys Ser Thr Ser Gly Gly Thr Ala Ala Leu Gly Cys<br>130                 135                 140 | 432 | |
| ctg gtg aag gac tac ttc ccc gag ccc gtg acc gtg agc tgg aac agc<br>Leu Val Lys Asp Tyr Phe Pro Glu Pro Val Thr Val Ser Trp Asn Ser<br>145                 150                 155                 160 | 480 | |
| ggc gcc ttg acc agc ggc gtg cac acc ttc ccc gcc gtg ctg cag agc<br>Gly Ala Leu Thr Ser Gly Val His Thr Phe Pro Ala Val Leu Gln Ser<br>                165                 170                 175 | 528 | |
| agc ggc ctg tac agc ctg agc agc gtg gtg acc gtg ccc agc agc agc<br>Ser Gly Leu Tyr Ser Leu Ser Ser Val Val Thr Val Pro Ser Ser Ser<br>            180                 185                 190 | 576 | |
| ctg ggc acc cag acc tac atc tgc aac gtg aac cac aag ccc agc aac<br>Leu Gly Thr Gln Thr Tyr Ile Cys Asn Val Asn His Lys Pro Ser Asn<br>        195                 200                 205 | 624 | |
| acc aag gtg gac aaa cgc gtg gag ccc aag agc tgc gac aag acc cac<br>Thr Lys Val Asp Lys Arg Val Glu Pro Lys Ser Cys Asp Lys Thr His<br>210                 215                 220 | 672 | |
| acc tgc ccc ccc tgc cct gcc ccc gag ctg ctg ggc gga ccc tcc gtg<br>Thr Cys Pro Pro Cys Pro Ala Pro Glu Leu Leu Gly Gly Pro Ser Val<br>225                 230                 235                 240 | 720 | |
| ttc ctg ttc ccc ccc aag ccc aag gac acc ctc atg atc agc cgg acc<br>Phe Leu Phe Pro Pro Lys Pro Lys Asp Thr Leu Met Ile Ser Arg Thr<br>                245                 250                 255 | 768 | |
| ccc gag gtg acc tgc gtg gtg gtg gac gtg agc cac gag gac ccc gag<br>Pro Glu Val Thr Cys Val Val Val Asp Val Ser His Glu Asp Pro Glu<br>            260                 265                 270 | 816 | |
| gtg aag ttc aac tgg tac gtg gac ggc gtg gag gtg cac aac gcc aag<br>Val Lys Phe Asn Trp Tyr Val Asp Gly Val Glu Val His Asn Ala Lys<br>        275                 280                 285 | 864 | |
| acc aag ccc cgg gag gag cag tac aac agc acc tac cgg gtg gtg agc<br>Thr Lys Pro Arg Glu Glu Gln Tyr Asn Ser Thr Tyr Arg Val Val Ser<br>290                 295                 300 | 912 | |
| gtg ctc acc gtg ctg cac cag gac tgg ctg aac ggc aag gag tac aag<br>Val Leu Thr Val Leu His Gln Asp Trp Leu Asn Gly Lys Glu Tyr Lys<br>305                 310                 315                 320 | 960 | |
| tgc aag gtg agc aac aag gcc ctg cct gcc ccc atc gag aag acc atc<br>Cys Lys Val Ser Asn Lys Ala Leu Pro Ala Pro Ile Glu Lys Thr Ile<br>                325                 330                 335 | 1008 | |
| agc aag gcc aag ggc cag ccc cgg gag ccc cag gtg tac acc ctg ccc<br>Ser Lys Ala Lys Gly Gln Pro Arg Glu Pro Gln Val Tyr Thr Leu Pro<br>            340                 345                 350 | 1056 | |
| ccc agc cgg gag gag atg acc aag aac cag gtg tcc ctc acc tgt ctg<br>Pro Ser Arg Glu Glu Met Thr Lys Asn Gln Val Ser Leu Thr Cys Leu<br>        355                 360                 365 | 1104 | |
| gtg aag ggc ttc tac ccc agc gac atc gcc gtg gag tgg gag agc aac<br>Val Lys Gly Phe Tyr Pro Ser Asp Ile Ala Val Glu Trp Glu Ser Asn<br>370                 375                 380 | 1152 | |
| ggc cag ccc gag aac aac tac aag acc acc ccc cct gtg ctg gac agc<br>Gly Gln Pro Glu Asn Asn Tyr Lys Thr Thr Pro Pro Val Leu Asp Ser<br>385                 390                 395                 400 | 1200 | |
| gac ggc agc ttc ttc ctg tac agc aag ctc acc gtg gac aag agc cgg<br>Asp Gly Ser Phe Phe Leu Tyr Ser Lys Leu Thr Val Asp Lys Ser Arg<br>                405                 410                 415 | 1248 | |

```
tgg cag cag ggc aac gtg ttc agc tgc agc gtg atg cac gag gcc ctg      1296
Trp Gln Gln Gly Asn Val Phe Ser Cys Ser Val Met His Glu Ala Leu
            420                 425                 430 cac aac cac tac acc cag aag agc ctg agc ctg agc ccc ggc aag          1341
His Asn His Tyr Thr Gln Lys Ser Leu Ser Leu Ser Pro Gly Lys
        435                 440                 445
```

<210> SEQ ID NO 59
<211> LENGTH: 447
<212> TYPE: PRT
<213> ORGANISM: Artificial sequence
<220> FEATURE:
<223> OTHER INFORMATION: Chemically synthesized - Heavy chain of
      O2-117

<400> SEQUENCE: 59

```
Glu Val Gln Leu Val Glu Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Ser Thr Pro Trp Phe Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

-continued

```
Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 60
<211> LENGTH: 1341
<212> TYPE: DNA
<213> ORGANISM: Artificial sequence
<220> FEATURE:
<223> OTHER INFORMATION: Chemically synthesized - Heavy chain of 02-118
<220> FEATURE:
<221> NAME/KEY: CDS
<222> LOCATION: (1)..(1341)

<400> SEQUENCE: 60

```
gag gtg cag ctg gtg gag tct ggg gga ggc ttg gta cat cct ggg ggg      48
Glu Val Gln Leu Val Glu Ser Gly Gly Gly Leu Val His Pro Gly Gly
1               5                   10                  15 tcc ctg aga ctc tcc tgt gca ggc tct gga ttc acc ttc agt agc tat      96
Ser Leu Arg Leu Ser Cys Ala Gly Ser Gly Phe Thr Phe Ser Ser Tyr
            20                  25                  30 gct atg cac tgg gtt cgc cag gct cca gga aaa ggt ctg gag tgg gta     144
Ala Met His Trp Val Arg Gln Ala Pro Gly Lys Gly Leu Glu Trp Val
        35                  40                  45 tca gct att agt act ggt ggt ggc aca tac tat gca gac tcc gtg aag     192
Ser Ala Ile Ser Thr Gly Gly Gly Thr Tyr Tyr Ala Asp Ser Val Lys
    50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
65                  70                  75                  80 caa atg aac agc ctg aga gcc gag gac acg gcc gtg tat tac tgt gca     288
Gln Met Asn Ser Leu Arg Ala Glu Asp Thr Ala Val Tyr Tyr Cys Ala
                85                  90                  95 agg agt gct tgg tgg ctg tcc ttt gac tcc tgg ggc cag ggc acc ctg     336
Arg Ser Ala Trp Trp Leu Ser Phe Asp Ser Trp Gly Gln Gly Thr Leu
            100                 105                 110 gtg acc gtc tcc agc gct agc acc aag ggc ccc agc gtg ttc ccc ctg     384
Val Thr Val Ser Ser Ala Ser Thr Lys Gly Pro Ser Val Phe Pro Leu
        115                 120                 125 gcc ccc agc agc aag agc acc agc ggc ggc aca gcc gcc ctg ggc tgc     432
Ala Pro Ser Ser Lys Ser Thr Ser Gly Gly Thr Ala Ala Leu Gly Cys
    130                 135                 140 ctg gtg aag gac tac ttc ccc gag ccc gtg acc gtg agc tgg aac agc     480
Leu Val Lys Asp Tyr Phe Pro Glu Pro Val Thr Val Ser Trp Asn Ser
145                 150                 155                 160 ggc gcc ttg acc agc ggc gtg cac acc ttc ccc gcc gtg ctg cag agc     528
Gly Ala Leu Thr Ser Gly Val His Thr Phe Pro Ala Val Leu Gln Ser
```

```
                    165                 170                 175
agc ggc ctg tac agc ctg agc agc gtg gtg acc gtg ccc agc agc agc         576
Ser Gly Leu Tyr Ser Leu Ser Ser Val Val Thr Val Pro Ser Ser Ser
            180                 185                 190 ctg ggc acc cag acc tac atc tgc aac gtg aac cac aag ccc agc aac         624
Leu Gly Thr Gln Thr Tyr Ile Cys Asn Val Asn His Lys Pro Ser Asn
        195                 200                 205 acc aag gtg gac aaa cgc gtg gag ccc aag agc tgc gac aag acc cac         672
Thr Lys Val Asp Lys Arg Val Glu Pro Lys Ser Cys Asp Lys Thr His
    210                 215                 220 acc tgc ccc ccc tgc cct gcc ccc gag ctg ctg ggc gga ccc tcc gtg         720
Thr Cys Pro Pro Cys Pro Ala Pro Glu Leu Leu Gly Gly Pro Ser Val
225                 230                 235                 240 ttc ctg ttc ccc ccc aag ccc aag gac acc ctc atg atc agc cgg acc         768
Phe Leu Phe Pro Pro Lys Pro Lys Asp Thr Leu Met Ile Ser Arg Thr
                245                 250                 255 ccc gag gtg acc tgc gtg gtg gtg gac gtg agc cac gag gac ccc gag         816
Pro Glu Val Thr Cys Val Val Val Asp Val Ser His Glu Asp Pro Glu
            260                 265                 270 gtg aag ttc aac tgg tac gtg gac ggc gtg gag gtg cac aac gcc aag         864
Val Lys Phe Asn Trp Tyr Val Asp Gly Val Glu Val His Asn Ala Lys
        275                 280                 285 acc aag ccc cgg gag gag cag tac aac agc acc tac cgg gtg gtg agc         912
Thr Lys Pro Arg Glu Glu Gln Tyr Asn Ser Thr Tyr Arg Val Val Ser
    290                 295                 300 gtg ctc acc gtg ctg cac cag gac tgg ctg aac ggc aag gag tac aag         960
Val Leu Thr Val Leu His Gln Asp Trp Leu Asn Gly Lys Glu Tyr Lys
305                 310                 315                 320 tgc aag gtg agc aac aag gcc ctg cct gcc ccc atc gag aag acc atc        1008
Cys Lys Val Ser Asn Lys Ala Leu Pro Ala Pro Ile Glu Lys Thr Ile
                325                 330                 335 agc aag gcc aag ggc cag ccc cgg gag ccc cag gtg tac acc ctg ccc        1056
Ser Lys Ala Lys Gly Gln Pro Arg Glu Pro Gln Val Tyr Thr Leu Pro
            340                 345                 350 ccc agc cgg gag gag atg acc aag aac cag gtg tcc ctc acc tgt ctg        1104
Pro Ser Arg Glu Glu Met Thr Lys Asn Gln Val Ser Leu Thr Cys Leu
        355                 360                 365 gtg aag ggc ttc tac ccc agc gac atc gcc gtg gag tgg gag agc aac        1152
Val Lys Gly Phe Tyr Pro Ser Asp Ile Ala Val Glu Trp Glu Ser Asn
    370                 375                 380 ggc cag ccc gag aac aac tac aag acc acc ccc cct gtg ctg gac agc        1200
Gly Gln Pro Glu Asn Asn Tyr Lys Thr Thr Pro Pro Val Leu Asp Ser
385                 390                 395                 400 gac ggc agc ttc ttc ctg tac agc aag ctc acc gtg gac aag agc cgg        1248
Asp Gly Ser Phe Phe Leu Tyr Ser Lys Leu Thr Val Asp Lys Ser Arg
                405                 410                 415 tgg cag cag ggc aac gtg ttc agc tgc agc gtg atg cac gag gcc ctg        1296
Trp Gln Gln Gly Asn Val Phe Ser Cys Ser Val Met His Glu Ala Leu
            420                 425                 430 cac aac cac tac acc cag aag agc ctg agc ctg agc ccc ggc aag            1341
His Asn His Tyr Thr Gln Lys Ser Leu Ser Leu Ser Pro Gly Lys
        435                 440                 445

<210> SEQ ID NO 61
<211> LENGTH: 447
<212> TYPE: PRT
<213> ORGANISM: Artificial sequence
<220> FEATURE:
<223> OTHER INFORMATION: Chemically synthesized - Heavy chain of
      02-118

<400> SEQUENCE: 61
```

-continued

```
Glu Val Gln Leu Val Glu Ser Gly Gly Gly Leu Val His Pro Gly Gly
1               5                   10                  15
Ser Leu Arg Leu Ser Cys Ala Gly Ser Gly Phe Thr Phe Ser Ser Tyr
            20                  25                  30
Ala Met His Trp Val Arg Gln Ala Pro Gly Lys Gly Leu Glu Trp Val
        35                  40                  45
Ser Ala Ile Ser Thr Gly Gly Thr Tyr Tyr Ala Asp Ser Val Lys
    50                  55                  60
Gly Arg Phe Thr Ile Ser Arg Asp Asn Ala Lys Asn Ser Leu Tyr Leu
65              70                  75                  80
Gln Met Asn Ser Leu Arg Ala Glu Asp Thr Ala Val Tyr Tyr Cys Ala
            85                  90                  95
Arg Ser Ala Trp Trp Leu Ser Phe Asp Ser Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
            165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Arg Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
            245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
            325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
            405                 410                 415
Trp Gln Gln Gly Asn Val Phe Ser Cys Ser Val Met His Glu Ala Leu
```

```
                         420                 425                 430
His Asn His Tyr Thr Gln Lys Ser Leu Ser Leu Ser Pro Gly Lys
        435                 440                 445

<210> SEQ ID NO 62
<211> LENGTH: 642
<212> TYPE: DNA
<213> ORGANISM: Artificial sequence
<220> FEATURE:
<223> OTHER INFORMATION: Chemically synthesized - Light chain of
      02-113, 02-114, 02-116, 02-117 and 02-118
<220> FEATURE:
<221> NAME/KEY: CDS
<222> LOCATION: (1)..(642)

<400> SEQUENCE: 62 gac att cag atg acc cag tct cca tcc tcc ctg tct gca tct gta gga      48
Asp Ile Gln Met Thr Gln Ser Pro Ser Ser Leu Ser Ala Ser Val Gly
1               5                   10                  15 gac aga gtc acc atc act tgc cgg gca agt cag agc att agc agc tac      96
Asp Arg Val Thr Ile Thr Cys Arg Ala Ser Gln Ser Ile Ser Ser Tyr
            20                  25                  30 tta aat tgg tat cag cag aaa cca ggg aaa gcc cct aag ctc ctg atc     144
Leu Asn Trp Tyr Gln Gln Lys Pro Gly Lys Ala Pro Lys Leu Leu Ile
        35                  40                  45 tat gct gca tcc agt ttg caa agt ggg gtc cca tca agg ttc agt ggc     192
Tyr Ala Ala Ser Ser Leu Gln Ser Gly Val Pro Ser Arg Phe Ser Gly
    50                  55                  60 agt gga tct ggg aca gat ttc act ctc acc atc agc agt ctg caa cct     240
Ser Gly Ser Gly Thr Asp Phe Thr Leu Thr Ile Ser Ser Leu Gln Pro
65                  70                  75                  80 gaa gat ttt gca act tac tac tgt caa cag agt tac agt acc cct cca     288
Glu Asp Phe Ala Thr Tyr Tyr Cys Gln Gln Ser Tyr Ser Thr Pro Pro
                85                  90                  95 acg ttc ggc caa ggg acc aag gtg gag atc aaa cgg acc gtg gcc gct     336
Thr Phe Gly Gln Gly Thr Lys Val Glu Ile Lys Arg Thr Val Ala Ala
            100                 105                 110 ccc agc gtg ttc atc ttc ccc ccc tcc gac gag cag ctg aag agc ggc     384
Pro Ser Val Phe Ile Phe Pro Pro Ser Asp Glu Gln Leu Lys Ser Gly
        115                 120                 125 acc gcc agc gtg gtg tgc ctg ctg aac aac ttc tac ccc cgg gag gcc     432
Thr Ala Ser Val Val Cys Leu Leu Asn Asn Phe Tyr Pro Arg Glu Ala
    130                 135                 140 aag gtg cag tgg aag gtg gac aac gcc ctg cag agc ggc aac agc cag     480
Lys Val Gln Trp Lys Val Asp Asn Ala Leu Gln Ser Gly Asn Ser Gln
145                 150                 155                 160 gag agc gtg acc gag cag gac agc aag gac tcc acc tac agc ctg agc     528
Glu Ser Val Thr Glu Gln Asp Ser Lys Asp Ser Thr Tyr Ser Leu Ser
                165                 170                 175 agc acc ctc acc ctg agc aag gcc gac tac gag aag cac aag gtg tac     576
Ser Thr Leu Thr Leu Ser Lys Ala Asp Tyr Glu Lys His Lys Val Tyr
            180                 185                 190 gcc tgc gag gtg acc cac cag ggc ctg agc agc ccc gtg acc aag agc     624
Ala Cys Glu Val Thr His Gln Gly Leu Ser Ser Pro Val Thr Lys Ser
        195                 200                 205 ttc aac cgg ggc gag tgt                                             642
Phe Asn Arg Gly Glu Cys
    210

<210> SEQ ID NO 63
<211> LENGTH: 214
<212> TYPE: PRT
<213> ORGANISM: Artificial sequence
```

<220> FEATURE:
<223> OTHER INFORMATION: Chemically synthesized - Light chain of
      02-113, 02-114, 02-116, 02-117 and 02-118

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 64
<211> LENGTH: 696
<212> TYPE: DNA
<213> ORGANISM: Artificial sequence
<220> FEATURE:
<223> OTHER INFORMATION: Chemically synthesized - Light chain of
      02-115
<220> FEATURE:
<221> NAME/KEY: CDS
<222> LOCATION: (1)..(696)

<400> SEQUENCE: 64 tcc tcc gag ctg acc cag gac cct gct gtg tct gtg gcc ttg gga cag     48
Ser Ser Glu Leu Thr Gln Asp Pro Ala Val Ser Val Ala Leu Gly Gln
1               5                   10                  15 aca gtc agg atc aca tgc caa gga gac agc ctc aga agc tat tat gca     96
Thr Val Arg Ile Thr Cys Gln Gly Asp Ser Leu Arg Ser Tyr Tyr Ala
            20                  25                  30 agc tgg tac cag cag aag cca gga cag gcc cct gta ctt gtc atc tat    144
Ser Trp Tyr Gln Gln Lys Pro Gly Gln Ala Pro Val Leu Val Ile Tyr
        35                  40                  45 ggt aaa aac aac cgg ccc tca ggg atc cca gac cga ttc tct ggc tcc    192
Gly Lys Asn Asn Arg Pro Ser Gly Ile Pro Asp Arg Phe Ser Gly Ser
50                  55                  60 agc tca gga aac aca gct tcc ttg acc atc act ggg gct cag gcg gaa    240
Ser Ser Gly Asn Thr Ala Ser Leu Thr Ile Thr Gly Ala Gln Ala Glu

```
                            65                  70                  75                  80
gat gag gct gac tat tac tgt aac tcc cgg gac agc agt ggt aac cat          288
Asp Glu Ala Asp Tyr Tyr Cys Asn Ser Arg Asp Ser Ser Gly Asn His
                85                  90                  95 gtg gta ttc ggc gga ggg acc aag ctg acc gtc cta ggt gag tcg cgg          336
Val Val Phe Gly Gly Gly Thr Lys Leu Thr Val Leu Gly Glu Ser Arg
            100                 105                 110 ccg caa gct tac cgt gct ggg cca gcc caa ggc cgc tcc cag cgt gac          384
Pro Gln Ala Tyr Arg Ala Gly Pro Ala Gln Gly Arg Ser Gln Arg Asp
            115                 120                 125 cct gtt ccc ccc ctc ctc cga gga gct gca ggc caa caa ggc cac cct          432
Pro Val Pro Pro Leu Leu Arg Gly Ala Ala Gly Gln Gln Gly His Pro
    130                 135                 140 ggt gtg cct cat cag cga ctt cta ccc tgg cgc cgt gac cgt ggc ctg          480
Gly Val Pro His Gln Arg Leu Leu Pro Trp Arg Arg Asp Arg Gly Leu
145                 150                 155                 160 gaa ggc cga cag cag ccc cgt gaa ggc cgg cgt gga gac cac cac ccc          528
Glu Gly Arg Gln Gln Pro Arg Glu Gly Arg Arg Gly Asp His His Pro
                165                 170                 175 cag caa gca gag caa caa caa gta cgc cgc cag cag cta cct gag cct          576
Gln Gln Ala Glu Gln Gln Gln Val Arg Arg Gln Gln Leu Pro Glu Pro
            180                 185                 190 cac ccc cga gca gtg gaa gag cca ccg gag cta cag ctg cca ggt gac          624
His Pro Arg Ala Val Glu Glu Pro Pro Glu Leu Gln Leu Pro Gly Asp
            195                 200                 205 cca cga ggg cag cac cgt gga gaa gac cgt ggc ccc cac cga gtg cag          672
Pro Arg Gly Gln His Arg Gly Glu Asp Arg Gly Pro His Arg Val Gln
    210                 215                 220 cta ata gac tta agt tta aac cgc                                          696
Leu Ile Asp Leu Ser Leu Asn Arg
225                 230

<210> SEQ ID NO 65
<211> LENGTH: 232
<212> TYPE: PRT
<213> ORGANISM: Artificial sequence
<220> FEATURE:
<223> OTHER INFORMATION: Chemically synthesized - Light chain of
      02-115

<400> SEQUENCE: 65

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu Gly Glu Ser Arg
            100                 105                 110

Pro Gln Ala Tyr Arg Ala Gly Pro Ala Gln Gly Arg Ser Gln Arg Asp
            115                 120                 125

Pro Val Pro Pro Leu Leu Arg Gly Ala Ala Gly Gln Gln Gly His Pro
    130                 135                 140
```

```
Gly Val Pro His Gln Arg Leu Leu Pro Trp Arg Arg Asp Arg Gly Leu
145                 150                 155                 160

Glu Gly Arg Gln Gln Pro Arg Glu Gly Arg Gly Asp His His Pro
                165                 170                 175

Gln Gln Ala Glu Gln Gln Val Arg Gln Gln Leu Pro Glu Pro
            180                 185                 190

His Pro Arg Ala Val Glu Glu Pro Glu Leu Gln Leu Pro Gly Asp
        195                 200                 205

Pro Arg Gly Gln His Arg Gly Glu Asp Arg Gly Pro His Arg Val Gln
    210                 215                 220

Leu Ile Asp Leu Ser Leu Asn Arg
225                 230
```

<210> SEQ ID NO 66
<211> LENGTH: 5
<212> TYPE: PRT
<213> ORGANISM: Artificial sequence
<220> FEATURE:
<223> OTHER INFORMATION: Chemically synthesized - HCDR1 of
      SC02-113

<400> SEQUENCE: 66

```
Gly Tyr Tyr Trp Ser
1               5
```

<210> SEQ ID NO 67
<211> LENGTH: 16
<212> TYPE: PRT
<213> ORGANISM: Artificial sequence
<220> FEATURE:
<223> OTHER INFORMATION: Chemically synthesized - HCDR2 of SC02-113

<400> SEQUENCE: 67

```
Tyr Ile Tyr Tyr Ser Gly Ser Thr Asn Tyr Asn Pro Ser Leu Lys Ser
1               5                   10                  15
```

<210> SEQ ID NO 68
<211> LENGTH: 11
<212> TYPE: PRT
<213> ORGANISM: Artificial sequence
<220> FEATURE:
<223> OTHER INFORMATION: Chemically synthesized - LCDR1 of SC02-113 and
      SC02-118

<400> SEQUENCE: 68

```
Arg Ala Ser Gln Ser Ile Ser Ser Tyr Leu Asn
1               5                   10
```

<210> SEQ ID NO 69
<211> LENGTH: 7
<212> TYPE: PRT
<213> ORGANISM: Artificial sequence
<220> FEATURE:
<223> OTHER INFORMATION: Chemically synthesized - LCDR2 of SC02-113 and
      SC02-118

<400> SEQUENCE: 69

```
Ala Ala Ser Ser Leu Gln Ser
1               5
```

<210> SEQ ID NO 70
<211> LENGTH: 7
<212> TYPE: PRT
<213> ORGANISM: Artificial sequence
<220> FEATURE:
<223> OTHER INFORMATION: Chemically synthesized - LCDR3 of SC02-113 and

```
                           -continued

SC02-118

<400> SEQUENCE: 70

Gln Gln Ser Tyr Ser Thr Pro
1               5

<210> SEQ ID NO 71
<211> LENGTH: 5
<212> TYPE: PRT
<213> ORGANISM: Artificial sequence
<220> FEATURE:
<223> OTHER INFORMATION: Chemically synthesized - HCDR1 of SC02-118

<400> SEQUENCE: 71

Ser Tyr Ala Met His
1               5

<210> SEQ ID NO 72
<211> LENGTH: 16
<212> TYPE: PRT
<213> ORGANISM: Artificial sequence
<220> FEATURE:
<223> OTHER INFORMATION: Chemically synthesized - HCDR2 of SC02-118

<400> SEQUENCE: 72

Ala Ile Ser Thr Gly Gly Gly Thr Tyr Tyr Ala Asp Ser Val Lys Gly
1               5                   10                  15
```